US008060207B2

(12) United States Patent
Wallace et al.

(10) Patent No.: US 8,060,207 B2
(45) Date of Patent: *Nov. 15, 2011

(54) METHOD OF INTRAVASCULARLY DELIVERING STIMULATION LEADS INTO DIRECT CONTACT WITH TISSUE

(75) Inventors: Michael P. Wallace, Fremont, CA (US);
Kamal Ramzipoor, Fremont, CA (US);
Robert J. Garabedian, Mountain View, CA (US); Robert M. Abrams, Los Gatos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1328 days.

This patent is subject to a terminal disclaimer.

(21) Appl. No.: 10/744,853

(22) Filed: Dec. 22, 2003

(65) Prior Publication Data

US 2005/0137647 A1 Jun. 23, 2005

(51) Int. Cl.
*A61N 1/00* (2006.01)
(52) U.S. Cl. .............................................. 607/45
(58) Field of Classification Search .......... 607/2, 45–50, 607/116
See application file for complete search history.

(56) References Cited

U.S. PATENT DOCUMENTS

| | | |
|---|---|---|
| 4,141,365 A | 2/1979 | Fischell et al. |
| 4,285,347 A | 8/1981 | Hess |
| 4,519,403 A | 5/1985 | Dickhudt |
| 4,608,985 A | 9/1986 | Crish et al. |
| 4,658,835 A | 4/1987 | Pohndorf |
| 4,739,768 A | 4/1988 | Engelson |
| 4,813,934 A | 3/1989 | Engelson et al. |
| 4,869,255 A | 9/1989 | Putz |
| 4,884,579 A | 12/1989 | Engelson |
| 5,005,587 A | 4/1991 | Scott |
| 5,010,894 A | 4/1991 | Edhag |
| 5,170,802 A | 12/1992 | Mehra |
| 5,224,491 A | 7/1993 | Mehra |
| 5,234,437 A | 8/1993 | Sepetka |
| 5,239,999 A | 8/1993 | Imran |
| 5,250,071 A | 10/1993 | Palermo |

(Continued)

FOREIGN PATENT DOCUMENTS

EP 0 865 800 A2 9/1998

(Continued)

OTHER PUBLICATIONS

Methods of Placement of Neurostimulation Lead, Infusion Catheter, and/or Sensor via the Vasculature to the Brain. IP.com; IPCOM000012135D; Apr. 10, 2003.*

(Continued)

*Primary Examiner* — Eric D. Bertram
(74) *Attorney, Agent, or Firm* — Vista IP Law Group LLP

(57) ABSTRACT

A method of treating a disorder in a patient is provided. The method comprises delivering a stimulation lead within a blood vessel, intralumenally puncturing a wall of the blood vessel to create an exit point, and then introducing the stimulation lead through the exit point into direct contact with tissue the stimulation of which treats the disorder. Optionally, the method comprises implanting a source of stimulation within the patient's body, and then electrically coupling the proximal end of the stimulation lead to the implanted stimulation source. Using the stimulation lead, the tissue can then be stimulated in order to treat the disorder.

43 Claims, 42 Drawing Sheets

U.S. PATENT DOCUMENTS

| | | | |
|---|---|---|---|
| 5,261,916 A | 11/1993 | Engelson | |
| 5,263,488 A | 11/1993 | Van Veen et al. | |
| 5,304,195 A | 4/1994 | Twyford, Jr. et al. | |
| 5,312,415 A | 5/1994 | Palermo | |
| 5,350,397 A | 9/1994 | Palermo et al. | |
| 5,365,926 A | 11/1994 | Desai | |
| 5,391,200 A | 2/1995 | KenKnight et al. | |
| 5,397,341 A | 3/1995 | Hirschberg et al. | |
| 5,411,551 A | 5/1995 | Winston et al. | |
| 5,417,719 A | 5/1995 | Hull et al. | |
| 5,423,864 A | 6/1995 | Ljungstroem | |
| 5,443,481 A * | 8/1995 | Lee | 606/213 |
| 5,501,703 A | 3/1996 | Holsheimer et al. | |
| 5,509,411 A | 4/1996 | Littmann et al. | |
| 5,531,779 A | 7/1996 | Dahl et al. | |
| 5,534,007 A | 7/1996 | St. Germain et al. | |
| 5,543,864 A | 8/1996 | Hirschman et al. | |
| 5,603,731 A | 2/1997 | Whitney | |
| 5,647,870 A | 7/1997 | Kordis et al. | |
| 5,683,422 A | 11/1997 | Rise | |
| 5,702,438 A | 12/1997 | Avitall | |
| 5,707,354 A | 1/1998 | Salmon et al. | |
| 5,713,922 A | 2/1998 | King | |
| 5,716,377 A | 2/1998 | Rise et al. | |
| 5,752,979 A | 5/1998 | Benabid | |
| 5,782,239 A | 7/1998 | Webster, Jr. | |
| 5,792,187 A | 8/1998 | Adams | |
| 5,800,474 A | 9/1998 | Benabid et al. | |
| 5,814,062 A | 9/1998 | Sepetka et al. | |
| 5,833,709 A | 11/1998 | Rise et al. | |
| 5,846,238 A | 12/1998 | Jackson et al. | |
| 5,860,974 A | 1/1999 | Abele | |
| 5,871,483 A | 2/1999 | Jackson et al. | |
| 5,891,136 A | 4/1999 | McGee et al. | |
| 5,897,584 A | 4/1999 | Herman | |
| 5,902,236 A | 5/1999 | Iversen | |
| 5,908,385 A | 6/1999 | Chechelski et al. | |
| 5,925,070 A | 7/1999 | King et al. | |
| 5,938,689 A | 8/1999 | Fischell et al. | |
| 5,954,761 A | 9/1999 | Machek et al. | |
| 5,967,986 A | 10/1999 | Cimochowski et al. | |
| 6,006,134 A | 12/1999 | Hill et al. | |
| 6,015,387 A | 1/2000 | Schwartz et al. | |
| 6,016,449 A | 1/2000 | Fischell et al. | |
| 6,018,682 A | 1/2000 | Rise | |
| 6,027,456 A | 2/2000 | Feler et al. | |
| 6,053,873 A | 4/2000 | Govari et al. | |
| 6,066,163 A | 5/2000 | John | |
| 6,074,407 A | 6/2000 | Levine et al. | |
| 6,074,507 A | 6/2000 | Sukenik | |
| 6,091,980 A | 7/2000 | Squire et al. | |
| 6,094,596 A | 7/2000 | Morgan | |
| 6,119,044 A | 9/2000 | Kuzma | |
| 6,122,548 A | 9/2000 | Starkebaum et al. | |
| 6,128,538 A * | 10/2000 | Fischell et al. | 607/45 |
| 6,136,021 A | 10/2000 | Tockman et al. | |
| 6,141,576 A | 10/2000 | Littmann et al. | |
| 6,161,029 A | 12/2000 | Spreigl et al. | |
| 6,161,047 A | 12/2000 | King et al. | |
| 6,170,488 B1 | 1/2001 | Spillman, Jr. et al. | |
| 6,179,858 B1 | 1/2001 | Squire et al. | |
| 6,205,361 B1 | 3/2001 | Kuzma et al. | |
| 6,216,045 B1 | 4/2001 | Black et al. | |
| 6,231,516 B1 | 5/2001 | Keilman et al. | |
| 6,249,707 B1 | 6/2001 | Kohnen et al. | |
| 6,263,237 B1 | 7/2001 | Rise | |
| 6,263,248 B1 | 7/2001 | Farley et al. | |
| 6,266,568 B1 | 7/2001 | Mann et al. | |
| 6,319,251 B1 | 11/2001 | Tu et al. | |
| 6,330,477 B1 * | 12/2001 | Casavant | 607/14 |
| 6,353,762 B1 | 3/2002 | Baudino et al. | |
| 6,360,122 B1 | 3/2002 | Fischell et al. | |
| 6,361,528 B1 | 3/2002 | Wilson et al. | |
| 6,370,427 B1 | 4/2002 | Alt et al. | |
| 6,391,052 B2 | 5/2002 | Buirge et al. | |
| 6,393,325 B1 | 5/2002 | Mann et al. | |
| 6,397,109 B1 | 5/2002 | Cammilli et al. | |
| 6,398,780 B1 * | 6/2002 | Farley et al. | 606/41 |
| 6,402,746 B1 | 6/2002 | Whayne et al. | |
| 6,408,214 B1 * | 6/2002 | Williams et al. | 607/122 |
| 6,415,187 B1 | 7/2002 | Kuzma et al. | |
| 6,418,344 B1 * | 7/2002 | Rezai et al. | 607/45 |
| 6,438,427 B1 | 8/2002 | Rexhausen et al. | |
| 6,442,413 B1 | 8/2002 | Silver | |
| 6,442,435 B2 | 8/2002 | King et al. | |
| 6,445,953 B1 | 9/2002 | Bulkes et al. | |
| 6,463,328 B1 | 10/2002 | John | |
| 6,466,822 B1 | 10/2002 | Pless | |
| 6,480,743 B1 | 11/2002 | Kirkpatrick et al. | |
| 6,484,059 B2 | 11/2002 | Gielen | |
| 6,516,227 B1 | 2/2003 | Meadows et al. | |
| 6,519,488 B2 | 2/2003 | KenKnight et al. | |
| 6,522,932 B1 | 2/2003 | Kuzma et al. | |
| 6,529,774 B1 | 3/2003 | Greene | |
| 6,539,263 B1 | 3/2003 | Schiff et al. | |
| 6,547,788 B1 | 4/2003 | Maguire et al. | |
| 6,547,870 B1 | 4/2003 | Griessmann et al. | |
| 6,562,063 B1 | 5/2003 | Euteneuer et al. | |
| 6,584,358 B2 | 6/2003 | Carter et al. | |
| 6,587,733 B1 | 7/2003 | Cross, Jr. et al. | |
| 6,589,230 B2 | 7/2003 | Gia et al. | |
| 6,591,138 B1 | 7/2003 | Fischell et al. | |
| 6,597,953 B2 | 7/2003 | Boling | |
| 6,600,954 B2 | 7/2003 | Cohen et al. | |
| 6,606,521 B2 | 8/2003 | Paspa et al. | |
| 6,647,296 B2 | 11/2003 | Fischell et al. | |
| 6,658,302 B1 | 12/2003 | Kuzma et al. | |
| 6,662,055 B1 | 12/2003 | Prutchi | |
| 6,665,562 B2 | 12/2003 | Gluckman et al. | |
| 6,690,974 B2 | 2/2004 | Archer et al. | |
| 6,697,676 B2 | 2/2004 | Dahl et al. | |
| 6,842,648 B2 | 1/2005 | Partridge et al. | |
| 6,895,283 B2 | 5/2005 | Erickson et al. | |
| 2001/0025192 A1 | 9/2001 | Gerber et al. | |
| 2001/0041821 A1 | 11/2001 | Wilk | |
| 2001/0053885 A1 | 12/2001 | Gielen et al. | |
| 2002/0062143 A1 * | 5/2002 | Baudino et al. | 607/116 |
| 2002/0077684 A1 * | 6/2002 | Clemens et al. | 607/116 |
| 2002/0111661 A1 | 8/2002 | Cross, Jr. et al. | |
| 2002/0151948 A1 | 10/2002 | King et al. | |
| 2002/0151949 A1 | 10/2002 | Dahl et al. | |
| 2002/0188207 A1 | 12/2002 | Richter | |
| 2003/0014016 A1 * | 1/2003 | Purdy | 604/174 |
| 2003/0040785 A1 | 2/2003 | Maschino et al. | |
| 2003/0100931 A1 | 5/2003 | Mullett | |
| 2003/0199962 A1 | 10/2003 | Struble et al. | |
| 2003/0204135 A1 | 10/2003 | Bystritsky | |
| 2003/0204228 A1 | 10/2003 | Cross, Jr. et al. | |
| 2004/0015193 A1 | 1/2004 | Lamson et al. | |
| 2006/0195169 A1 | 8/2006 | Gross et al. | |

FOREIGN PATENT DOCUMENTS

| | | |
|---|---|---|
| EP | 0 881 676 | 9/1998 |
| EP | 0 865 800 A3 | 12/1999 |
| EP | 0 864 800 B1 | 9/2004 |
| WO | WO 01/85094 | 11/2001 |
| WO | WO 03/077986 | 9/2003 |

OTHER PUBLICATIONS

Gray, Henry. "Anatomy of the Human Body." 1918, Figure 769.*

Lewin, Walpole. "Changing attitudes to the management of severe head injuries." British Medical Journal, 1976, 2, 1234-1239.*

IP.com: Electrotrode Design to Stimulate Blood Vessels, Nerves, or Other Tubular Organs, file://C:\unzipped\IPCOM000010247D1\0_properties.xml, Published Nov. 13, 2002.

IP.com: Epidural Needle for Spinal Cord Stimulation Electrode, file://C:\unzipped\IPCOM000011384D1\0_properties.xml, Published Feb. 14, 2003.

IP.com: Medical Lead System and Method for Insertion into the Spinal Cord, file://C:\unzipped\IPCOM000011389D1\0_properties.xml, Published Feb. 17, 2003.

IP.com: Transcutaneous Screening Test for Evaluation of Potential Efficacy of Chronic Trigeminal Neurostimulation as a Therapy for Epilepsy, file://C:\unzipped\IPCOM000011987D1\0_properties.xml, Published Mar. 28, 2003.

IP.com: System and Method for Lead Fixation, file://C:\unzipped\IPCOM000019571D1\0_properties.xml, Published Sep. 19, 2003.

IP.com: Dual Lumen Inflatable Lead, file://C:\unzipped\IPCOM000019703D1\0_properties.xml, Published Sep. 25, 2003.

IP.com: Skull-Mounted Electrical Stimulation System, file://C:\unzipped\IPCOM000019827D1\0_properties.xml, Published Oct. 1, 2003.

IP.com: Spinal Cord Stimulation as a Therapy for Epilepsy, file://C:\unzipped\IPCOM000019881D1\0_properties.xml, Published Oct. 6, 2003.

IP.com: Skull-Mounted Electrical Stimulation System and Method for Treating Patients, file://C:\unzipped\IPCOM000021554D1\0_properties.xml, Published Jan. 22, 2004.

Canavero, Sergio et al., "Extradural Motor Cortex Stimulation for Advanced Parkinson Disease," J. Neurosurg. 97: pp. 1208-1211, 2002.

Kunieda, Takeharu et al., "Use of Cavernous Sinus EEG in the Detection of Seizure Onset and Spread in Mesial Temporal Lobe Epilepsy," Epilepsia, 41(11): pp. 1411-1419, 2000.

Onal, Cagatay, "Complications of Invasive Subdural Grid Monitoring in Children with Epilepsy," J. Neurosurg. 98: pp. 1017-1026, 2003.

PCT International Search Report for PCT/US2005/006569, Applicant: Boston Scientific Scimed, Inc., Forms PCT/ISA 210 and 220, dated Jun. 13, 2005 (7 pages).

PCT Written Opinion of the International Search Authority for PCT/US2005/006569, Applicant: Boston Scientific Scimed, Inc., Form PCT/ISA/237, dated Jun. 13, 2005 (5 pages).

PCT International Search Report for PCT/US2005/010121, Applicant: Boston Scientific Scimed, Inc., Forms PCT/ISA/210 and 220, dated Jul. 4, 2005 (7 pages).

PCT Written Opinion of the International Search Authority for PCT/US2005/010121, Applicant: Boston Scientific Scimed, Inc., Form PCT/ISA/237, dated Jul. 4, 2005 (5 pages).

"Methods of Placement of Neurostimulation Lead, Infusion Catheter, and/or Sensor via Peripheral Vasculatur", IP.com; IPCOM000012136D, Apr. 10, 2003 (8pages).

"Methods of Placement of Neurostimulation.Lead, Infusion Catheter, and/or Sensor via the Vasculature to the Brain", IP.com; IPCOM000012135D, Apr. 10, 2003 (11pages).

IPCOM000012135D; IP.com. Methods of Placement of Neurostimulation Lead, Infusion Catheter, and/or Sensor Via the Vasculature to the Brain, Apr. 10, 2003.

0349945-003 IP.com: Methods of Placement of Neurostimulation Lead, Infusion Catheter, and or Sensor via Peripheral Vasculature, Jul. 18, 2005.

\* cited by examiner

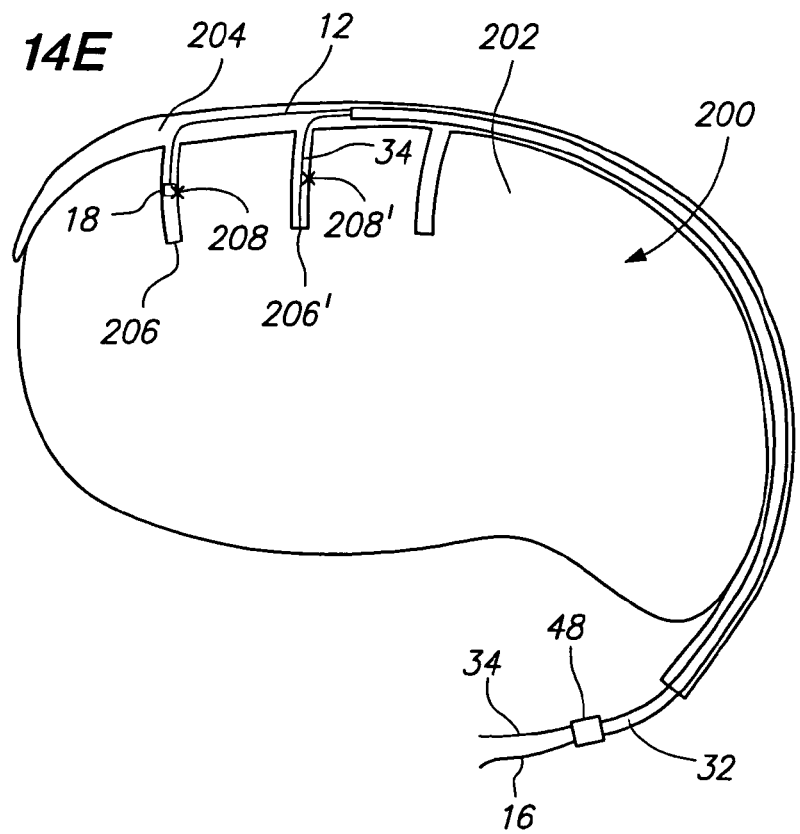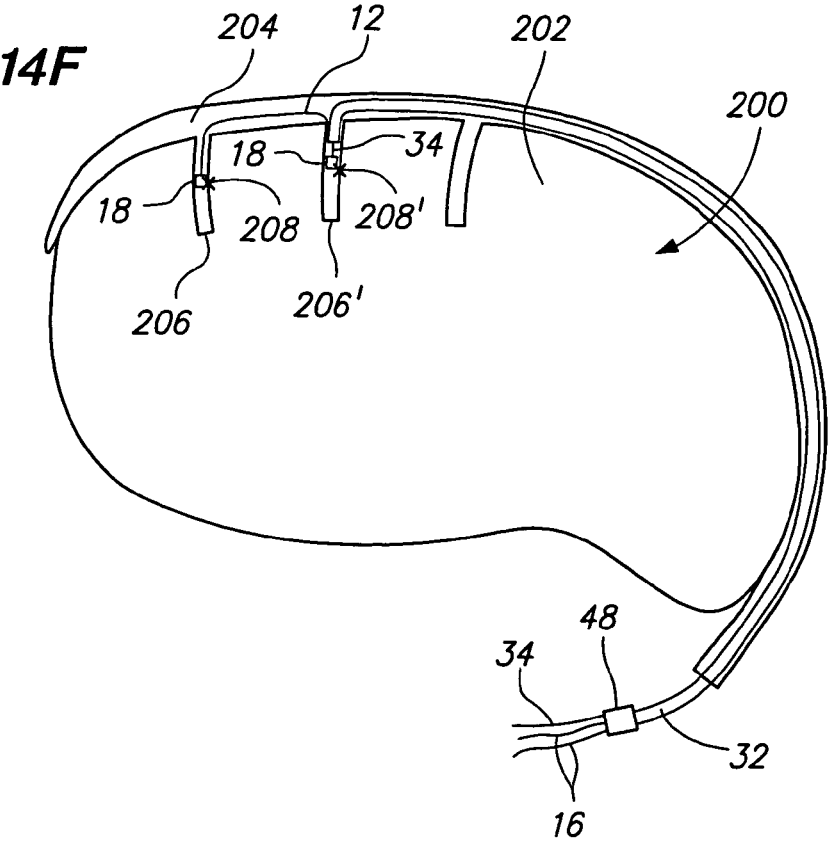

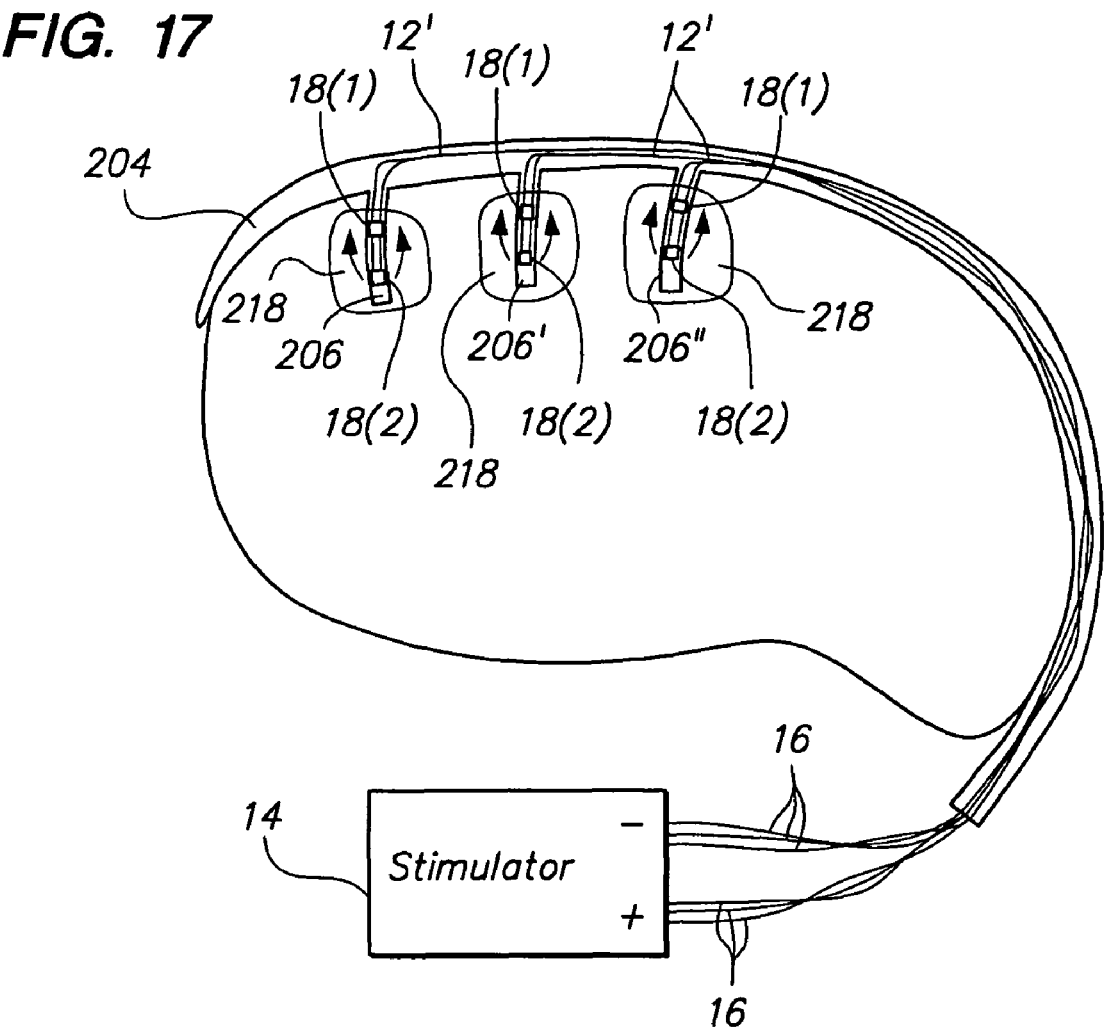

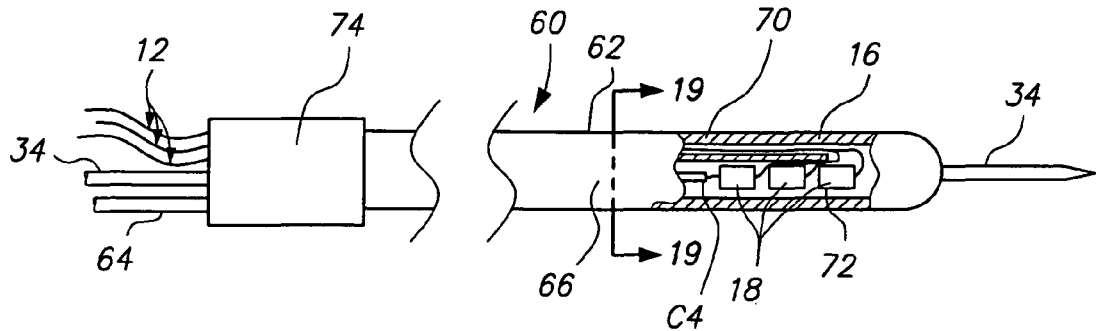
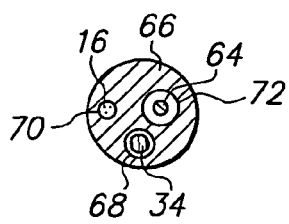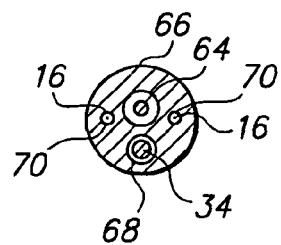
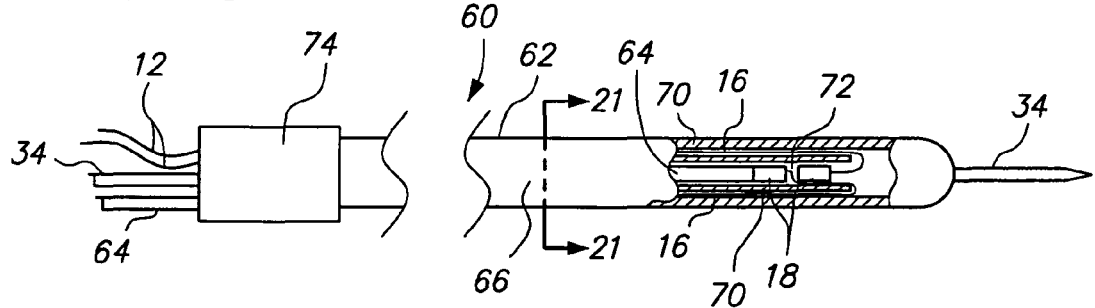
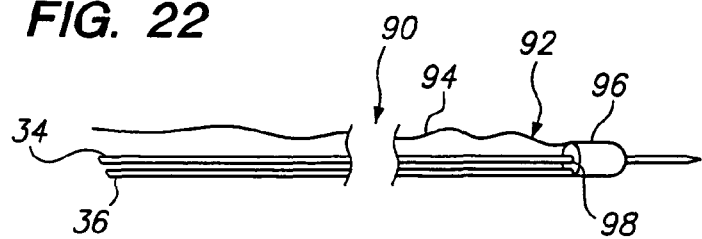

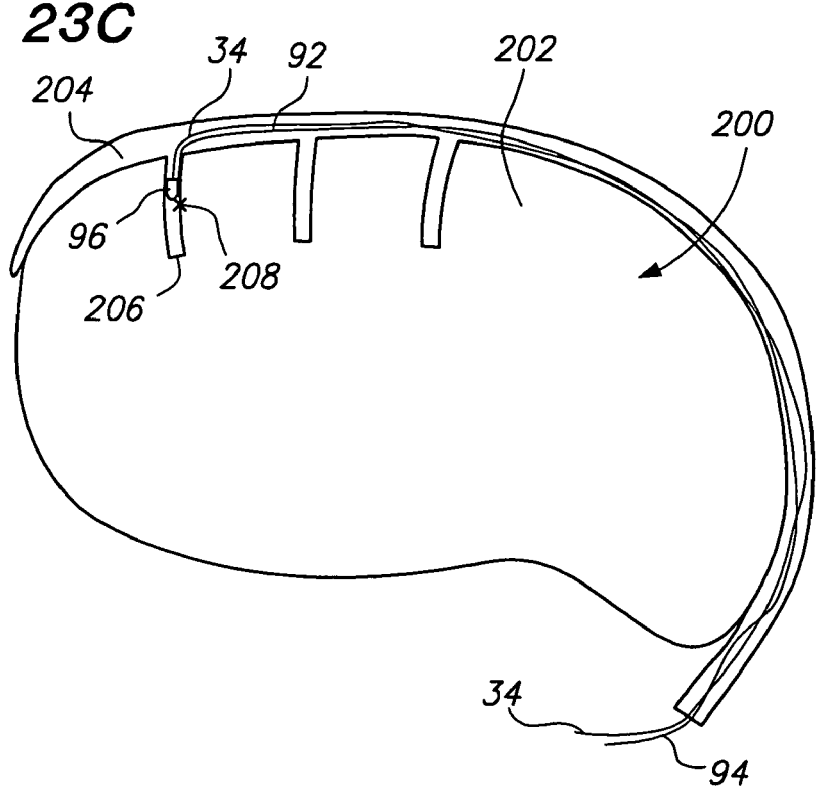
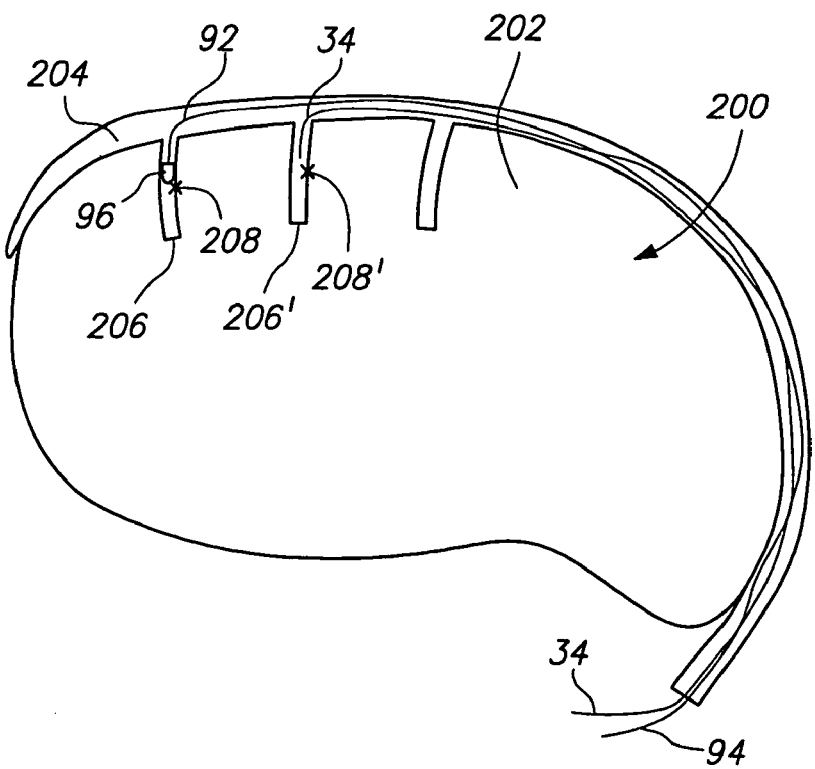

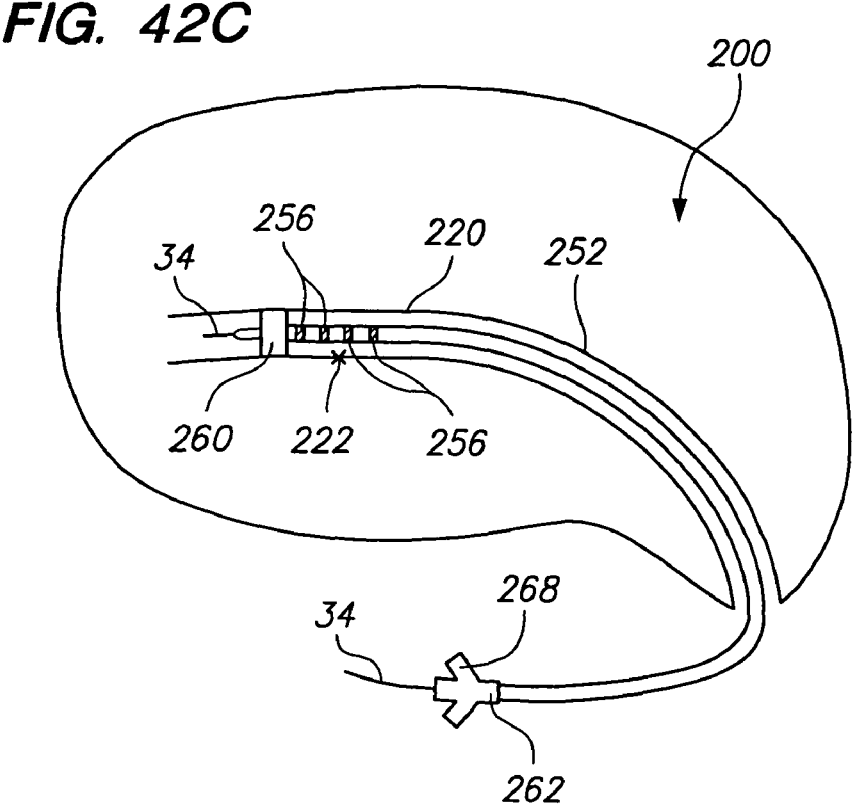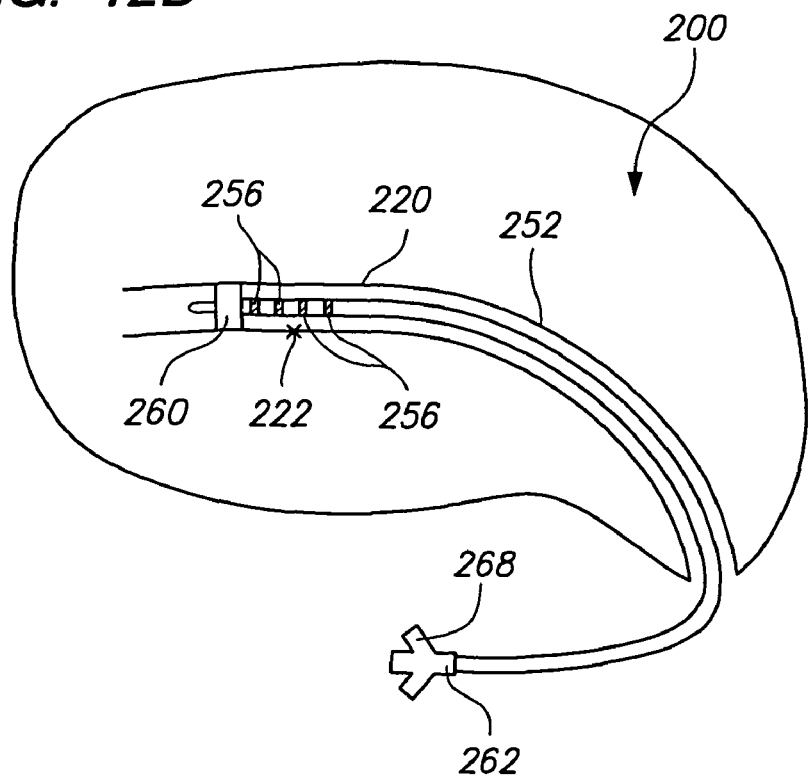

METHOD OF INTRAVASCULARLY DELIVERING STIMULATION LEADS INTO DIRECT CONTACT WITH TISSUE

RELATED APPLICATIONS

This application is related to copending U.S. patent application Ser. No. 10/744,319, filed on the same date, and expressly incorporated herein by reference.

FIELD OF THE INVENTION

The invention relates to the treatment of diseases, and in particular, the therapeutic treatment of tissue using electrical stimulation.

BACKGROUND OF THE INVENTION

It is known to treat neurodegenerative diseases, such as Alzheimer's Disease, Parkinson's Disease, Tremor, and Epilepsy, and ischemia of the brain, such as stroke, by electrically stimulating selected portions of the brain. Currently, this is accomplished by first drilling a burr hole through the patient's cranium in order to gain access to the brain tissue. A stimulation lead, and in particular, a lead with multiple electrodes extending along its length, is then introduced through one or more burr holes into contact with the selected brain tissue. In a deep brain stimulation (DBS) procedure, typically used to treat Parkinson's Disease, Tremor, and Epilepsy, the stimulation lead is advanced through a burr hole deep into the brain, e.g., the anterior thalamus, ventrolateral thalamus (Thal), internal segment of globus pallidus (GPi), substantia nigra pars reticulata (SNr), subthalamic nucleus (STN), external segment of globus pallidus (GPe), and neostriatum. In a cortical brain stimulation procedure, typically used to rehabilitate stroke victims, the lead is introduced through two burr holes and placed underneath the dura matter in contact with the cortex of the brain.

Once the lead is properly located in contact with the selected brain tissue, the proximal end of the lead or an extension lead is subcutaneously routed from the burr hole underneath the patient's scalp, down the neck, and into the chest region in electrical connection with an implanted electrical stimulator. The electrical stimulator is programmed either prior to or after the procedure to deliver electrical pulses to the brain tissue via the stimulation lead.

Although the current brain stimulation techniques used to treat neurological disorders have proven to be successful, such techniques are still quite invasive, requiring the cranium to be opened through at least one burr hole. In addition, the need for a burr hole further complicates the procedure—not only requiring the additional step of accessing the patient's cranium while attempting to minimize tissue trauma, but also requiring that the burr hole be capped at the end of the procedure. Also, additional risks are posed by the possibility that the burr hole may become infected and the routing of the stimulation or extension leads through the neck in close proximity to the jugular veins and carotid arteries.

Thus, there remains a need to provide improved methods, apparatus, kits, and systems for therapeutically stimulating tissue.

SUMMARY OF THE INVENTION

In accordance with the present invention, a method of treating a disorder in a patient is provided. The disorder can be any affliction suffered by the patient, such as a degenerative disease or infarction. Because of the minimally invasive nature of the method, the present invention particularly lends itself well to the treatment of neurological disorders, but can be applied to other disorders as well.

The method comprises delivering a stimulation lead within a blood vessel. The lead can take the form of any lead, such as an electrical stimulation lead, that is capable of therapeutically stimulating tissue. In one embodiment, the stimulation comprises an exposed signal wire and an electrode coupled to the exposed wire. In another embodiment, the stimulation lead comprises a catheter having a catheter body, a signal wire extending through the catheter body, and an electrode mounted to the catheter body in electrical contact with the signal wire.

The method further comprises intralumenally puncturing a wall of the blood vessel to create an exit point, and then introducing the stimulation lead through the exit point into direct contact with tissue the stimulation of which treats the disorder. In one preferred method, the vessel wall can be intralumenally punctured by introducing a guide element (e.g., a stylet) through the vessel wall, in which case, the stimulation lead can be conveniently introduced along the guide element (e.g., over the guide element or through a lumen within the guide element) and through the exit point. In this case, a catheter can be introduced into the vessel, the distal end of the catheter deflected towards the vessel wall at an obtuse or perpendicular angle, and the guide element introduced from the deflected distal end of the catheter and through the vessel wall. The catheter may comprise the stimulation lead, in which case, the catheter can then be introduced over the guide element through the exit point in the vessel wall.

To prevent or minimize blood loss, the blood flow upstream from the exit point can be totally or partially occluded and/or the exit point can be sealed after the stimulation lead has been introduced through the exit point. Optionally, the method comprises implanting a source of stimulation within the patient's body, and then electrically coupling the proximal end of the stimulation lead to the implanted stimulation source. Using the stimulation lead, the tissue can then be stimulated in order to treat the disorder.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIGS. 14A-14F are side views illustrating another method of intravascularly delivering stimulation leads into various superior cerebral veins within the brain of a patient using the kit of FIG. 6, wherein the delivery catheter of FIG. 9 is used;

FIG. 17 is a side view of the bipolar arrangement of the system of FIG. 1 arranged in accordance with the schematic diagram of FIG. 5 to stimulate the cortical tissue of a patient's brain;

FIG. 18 is a partially cutaway side view of an alternative embodiment of a delivery catheter that can be used in the kit of FIG. 6;

FIG. 19 is a cross-sectional view of the delivery catheter of FIG. 18, taken along the line 19-19;

FIG. 20 is a partially cutaway side view of another alternative embodiment of a delivery catheter that can be used in the kit of FIG. 6;

FIG. 21 is a cross-sectional view of the delivery catheter of FIG. 20, taken along the line 21-21;

FIG. 22 is a perspective view of another intravascular brain stimulation kit arranged in accordance with a preferred embodiment of the present invention;

FIGS. 23A-23F are side views illustrating a method of intravascularly delivering stimulation leads into the brain of a patient using the kit of FIG. 22;

FIGS. 42A-42D are side views illustrating a method of intravascularly delivering the stimulation lead of FIG. 37 into a cerebral blood vessel of a patient;

DETAILED DESCRIPTION OF THE PREFERRED EMBODIMENTS

Figure 1:
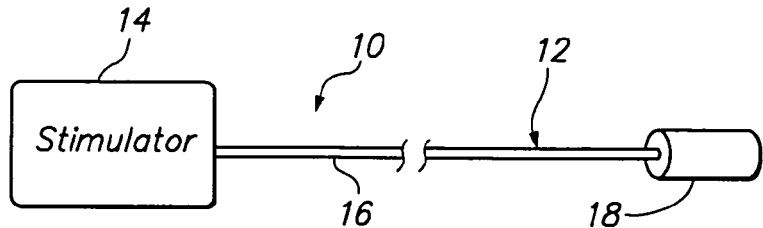
FIG. 1 is a plan view of an intravascular brain stimulation system constructed in accordance with a preferred embodiment of the present invention.

Referring now to FIG. 1, an intravascular brain stimulation system 10 constructed in accordance with one preferred embodiment of the present invention is shown. In its simplest form, the stimulation system 10 generally comprises an electrical stimulation electrode lead 12 configured to be intravascularly implanted within a selected region of a patient's brain, and an implantable electrical stimulation source 14 configured for delivering stimulation energy to the stimulation lead 12.

The stimulation electrode lead 12 comprises a flexible electrically conductive wire 16 and a single electrode 18 mounted at the distal end of the wire 16 using suitable connection means, such as soldering or welding. In the illustrated embodiment, the electrode 18 is cylindrically shaped and has a size that allows it to be delivered through a delivery catheter, as will be described in further detail below. The wire 16 comprises an electrically conductive core with an outer insulative layer. The length of the wire 16 is preferably sized to extend from the selected stimulation site in the brain to the implant location of the stimulation source 14. For example, if the stimulation source 14 is to be implanted in the chest region of the patient, the length of the wire 16 may be in the range of 50 cm to 100 cm. If, however, the stimulation source 14 is to be implanted in the abdomen or groin area of the patient, the length of the wire 16 may be in the range of 150 cm to 300 cm. The electrode 18 is composed of a biocompatible and electrically conducting material, such as copper alloy, platinum, stainless steel, or nitinol. The electrically conducting material of the electrode 18 can be further coated with platinum-iridium or gold to improve its conduction properties, biocompatibility, and radiopacity. To prevent blood clotting, the electrode lead 12 can be optionally coated with a non-thrombogenic agent.

Figure 2:
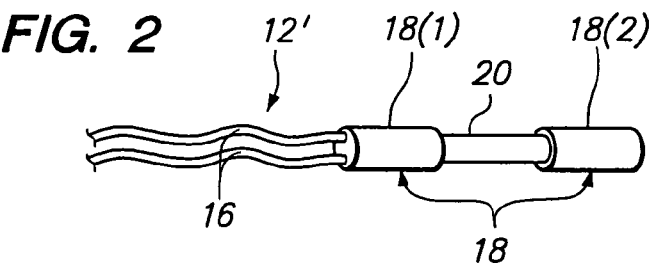
FIG. 2 is a perspective view of an alternative embodiment of a stimulation lead that can be used in the system of FIG. 1.

Referring to FIG. 2, an alternative embodiment of a stimulation electrode lead 12' is shown. The stimulation lead 12' is similar to the previously described stimulation lead 12, with the exception that it comprises a pair of electrodes 18 (a proximal electrode 18(1) and a distal electrode 18(2)) and a pair of signal wires 16 respectively coupled to the pair of electrodes 18. The electrode pair 18 can be suitably formed, e.g., by mounting a pair of ring electrodes around an electrically insulative cylindrical core 20, or by coating the cylindrical core 20 with electrically conductive material. The signal wires 16 extend through the cylindrical core 20 into contact with the respective electrodes 18(1) and 18(2). Thus, it can be appreciated that the stimulation lead 12', by itself, can be operated in a bipolar mode. This is in contrast to the stimulation lead 12, which can be operated in a monopolar mode, or alternatively, can be operated in a bipolar mode in conjunction with another stimulation lead 12, as will be described in further detail below.

Referring back to FIG. 1, the implantable stimulation source 14 is designed to deliver electrical pulses to the stimulation lead 12 in accordance with programmed parameters. In the preferred embodiment, the stimulation source 14 is programmed to output electrical pulses having amplitudes varying from 0.1 to 20 volts, pulse widths varying from 0.02 to 1.5 milliseconds, and repetition rates varying from 2 to 2500 Hertz. In the illustrated embodiment, the stimulation source 14 takes the form of a totally self-contained generator, which once implanted, may be activated and controlled by an outside telemetry source, e.g., a small magnet. In this case, the pulse generator has an internal power source that limits the life of the pulse generator to a few years, and after the power source is expended, the pulse generator must be replaced. Generally, these types of stimulation sources 14 may be implanted within the chest or abdominal region beneath the skin of the patient. Alternatively, the implantable stimulation source 14 may take the form of a passive receiver that receives radio frequency (RF) signals from an external transmitter worn by the patient. In this scenario, the life of the stimulation source 14 is virtually unlimited, since the stimulation signals originate from the external transmitter. Like the self-contained generators, the receivers of these types of stimulation sources 14 can be implanted within the chest or abdominal region beneath the skin of the patient. The receivers may also be suitable for implantation behind the ear of the patient, in which case, the external transmitter may be worn on the ear of the patient in a manner similar to that of a hearing aid. Stimulation sources, such as those just described, are commercially available from Medtronic, Inc., located in Minneapolis, Minn. Further details regarding the construction of a stimulation source for the purpose of treating neurological disorders is disclosed in U.S. Pat. No. 5,716,377, which is expressly incorporated herein by reference.

In optional embodiments, the stimulation source 14 provides automated feedback for recording and stimulation to control such neurological disorders as Epileptic seizures. Further details on the use of feedback to control Epileptic seizures and other disorders are disclosed in U.S. Pat. No. 5,716,377, which has previously been incorporated herein by reference, and U.S. Pat. No. 6,360,122, which is expressly incorporated herein by reference.

Figure 3:
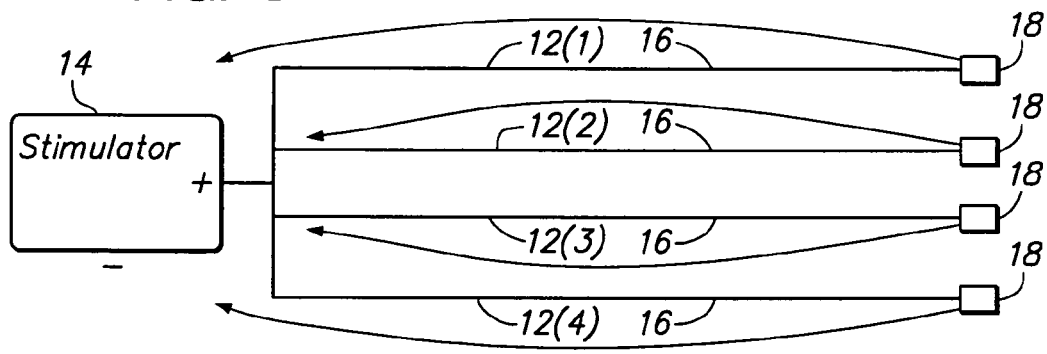
FIG. 3 is a schematic diagram of the system of FIG. 1 in a monopolar arrangement.
Figure 4:
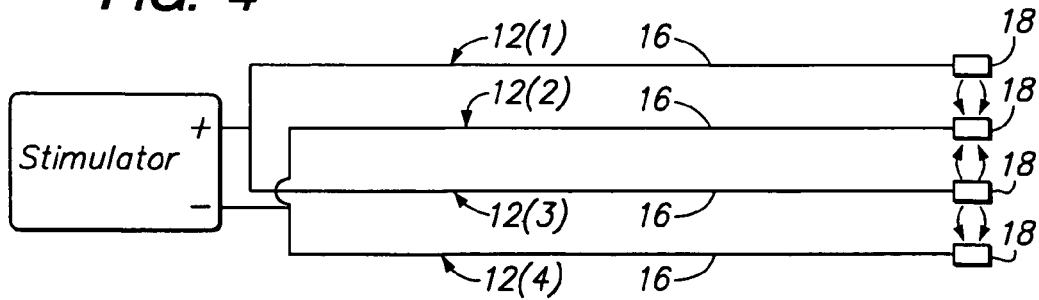
FIG. 4 is a schematic diagram of the system of FIG. 1 in a bipolar arrangement.
Figure 5:
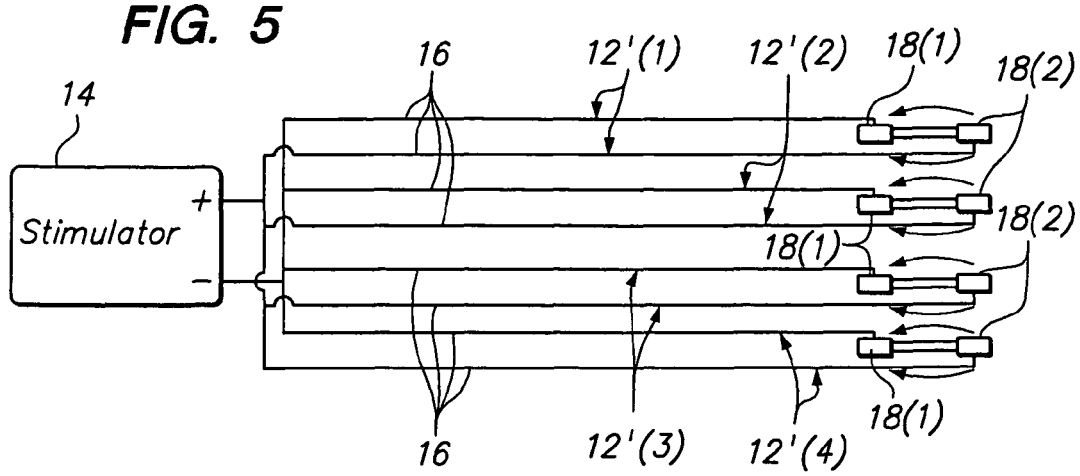
FIG. 5 is a schematic diagram of the system of FIG. 1 in another bipolar arrangement.

As illustrated in FIGS. 3-5, the electrical path of the stimulation signals generated by the stimulation system 10 will depend on the manner in which the stimulation source 14 is connected to the signal wires 16 of the stimulation leads 12. For example, FIG. 3 illustrates a four-channel monopolar arrangement, wherein the positive terminal of the stimulation source 14 is coupled in parallel to signal wires 16 of four stimulation leads 12(1)-(4). In this case, the electrical stimulation signals will travel from the four electrodes 18 located on the respective stimulation leads 12, through the brain tissue, and back to the electrically conductive casing of the stimulation source 14 remotely implanted in the patient's body.

FIG. 4 illustrates a bipolar arrangement, wherein the positive terminal of the stimulation source 14 is coupled in parallel to the signal wires 16 of the first and third stimulation leads 12(1) and 12(3), and the negative terminal of the stimulation source 14 is coupled in parallel to the signal wires 16 of the second and fourth stimulation leads 12(2) and 12(4). In this case, the electrical stimulation signals will travel from the electrode 18 of the first stimulation lead 12(1), through the brain tissue, to the electrode 18 of the second stimulation lead 12(2), and from the third stimulation lead 12(2), through the brain tissue, to the electrodes 18 of the second and fourth stimulation leads 12(2) and 12(4).

FIG. 5 illustrates a four-channel bipolar arrangement, wherein the positive terminal of the stimulation source is coupled in parallel to the distal electrodes 18(2) of the four stimulation leads 12'(1)-12'(4), and the negative terminal of the stimulation source is coupled in parallel to the proximal electrodes 18(1) on the respective stimulation leads 12'(1)-12'(4). In this case, the electrical stimulation signals will travel from the distal electrodes 18(2) of the respective stimulation leads 12'(1)-12'(4), through the brain tissue, to the respective proximal electrodes 18(1) located on the same stimulation leads 12'(1)-12'(4).

Figure 6:
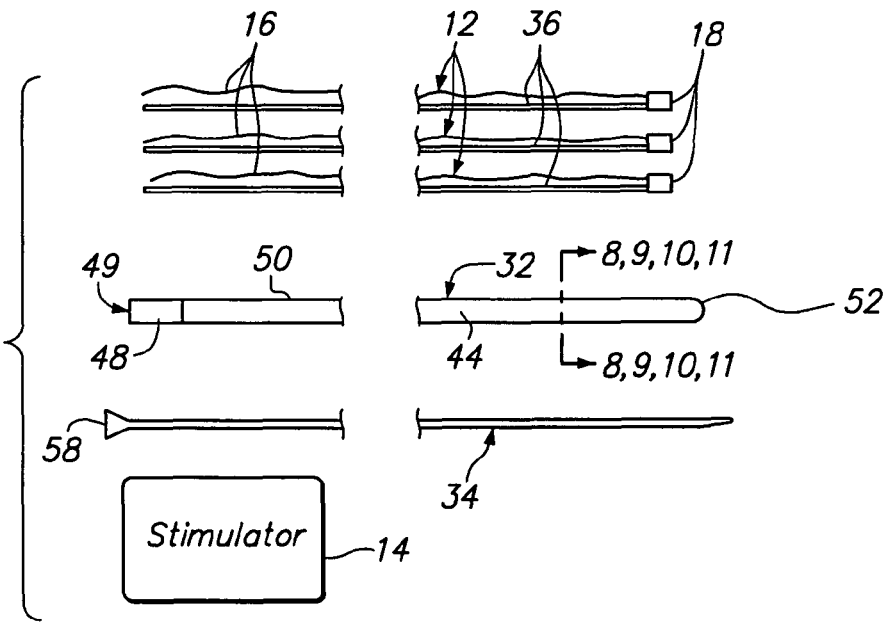
FIG. 6 is a plan view of an intravascular brain stimulation kit arranged in accordance with a preferred embodiment of the present invention.

Referring now to FIG. 6, an intravascular brain stimulation kit 30 arranged in accordance with one preferred embodiment of the present invention is illustrated. The brain stimulation kit 30 comprises a plurality of the previously described electrical stimulation electrode leads 12 (or stimulation electrode leads 12') and implantable electrical stimulation source 14, a delivery catheter 32 configured for intravascularly delivering the electrical stimulation leads 12 into selected blood vessels within the patient's brain, a guidewire 34 configured for guiding the delivery catheter 32 into the selected blood vessels, and detachable pusher elements 36 configured for deploying the stimulation leads 12 from the delivery catheter 32 into selected regions within the blood vessels.

Each pusher element 36 is mechanically coupled to the electrode 18 on the respective stimulation lead 12. The pusher element 36 is axially rigid, so that the electrode 18 can be introduced through the catheter 32, yet laterally flexible to allow the pusher element 36 to bend around the natural curves within the patient's vasculature. In the illustrated embodiment, the pusher element 36 can be selectively detached from the electrode 18 (once properly placed) using an electrolytic arrangement.

Figure 7:
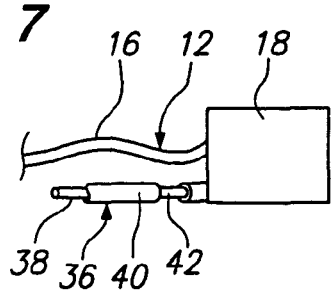
FIG. 7 is a close-up view of a stimulation lead with an electrolytically detachable pusher element used in the kit of FIG. 6.

In particular, as illustrated in FIG. 7, the pusher element 36 comprises an electrically conductive core wire 38 composed of a material that will electrolytically dissolve in an aqueous fluid medium, such as blood, saline solution, or other bodily fluid. Materials that are capable of electrolytically dissolving are steel, stainless steel, nickel, and nickel/titanium alloys. The electrode 18 may be suitably coupled to the distal end of the core wire 38 using means, such as crimping, soldering, or welding. The pusher element 36 further comprises an insulative sleeve 40 that, with the exception of a small sacrificial portion 42 just proximal to the mounted electrode 18, covers the core wire 38. The length of the sacrificial portion 42 is preferably small. For instance, it may be as short as 0.010 inches, and typically no longer than 0.150 inches in length. The insulative sleeve 40 is composed of a material that will not decompose prior to the sacrificial portion 42 of the core wire 38. For example, the insulative sleeve 40 may be composed of polytetrafluoroethylene, fluoropolymers, polyurethane, parylene, polyethylene, polypropylene, polyethylene terephthalate, or other known suitable, typically polymeric, material. Thus, it can be appreciated that when electrical current is delivered through the core wire 38, while the distal end of the pusher element 36 is exposed to blood, the sacrificial portion 42 of the core wire 38 will disintegrate, thereby releasing the electrode 18. Additional details regarding the use of pusher wires with electrolytic detachment means are disclosed in U.S. Pat. No. 6,589,230, which is expressly incorporated herein by reference.

In alternative embodiments, pusher wires with mechanical detachment mechanisms can be used to selectively detach the electrode 18. For example, U.S. Pat. Nos. 5,234,437, 5,250,071, 5,261,916, 5,304,195, 5,312,415, and 5,350,397, which are expressly incorporated herein by reference, disclose such mechanically detachable means.

Figure 8:
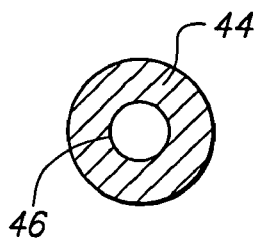
FIG. 8 is a cross-sectional view of one preferred embodiment of a delivery catheter used in the kit of FIG. 6, taken along the line 8-8.

Referring back to FIG. 6, the delivery catheter 32 comprises an elongate, flexible, catheter body 44 and a guidewire lumen 46 (shown in FIG. 8) extending the length of the catheter body 44. The guidewire lumen 46 is configured to singly receive the guidewire 34 and stimulation electrode lead 12. The delivery catheter 32 further comprises a proximal adapter 48 suitably mounted on the proximal end of the catheter body 44. The proximal adapter 48 comprises a guidewire port 49 out which the guidewire 34 may extend when the delivery catheter 32 is introduced over the guidewire 34. The guidewire port 49 also serves as a port through which the stimulation leads 12 can be introduced through the delivery catheter 32.

The catheter body 44 is composed of a medically acceptable material, preferably a nondistensible polymer having the appropriate mechanical properties. Preferred materials include polyethylene, polyester, polypropylene, polyimide, polyvinyl chloride, ethylvinyl acetate, polyethylene terephthalate, polyurethane, PEBAX, fluoropolymers, and their mixtures and block or random copolymers. The catheter body 32 preferably has a relatively stiff proximal segment 50, which makes up between 70%-95% of the total length of the catheter body 44, and a relatively flexible distal segment 52, which makes up the remaining 5%-30% of the length of the catheter body 44.

The guidewire lumen 46 of the catheter 32 preferably has a diameter of between 2-50 mils, but ultimately will be sized to allow the electrode 18 and guidewire 34 to be introduced therethrough. The outer diameter of the catheter body 44 is preferably between 8-80 mils, but ultimately will be sized such that blood flow is not occluded within the smallest blood vessel through which the delivery catheter 32 will be introduced. For example, the vessel site may be within a small diameter vessel having a 2-5 mm diameter and accessible by way of a tortuous vessel path, which may involve sharp vessel turns and multiple vessel branches. In this case, the catheter 32 preferably has a small, flexible construction with a diameter of less than 40 mil, and preferably between 8-30 mils. The length of the catheter body 44 will typically be from 50-300 cm, depending on the total linear length of the blood vessels that the delivery catheter 32 must traverse from its entry point into the patient's vasculature to the intended delivery site of the electrode 18.

Preferably, the guidewire lumen 46 of the delivery catheter 32 is large enough to simultaneously fit the guidewire 34 and the multiple signal wires 16 from the stimulation leads 12. In this manner, a multitude of the stimulation leads 12 can be delivered to selected region in the brain without having to completely remove the delivery catheter 32 from the patient's vasculature, as will be described in further detail below.

Figure 9:
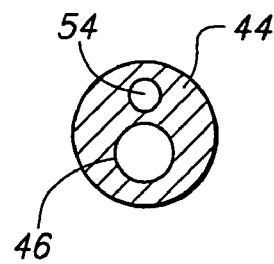
FIG. 9 is a cross-sectional view of another preferred embodiment of a delivery catheter used in the kit of FIG. 6, taken along the line 9-9.

Alternatively, as illustrated in FIG. 9, the delivery catheter 32 has a dedicated stimulation lead delivery lumen 54. This delivery lumen 54 is preferably sized to fit an electrode 18, so that multiple stimulation leads 12 can be delivered by sequentially introducing the stimulation leads 12 through the dedicated delivery lumen 54. To facilitate separate introduction of a stimulation lead 12 through the delivery catheter 32, the proximal adapter 48, in addition to having a guidewire port 49, has a separate signal wire port (not shown).

Figure 10:
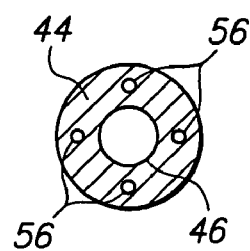
FIG. 10 is a cross-sectional view of still another preferred embodiment of a delivery catheter used in the kit of FIG. 6, taken along the line 10-10.

Alternatively, as illustrated in FIG. 10, the delivery catheter 32 can have multiple dedicated stimulation lead delivery lumens 56. Again, the delivery lumens 56 are preferably sized to fit the respective electrodes 18. In this case, the multiple stimulation leads 12 can be sequentially deployed from the respective delivery lumens 56 without mechanically interfering with each other. To facilitate separate introduction of the stimulation leads 12 through the delivery catheter 32, the proximal adapter 48, in addition to having a guidewire port 49, has an equal number of separate signal wire ports (not shown).

Figure 11:
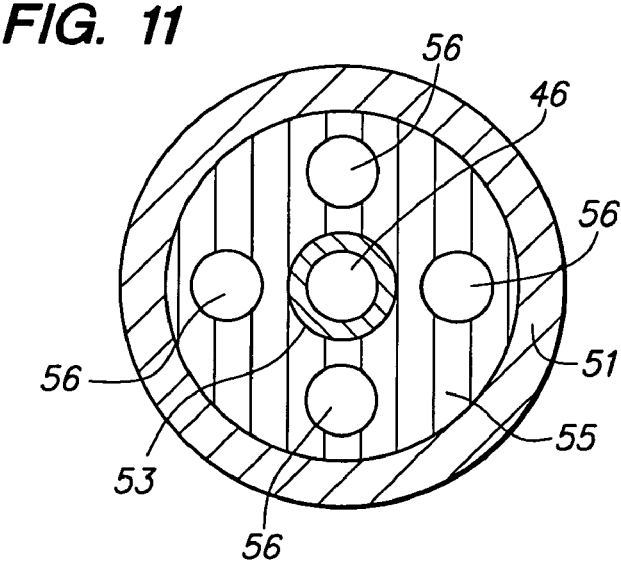
FIG. 11 is a cross-sectional view of yet another preferred embodiment of a delivery catheter used in the kit of FIG. 6, taken along the line 11-11.
Figure 12:
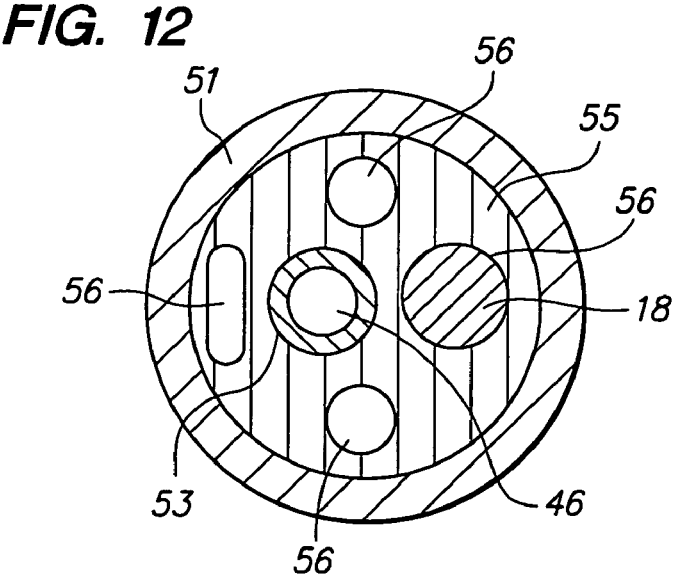
FIG. 12 is a cross-sectional view of the delivery catheter of FIG. 11, wherein an electrode is particularly shown passing through one of the stimulation lead delivery lumens.

Alternatively, as illustrated in FIGS. 11 and 12, the delivery catheter 32 can have multiple dedicated stimulation lead delivery lumens 56 that distort, so that the diameter of the delivery catheter 32 can be reduced. In particular, the delivery catheter 32 comprises outer tube 51 composed of a suitable non-compliant material, and an inner tube 53, which forms the guidewire lumen 46 and is composed of a similar non-compliant material. The delivery catheter 32 further comprises a cylindrical body 55 formed between the outer and inner tubes 51 and 53. The cylindrical body 55 is composed of a suitable compliant material, such as silicone. The delivery lumens 56 are formed through the cylindrical body 55, such that the delivery lumens 56 will expand in the presence of a radially outward force and contract in the presence of a radially inward force.

In this manner, the lumens 56 can be dimensioned smaller than the electrodes 18 of the stimulation leads 12, thus minimizing the diameter of the catheter 32. Because the lumens 56 are capable of expanding in the presence of an outward radial force, however, a lumen 56 will expand to accommodate an electrode 18 as it is delivered through the lumen 56. At the same time, the inner tube 53 will be displaced away from the expanded lumen 56, thereby creating inwardly radial pressure on the lumen 56 opposite the expanding lumen 56, as illustrated in FIG. 12. As a result, the opposite lumen 56, which does not house an electrode 18 at this time, will distort in the presence of the radial force exerted by the inner tube 53. Thus, the distortion of a delivery lumen 56 will compensate for the expansion of the oppositely disposed delivery lumen 56, and vice versa.

Referring back to FIG. 6, the guidewire 34 may have any suitable construction for guiding the delivery catheter 32 to its intended site in the brain. Typically, the length of the guidewire 34 is at least about 10-50 cm longer than the length of the catheter 32, such that the distal end of the guidewire 34 can be extended several centimeters or more beyond the distal end of the delivery catheter 32, while allowing the proximal end of the guidewire 34 to be manipulated, such as by torqueing. The proximal end of the guidewire 34 is equipped with a handle 58 for applying torque to the wire during catheter operation. The guidewire 34 may optionally include radio-opaque bands (not shown) for visualization under fluoroscopy. Additional details regarding the structure and dimensions of guidewires suitable for guiding catheters into the vasculature of the brain are disclosed in U.S. Pat. No. 6,074,507, which is expressly incorporated herein by reference.

Having described the structure of the intravascular brain stimulation kit 30, a preferred method of installing the intravascular brain stimulation system 10 within a patient's body in order to treat a diagnosed neurological disorder within the brain will now be described.

The routing and placement of the brain stimulation system 10 will ultimately depend on the portion of the brain that is to be treated. For example, the cortex of the brain or the deep brain can be electrically stimulated to provide post-stroke rehabilitation (from hemorrhagic stroke, ischemic stroke or head/brain trauma), Parkinson's Disease, Essential Tremor, Huntington's Disease, Alzheimer's Disease, Epilepsy, depression, obsessive compulsive disorder, schizophrenia, and neuropathic pain. Any lobe of the cortex or deep brain can be stimulated. Preferably, for the cortical region of the brain, the motor strip, sensor strip, and premotor cortex should be stimulated. For the deep brain region, the anterior thalamus, ventrolateral thalamus (Thal), internal segment of globus pallidus (GPi), substantia nigra pars reticulata (SNr), subthalamic nucleus (STN), external segment of globus pallidus (GPe), neostriatum, cingulate, and cingulate gyrus should be stimulated.

The spheno palatine ganglion (SPG), which can control the amount of blood flow to the brain and the permeability of the blood brain barrier, may also be stimulated, e.g., to hyperperfuse a hemisphere of the brain damaged as a result of an ischemic event, such as a stroke, or to help metabolize amlyoid plaques caused by Alzheimer's Disease and prevent the occurrence of vaso-spasms, both achieved through increased blood flow to the brain. Lastly, the SPG can be stimulated to facilitate the opening of the blood-brain barrier, enabling better uptake of drugs to the brain. These drugs could be delivered in a variety of methods (e.g. orally, intravenously, or via direct injection into the penumbra) and could be used to treat a variety of neurologically related maladies (stroke, epilepsy, Parkinson's, tumors, essential tremor, Alzheimer's, etc.).

A stimulation lead can be delivered to any one of a number of vessels in order to place the active portion of the stimulation lead adjacent the cortical tissue to be stimulated. Examples of veins providing access to the cortex include the superior sagittal sinus, any of the superior cerebral veins branching from the superior sagittal sinus (e.g., the lacuna, frontopolar vein, anterior frontal vein, posterior frontal vein, precentral vein, central vein, anterior parietal vein, posterior parietal vein, and occipital vein), superior sylvian vein, vein of Labbe, vein of Trolard, inferior sagittal sinus, and any inferior cerebral veins branching off of the inferior sagittal sinus, transverse sinus, and meningeal sinus. Examples of arteries providing access to the cortex include any of the branches off of the external carotid, maxillary, or meningeal arteries.

Examples of veins providing access to the deep brain include the inferior sagittal sinus, pericallosal sinus, cavernous sinus, sphenoid sinus, temperal basal vein, and occipital veins. Examples of arteries providing access to the deep brain include any branches off of the internal carotid or vertebral arteries. Examples of veins providing access to the SPG include the superficial temporal veins and the facial vein. Examples of arteries providing access to the SPG include the maxillary artery, descending palatine artery, and facial artery.

The jugular and femoral veins can be used as intrasvascular access points from which stimulation leads can be delivered to the above-described veins, and the carotid or femoral arteries can be used as intravascular access points from which the stimulation leads can be delivered to the above-described arteries.

Figure 13A:
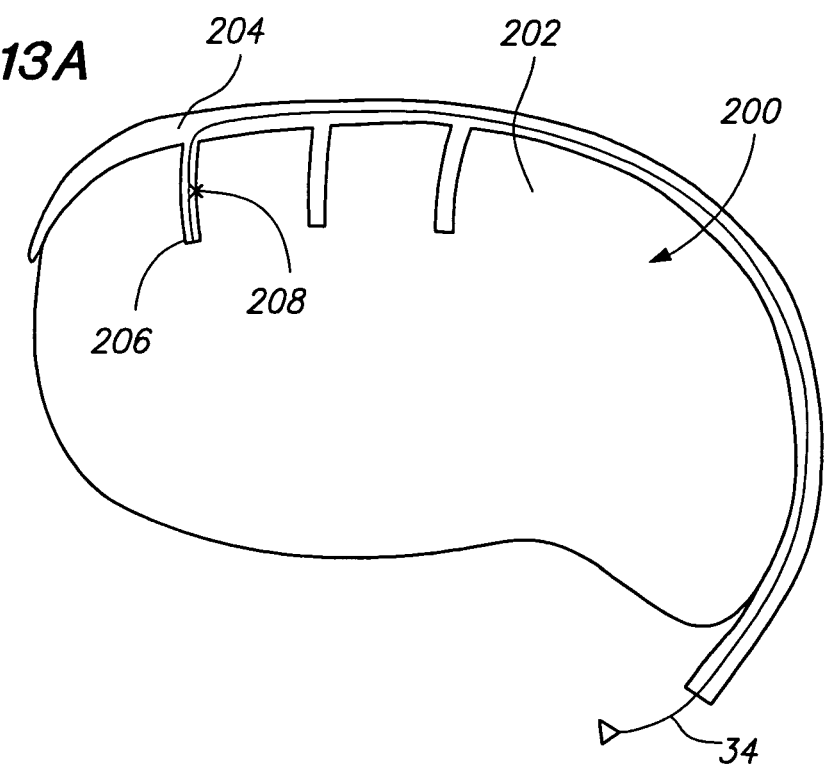
FIGS. 13A-13G are side views illustrating a method of intravascularly delivering stimulation leads into various superior cerebral veins within the brain of a patient using the kit of FIG. 6, wherein the delivery catheter of FIG. 8 is used.

With reference now to FIGS. 13A-13H, an exemplary method used to deliver stimulation leads 12 to the superior cerebral veins 206 branching off of the superior sagittal sinus 204, which runs along the top of the cortex 202, will now be described. First, from a remote access site, such as the inner jugular vein or femoral vein (not shown), the guidewire 34 is routed through the superior sagittal sinus 204 and into a selected superior cerebral vein 206 until the distal end of the guidewire 34 extends past a selected stimulation site 208 (FIG. 13A). To facilitate the correct routing and placement of the guidewire 34, diagnostic imaging, such as fluoroscopy, magnetic resonance imaging (MRI), and computer tomography (CT), is preferably used to track the distal end of the guidewire 34. As will be described in further detail below, the access site into the vasculature will ultimately depend on the selected implantation site of the stimulation source 14. For example, if the stimulation source 14 is to be implanted within the chest or clavical region, or behind the ear, of the patient, the jugular vein should be selected as the access point. If, on the other hand, the stimulation source 14 is to be implanted within the abdominal or groin region of the patient, the femoral vein should be selected as the access point.

Figure 13B:
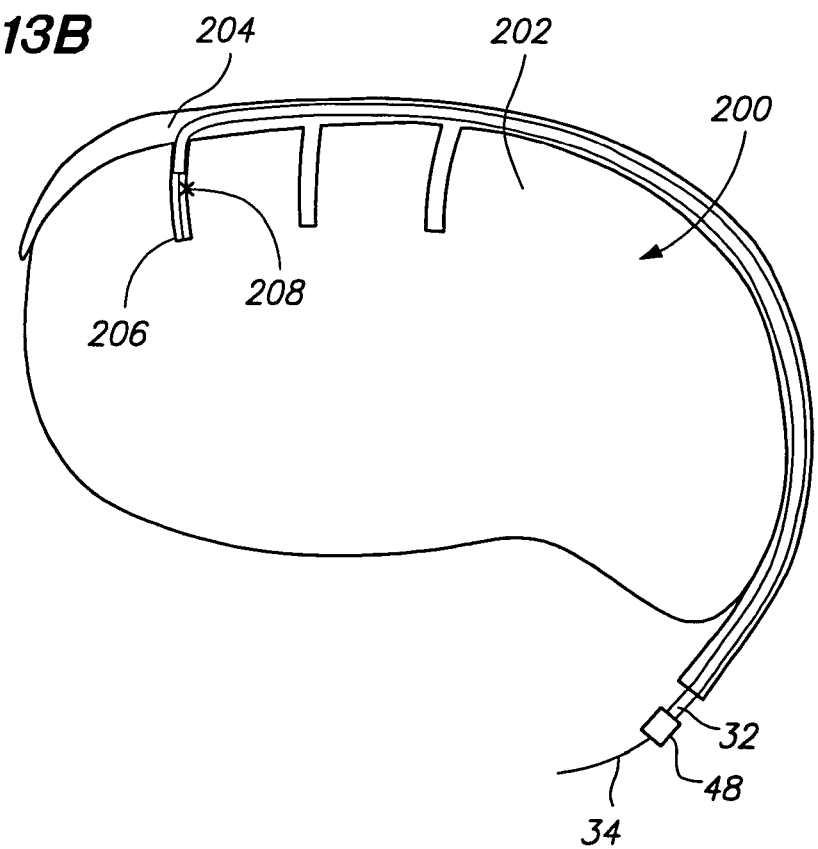
Figure 13C:
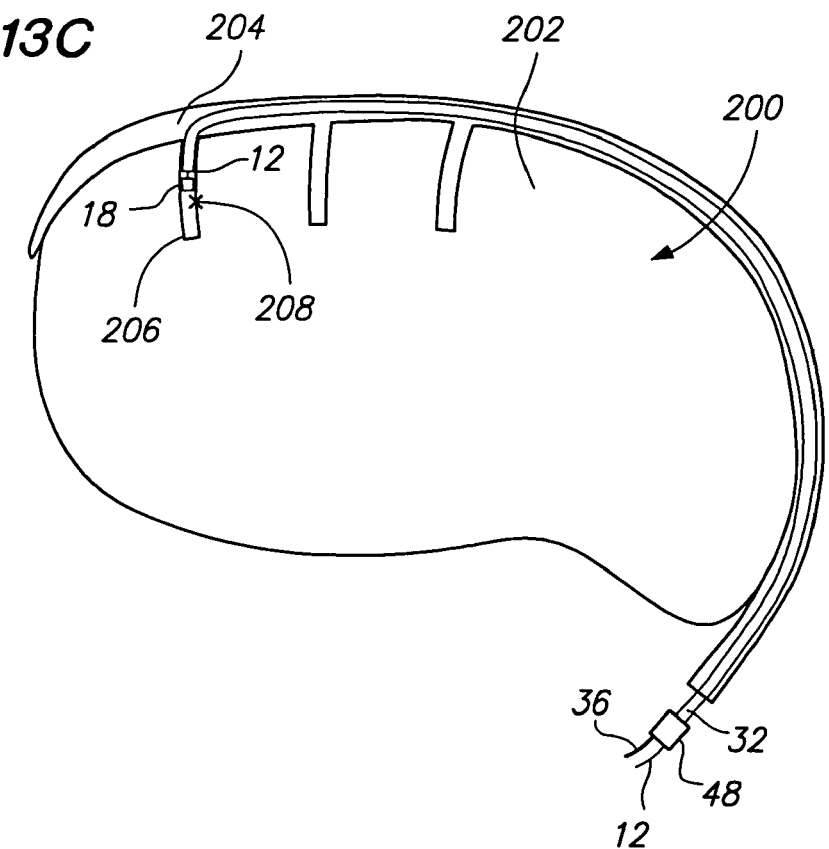
Figure 13D:
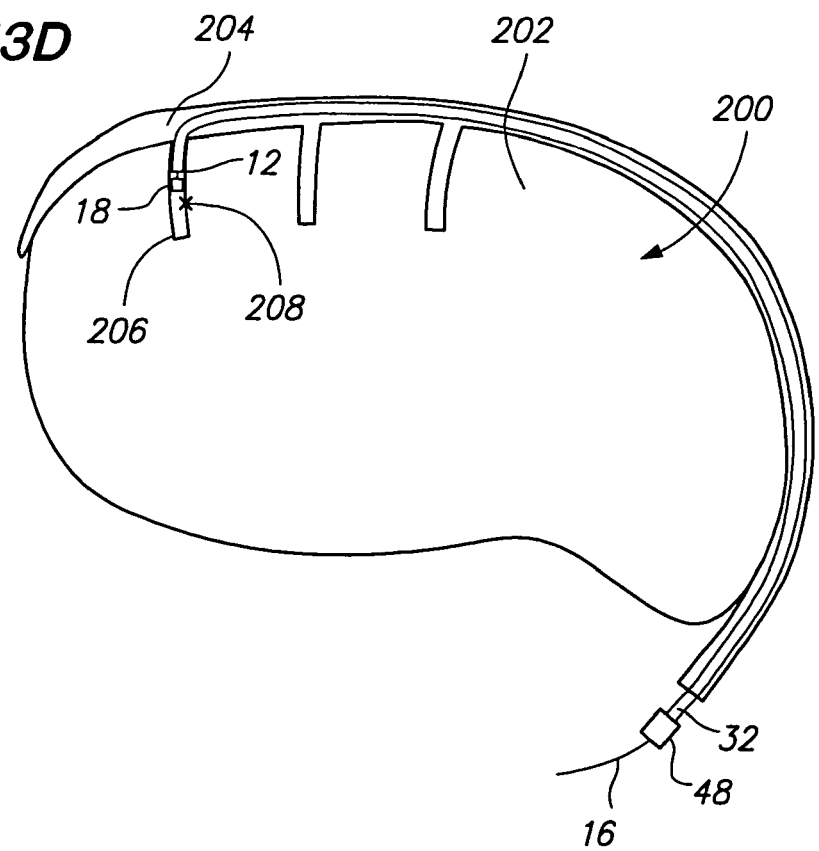

Next, the delivery catheter 32 is introduced over the guidewire 34 until the distal end of the catheter 32 is just proximal to the selected stimulation site 208 (FIG. 13B). Once proper placement of the catheter 32 is achieved, the guidewire 34 is removed from guidewire lumen 46 via the proximal adapter 48 of the delivery catheter 32, and the stimulation lead 12 and associated pusher element 36 are inserted into the delivery catheter 32 via the proximal adapter 48, and then distally advanced through the delivery catheter 32 until the distal end of the stimulation lead 12 deploys out from the distal end of the catheter 32 adjacent the selected stimulation site 208 (FIG. 13C). Next, the pusher element 36 is electrolytically detached from the electrode 18 and removed from the delivery catheter 32 via the proximal adapter 48 (FIG. 13D). As previously discussed, detachment of the pusher element 36 can be accomplished by applying an electrical current to the proximal end of the core wire 16, which as previously described above, causes the sacrificial joint 42 (shown in FIG. 7) on the core wire 38 to dissolve in the presence of blood.

Figure 13E:
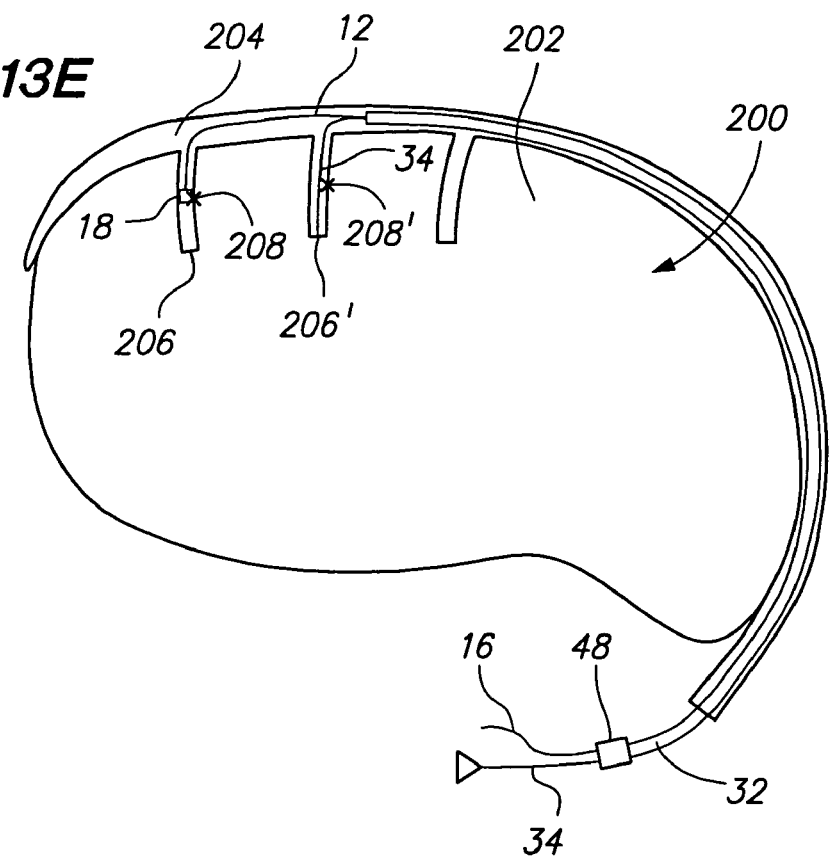

Assuming that additional stimulation leads 12 are to be placed within the brain 200, the delivery catheter 32 can be pulled back in the proximal direction until its distal end resides within the superior sagittal sinus 204, and the guidewire 34 can then be introduced through the delivery catheter 32 via the proximal adapter 48, and manipulated into another superior cerebral vein 206', such that the distal end of the guidewire 34 is located distal to another selected stimulation site 208' (FIG. 13E). Notably, the signal wire 16 of the first stimulation lead 12 will still be located within the guidewire lumen 46 during advancement of the guidewire 34 therethrough, and thus, the profile of the signal wire 16 should be small enough, such that the guidewire 34 and the signal wire 16, as well as subsequent signals wire 16, can simultaneously reside within the guidewire lumen 46. It should be noted that it is possible for the first stimulation lead 12 to move when the delivery catheter 32 is pulled back in the proximal direction. In this case, it may be desirable to detach the pusher element 36 from the first electrode 18 after the delivery catheter 32 has been pulled back. In this manner, the pusher element 36 can be used to stabilize the electrode 18 while the delivery catheter 36 is displaced.

Alternatively, prior to reintroduction of the guidewire 34, the catheter 32 can be completely removed from the patient's vascularly, while maintaining the electrode 18 within the selected superior cerebral brain. The catheter 32 can then be reinserted into the patient's vascular, and then the guidewire 34 can be introduced through the guidewire lumen 46, so that the distal end of the guidewire 34 resides within a location distal to the other stimulation site 208.

Figure 13F:
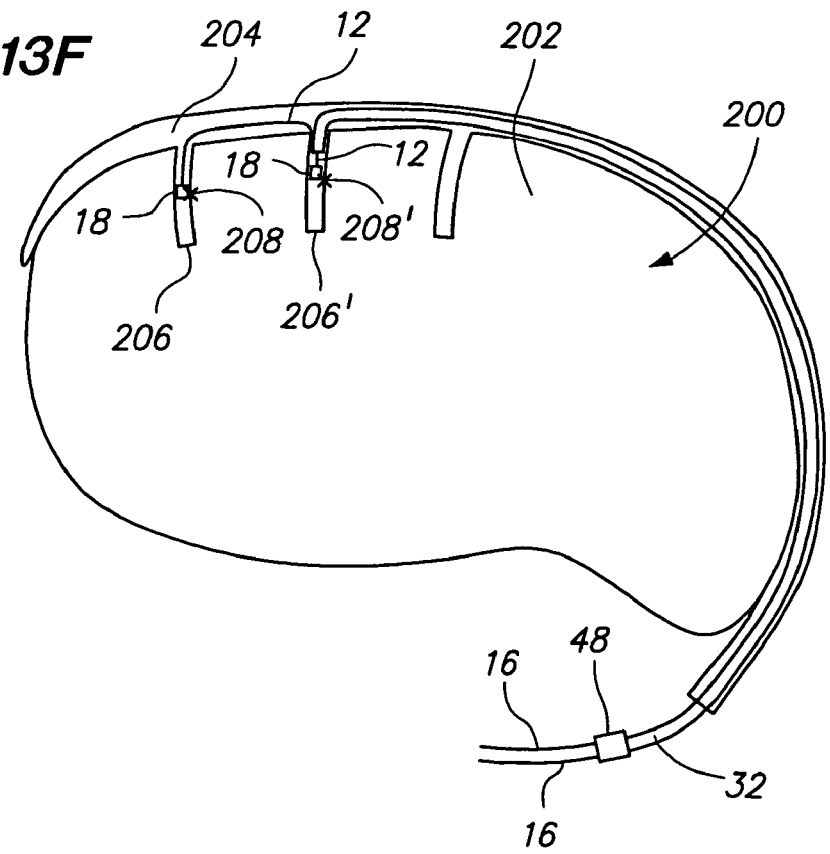
Figure 13G:
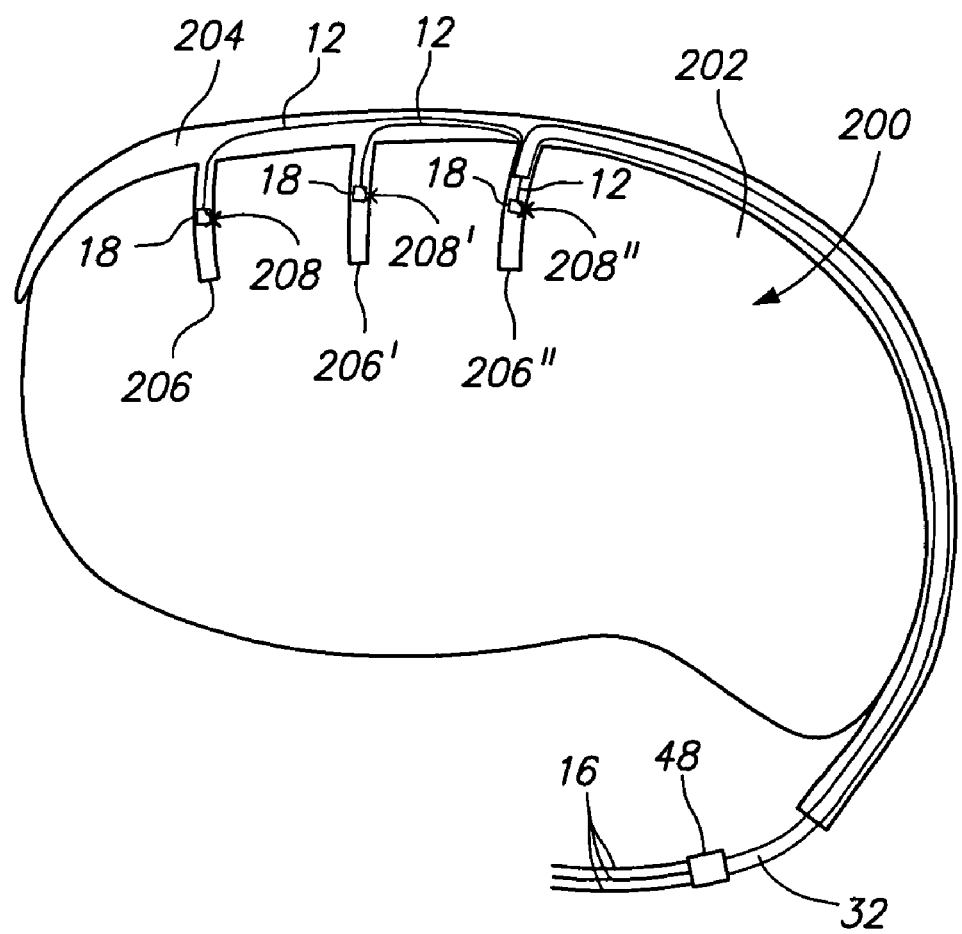

In any event, the delivery catheter 32 is then advanced over the guidewire 34 until the distal end of the catheter 32 is placed adjacent the other selected stimulation site 208', the guidewire 34 is removed from the delivery catheter 32, another stimulation lead 12 with another pusher element 36 is advanced through the guidewire lumen 46 until the electrode 18 is adjacent the other selected stimulation site 208, and the pusher element 36 is then detached from the electrode 18 by applying an electrical current to the proximal end of the core wire 16 (FIG. 13F). The steps illustrated in FIGS. 13E-13F can then be repeated if additional stimulation leads 12 are to be placed within the brain 200. In the illustrated case, a total of three stimulation leads 12 are implanted adjacent the stimulation sites 208, 208', 208'' within the superior veins 206, 206' 206'' branching from the superior sagittal sinus 204 (FIG. 13G). After all of the stimulation leads 12 have been deployed within the brain 200, the delivery catheter 32 is removed from the superior sagittal sinus 204. It can be appreciated from the foregoing process that if the placement of multiple stimulation leads 12 within the brain 200 is desired, the most distal stimulation leads 12 should be placed first in order to minimize disturbance of the stimulation leads 12 as the delivery catheter 32 is pulled in the proximal direction.

Depending on the nature of the neurological disorder and goals of the operation, the stimulation leads 12 may be left within the brain either acutely (i.e., only during an operation and then removed after the operation has been completed), chronically, or sub-chronically (i.e., less than six months).

Figure 14A:
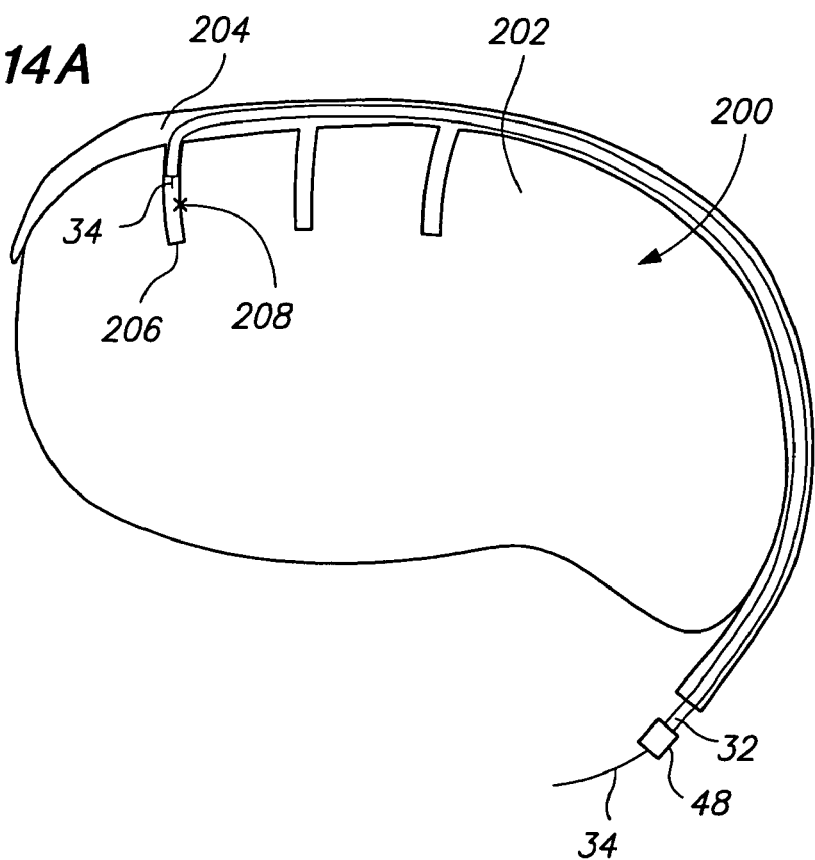
Figure 14B:
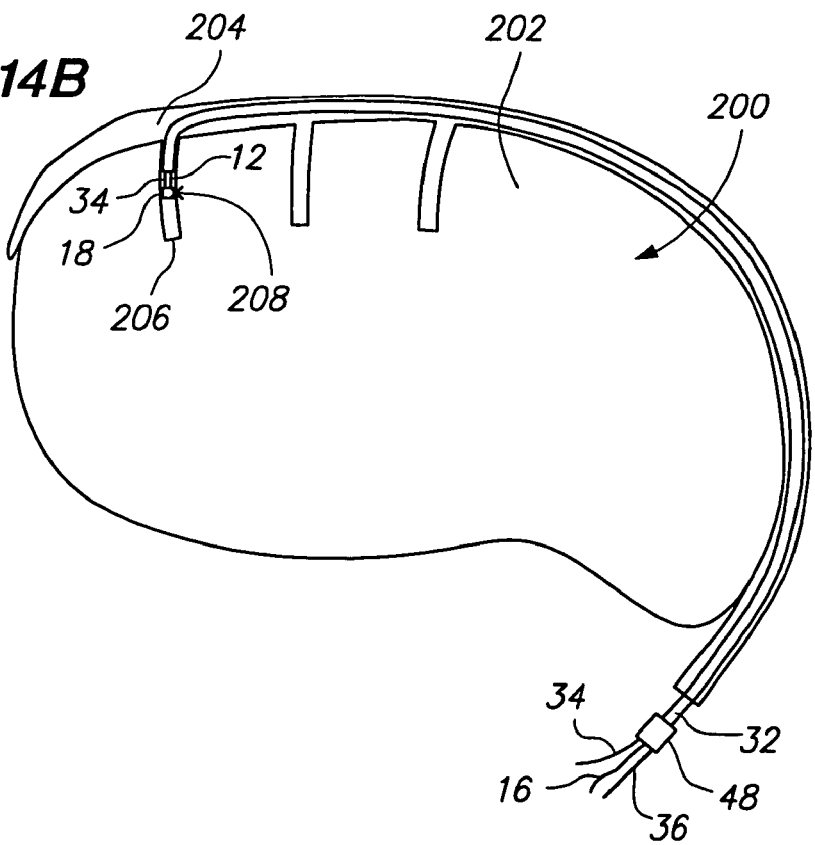
Figure 14C:
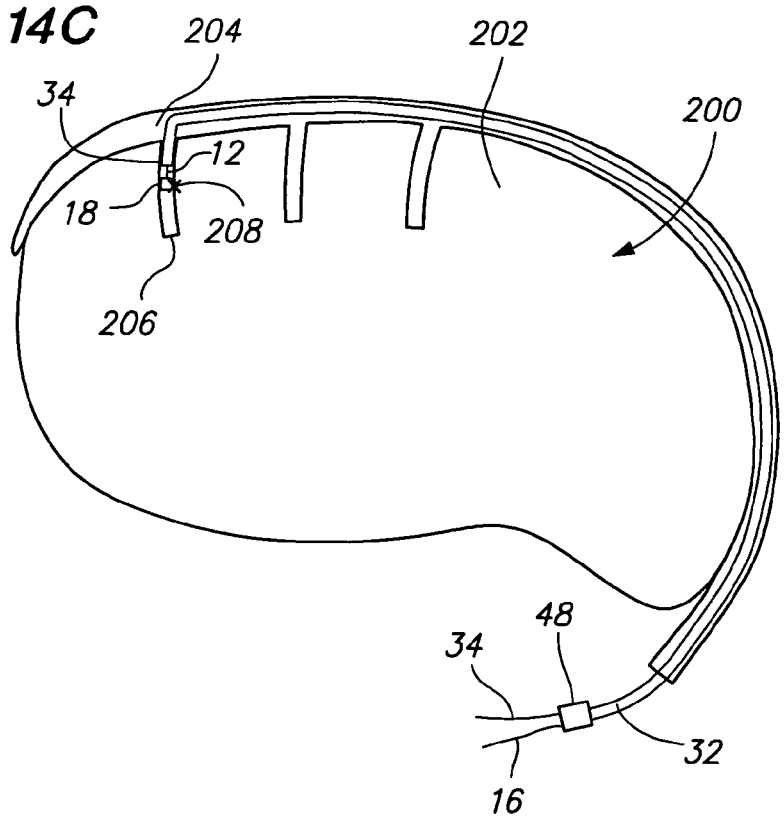

In an alternative method, the delivery catheter 32 illustrated in FIG. 9 can be used. In this case, after the distal end of the delivery catheter 32 has been placed proximal to the selected stimulation site 208, in the manner illustrated in FIG. 13B, the guidewire 34 is retracted to a position proximal to the selected stimulation site 208 to provide clearance for deployment of the stimulation lead 12 (FIG. 14A). Notably, since the guidewire lumen 46 need not be capable of additionally accommodating stimulation leads 12, the guidewire 34 will not need to be removed from the delivery catheter 32 as otherwise illustrated in FIG. 13C. Next, the stimulation lead 12 is distally advanced through the dedicated delivery lumen 54 (shown in FIG. 9) of the catheter 32 until the distal end of the stimulation lead 12 deploys out from the distal end of the catheter 32 adjacent the selected stimulation site 208 (FIG. 14B). Next, the pusher element 36 is detached from the electrode 18 and removed from the delivery catheter 32 via the proximal adapter 48 (FIG. 14C).

Figure 14D:
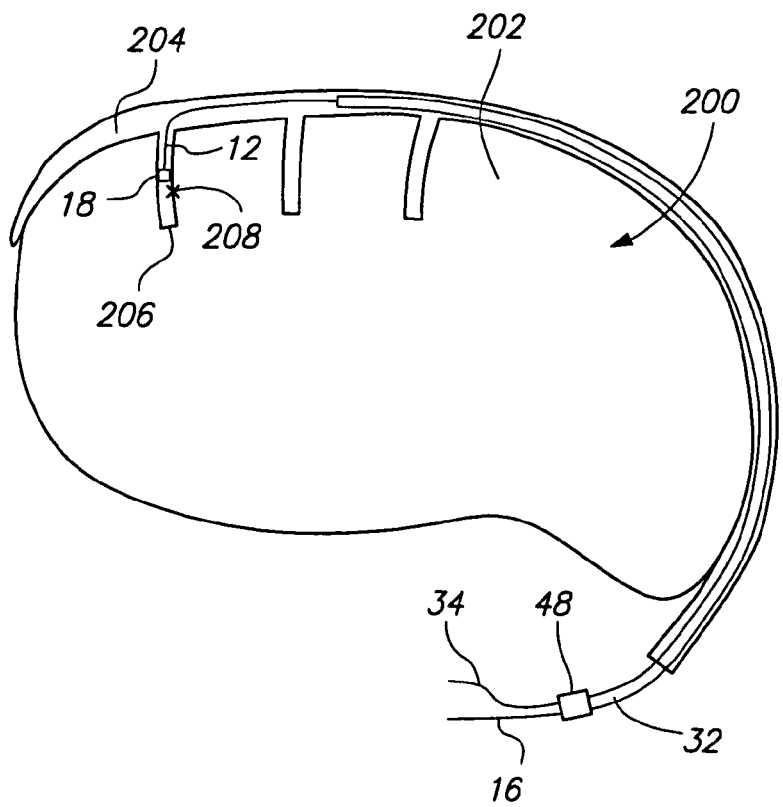

Assuming that additional stimulation leads 12 are to be placed within the brain 200, the delivery catheter 32 can be pulled back in the proximal direction until its distal end resides within the superior sagittal sinus 204 (FIG. 14D), and the guidewire 34 can be manipulated into another superior cerebral vein 206', such that the distal end of the guidewire 34 is located distal to another selected stimulation site 208' (FIG. 14E). The delivery catheter 32 can then be advanced over the guidewire 34 until the distal end of the delivery catheter 32 is placed adjacent the other selected stimulation site 208', the guidewire 34 can be retracted proximal to the other selected stimulation site 208', another stimulation lead 12 with another pusher element 36 can be advanced through the dedicated delivery lumen 54 until the electrode 18 is adjacent the other selected stimulation site 208', and the pusher element 36 can then be detached from the electrode 18 by applying an electrical current to the proximal end of the core wire 16 (FIG. 14F). The steps illustrated in FIGS. 14A-14F can then be repeated if additional stimulation leads 12 are to be placed within the brain 200. Notably, the dedicated delivery lumen 54 should be large enough to accommodate the electrode 18 of the currently deployed stimulation lead 12, an associated pusher element 36, and the multiple signal wires 16 of the current and previously deployed stimulation leads 12.

In an alternative multi-stimulation lead deployment method, the delivery catheters 32 illustrated in FIG. 10 or FIG. 11 can be used. In this case, the stimulation leads 12 are deployed from the delivery catheter 32 in the same manner as the stimulation leads 12 are deployed from the previously described delivery catheter 32 illustrated in FIGS. 14A-14F, with the exception that all of the stimulation leads 12 can be deployed through the respective dedicated signal wire delivery lumens 56 (shown in FIGS. 10 and 11) of the delivery catheter 32. In this manner, previously deployed stimulation leads 12 will not be disturbed by the subsequent introduction of the stimulation leads 12 through the delivery catheter 32.

Figure 15:
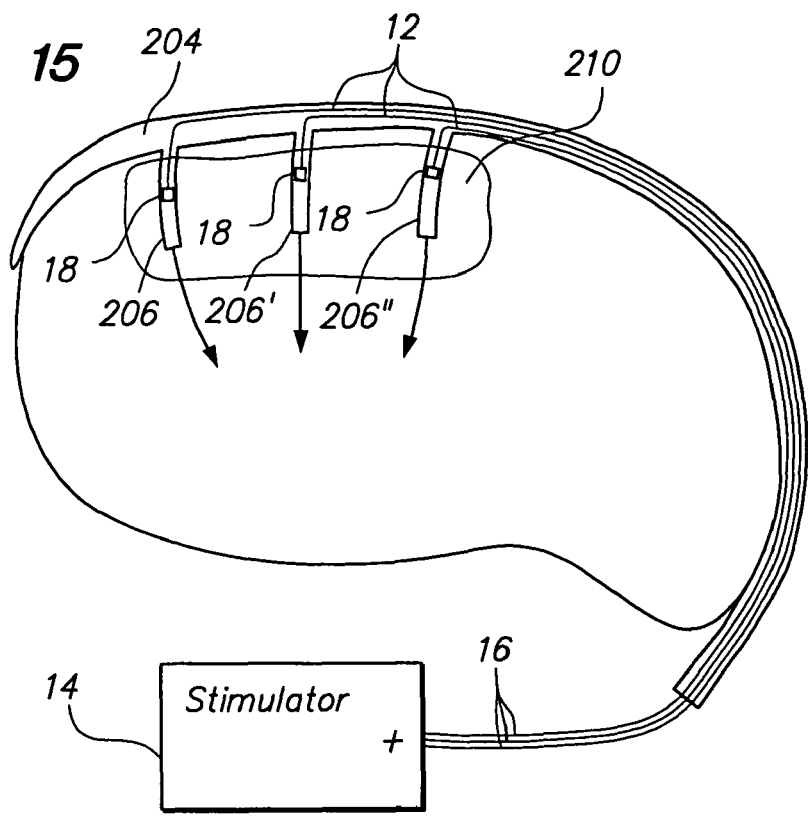
FIG. 15 is a side view of the monopolar arrangement of the system of FIG. 1 arranged in accordance with the schematic diagram of FIG. 3 to stimulate the cortical tissue of a patient's brain.

Whichever method is used to deploy the stimulation leads, the proximal ends of the implanted stimulation leads 12 will remain outside of the patient's body after the stimulation deployment process is completed, and in particular, will extend from the vascular access point, e.g., the internal jugular vein or femoral vein. These exposed ends of the stimulation leads 12 can be subcutaneously routed a short distance to the clavical or chest region or behind the ear of the patient (in this case where the jugular vein is the access point) or the abdominal or groin region of the patient (in the case where the femoral vein is the access point), where they can be coupled to the implanted stimulation source 14, as illustrated in FIG. 15. Alternatively, the stimulation source 14 may not be implanted, but rather located exterior to the patient. e.g., during a non-chronic procedure. The electrodes 18 of the stimulation leads 12 are coupled in parallel to the positive terminal of the stimulation source 14 to form a monopolar arrangement, whereby electrical signals travel from the electrodes 18 to the electrically conductive casing of the implanted stimulation source 14 when the stimulation source 14 is operated. As a result, the brain tissue contained within a region 210 generally surrounding the selected superior cerebral veins 206 is stimulated.

Figure 16:
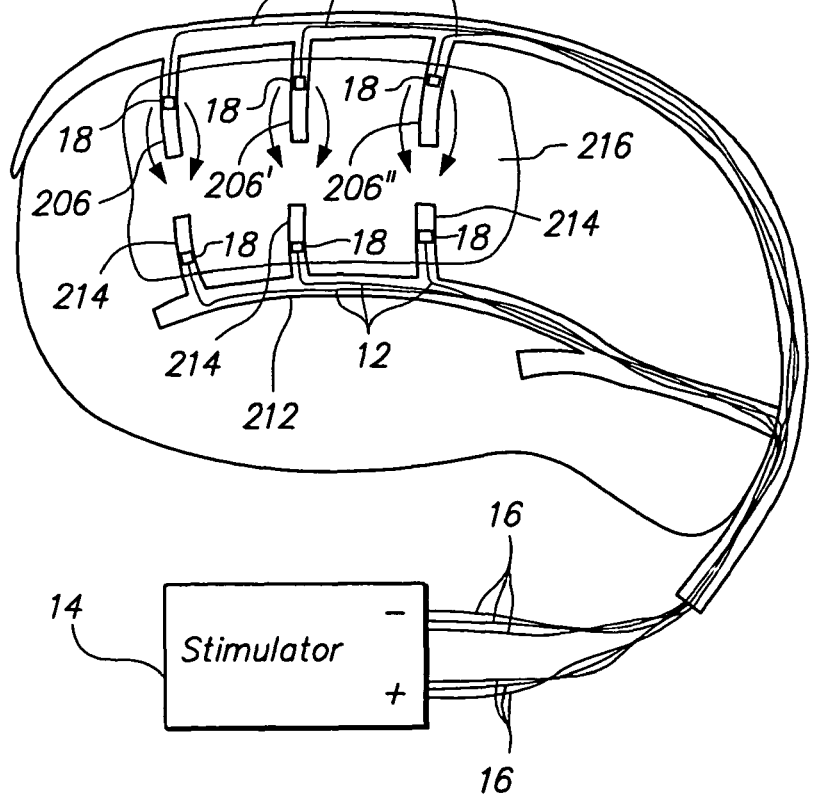
FIG. 16 is a side view of the bipolar arrangement of the system of FIG. 1 arranged in accordance with the schematic diagram of FIG. 4 to stimulate the cortical tissue of a patient's brain.

Using a stimulation lead implantation process similar to that described above, respective electrodes 18 of three stimulation leads 12 can be implanted within the superior cerebral veins 206 branching from the superior sagittal sinus 204, and the respective electrodes 18 of three more stimulation leads 12 can be implanted within the inferior cerebral veins 214 branching from the inferior sagittal sinus 212, as illustrated in FIG. 16. The stimulation leads 12 can be routed into the inferior sagittal sinus 212 via the straight sinus 216 of the superior sagittal sinus 204. Again, the inner jugular vein or femoral vein can be used as the access point to the patient's vasculature. As illustrated, electrodes 18 of the stimulation leads 12 located in the superior cerebral veins 206 are coupled in parallel to the positive terminal of the stimulation source 14, and the electrodes of the stimulation leads 12 located in the inferior cerebral veins 214 are coupled in parallel to the negative terminal of the stimulation source 14. In this manner, a bipolar arrangement is formed, whereby electrical signals travel from the electrodes 18 located in the superior cerebral veins 206 to the electrodes 18 located in the inferior cerebral veins 214 when the stimulation source 14 is operated. As a result, the brain tissue contained within a region 216 between the selected superior and inferior cerebral veins is therapeutically stimulated.

Using a stimulation lead implantation process similar to that described above, respective bipolar electrodes 18(1) and 18(2) of three stimulation leads 12' (shown in FIG. 2 can be implanted within the superior veins branching from the superior sagittal sinus, as illustrated in FIG. 17. Again, the inner jugular vein or femoral vein can be used as the access point to the patient's vasculature. As illustrated, the distal electrodes 18(2) of the stimulation leads 12' are coupled in parallel to the positive terminal of the stimulation source 14, and the proximal electrodes 18(1) of the stimulation leads 12' are coupled in parallel to the negative terminal of the stimulation source 14. In this manner, a bipolar arrangement is formed, whereby electrical signals travel from the distal electrodes 18(2) to the proximal electrodes 18(1) on the stimulation leads 12'. As a result, the brain tissue contained within a regions 218 between and surrounding the selected superior veins is therapeutically stimulated.

Referring now to FIG. 18, another intravascular brain stimulation kit 60 arranged in accordance with another preferred embodiment of the present invention is illustrated. The brain stimulation kit 60 comprises a plurality of the previously described electrical stimulation electrode leads 12 (or stimulation electrode leads 12') and implantable electrical stimulation source 14 (not shown in FIG. 18), a delivery catheter 62 configured for intravascularly delivering the electrical stimulation leads 12 into selected blood vessels within the patient's brain, the previously described guidewire 34, and a pusher element 64.

The delivery catheter 62 comprises an elongate, flexible, catheter body 66 and a guidewire lumen 68, signal wire lumen 70, and pusher element lumen 72 (shown in FIG. 19) longitudinally extending through the catheter body 66. The catheter body 66 may be composed of the same material and have the same dimensions as the previously described catheter body 44. The guidewire lumen 68 houses the guidewire (not shown), the signal wire lumen 70 houses the signal wires 16 of the stimulation leads 12, and the pusher element lumen 72 houses the electrodes 18 of the stimulation leads 12 and the pusher element 64. The delivery catheter 62 comprises a proximal adapter 74 suitably mounted on the proximal end of the catheter body 66. The proximal adapter 74 comprises separate guidewire, signal wire, and pusher element ports (all not shown).

Unlike the previously described pusher elements 36, the pusher element 64 is not mechanically coupled to the electrodes 18, but rather only operates to push the electrodes 18 out from the pusher element lumen 72 of the catheter 62. To this end, the pusher element 64 may simply take the form of a rod composed of an axially rigid, yet laterally flexible material.

The stimulation leads 12 can be delivered to selected stimulation sites within the patient's brain in the same manner as the stimulation leads 12 were delivered in FIGS. 14A-14F, with the exception that the stimulation leads 12 are pre-loaded within the delivery catheter 62 and the pusher element 64 need not be actively detached from the electrodes 18.

Although the delivery catheter 62 is shown in FIG. 18 as having a single signal wire lumen 70, multiple signal wire lumens can be provided. For example, FIG. 20 illustrates the delivery catheter 62 with a dedicated signal wire lumen 70 for each signal wire 16 (in this case, two).

Although the previously described kits have included delivery catheters for delivering the stimulation leads to the selected stimulation sites within the brain, stimulation leads can be delivered without delivery catheters. For example, FIG. 22 illustrates a brain stimulation kit 90 that comprises a plurality of electrical stimulation electrode leads 92, and the previously described implantable electrical stimulation source 14 (not shown in FIG. 22), guidewire 34, and pusher element 36.

Like the previously described stimulation electrode lead 12, the stimulation electrode lead 92 illustrated in FIG. 22 comprises a flexible electrically conductive wire 94 and a single electrode 96 mounted at the distal end of the wire 94. Unlike the previously described stimulation electrode lead 12, however, the electrode 96 comprises a lumen 98 sized to receive the guidewire 34, such that the electrode 18 can longitudinally slide along the guidewire 34. The electrode 96 is bullet-shaped, i.e., it is generally shaped as a cylinder with a tapered distal tip. In this manner, the exposed electrode 96 can be introduced through the patient's vasculature without the risk of causing tissue trauma.

Referring now to FIGS. 23A-23E, a preferred method of delivering the stimulation leads 92 to a selected region of the patient's brain will now be described. As with the previously described exemplary method, the stimulation leads 92 are placed within the superior cerebral veins 206 branching off of the superior sagittal sinus 204, so that the cortex 202 of the brain 200 can ultimately be electrically stimulated to treat a neurological disorder within the patient.

Figure 23A:
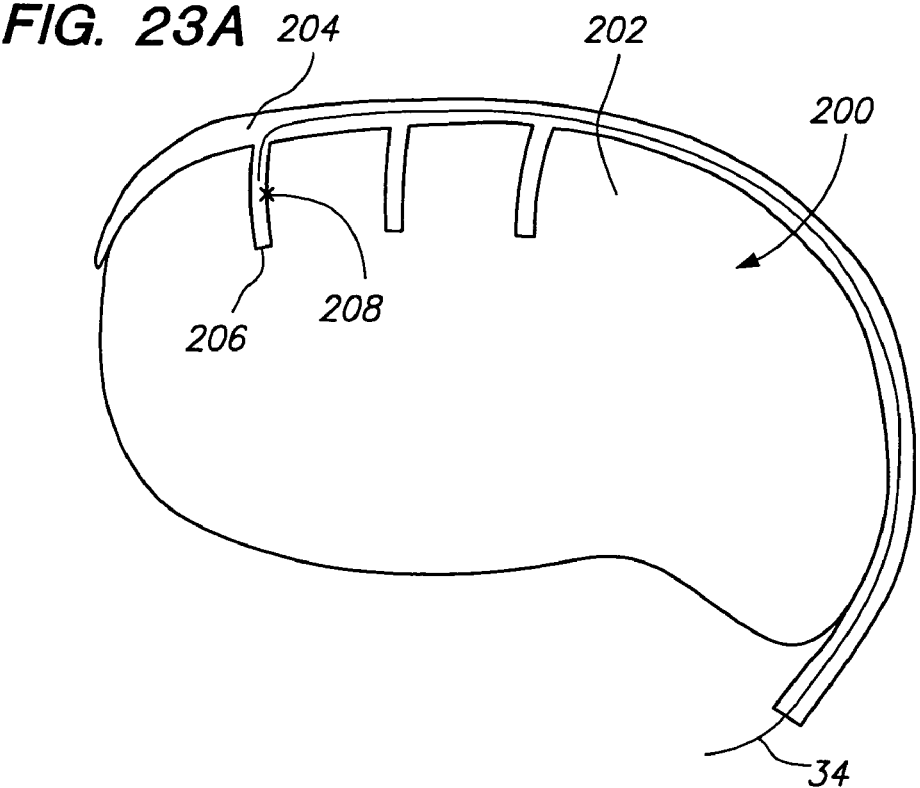
Figure 23B:
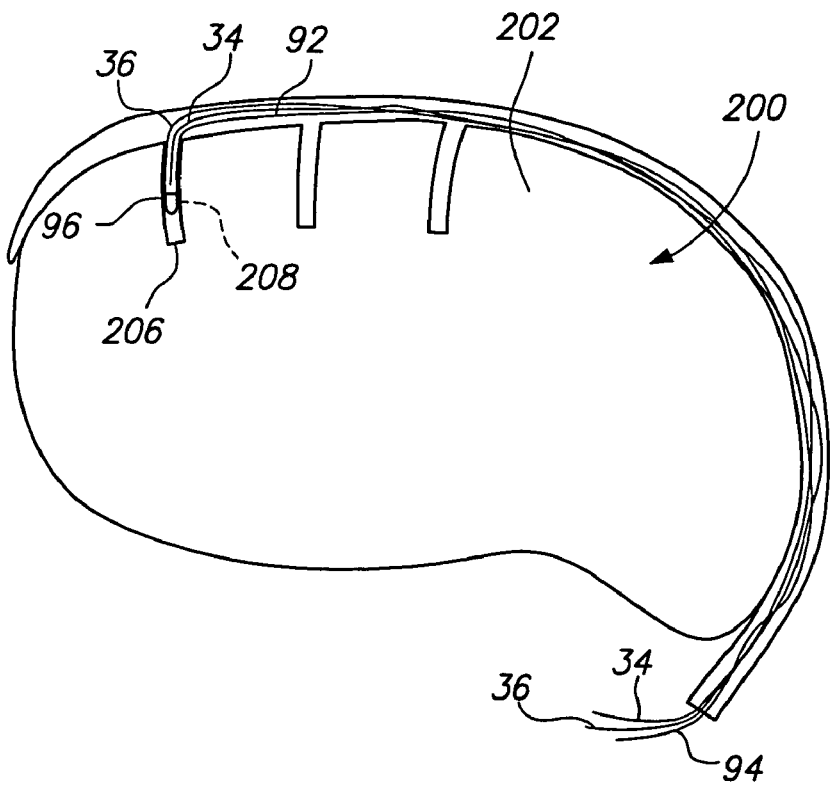

Like in the previous method, the guidewire 34 is routed through the superior sagittal sinus 204 and into a selected cerebral vein 206 until the distal end of the guidewire 34 is proximal to a selected stimulation site 208 (FIG. 23A). The jugular vein or femoral vein, for examples, can be used as the access point into the patient's vasculature. Once proper placement of the guidewire 34 is achieved, the electrode 96 of the stimulation lead 92 is threaded over the guide wire 34, and distally advanced up the guidewire 34 by pushing the pusher element 36 until the electrode 96 is placed adjacent the selected stimulation site 208 (FIG. 23B). Next, the pusher element 36 is electrolytically detached from the electrode 96 and removed from the patient (FIG. 23C).

Figure 23E:
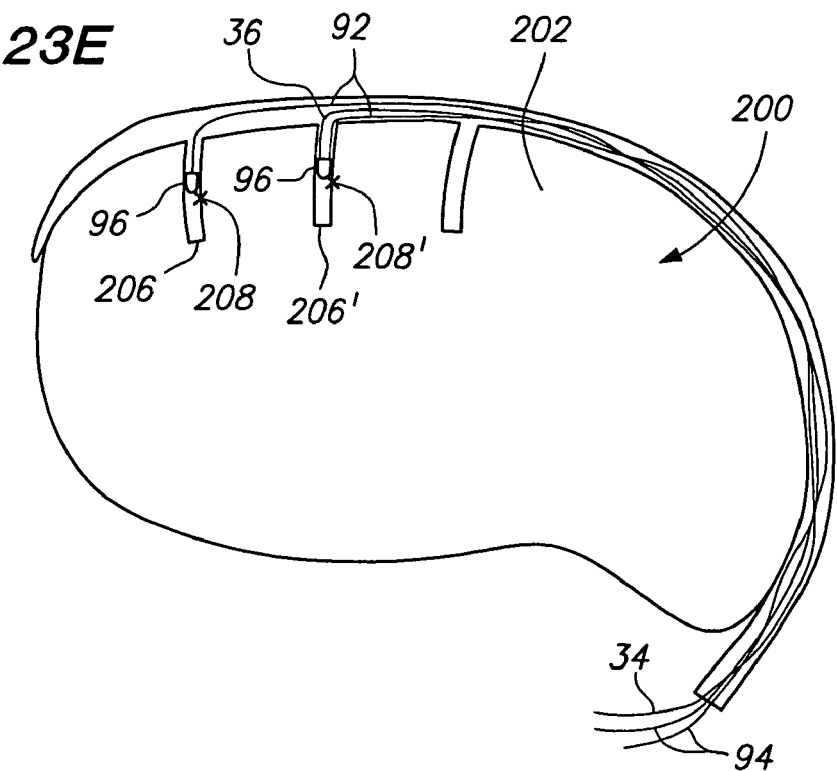
Figure 23F:
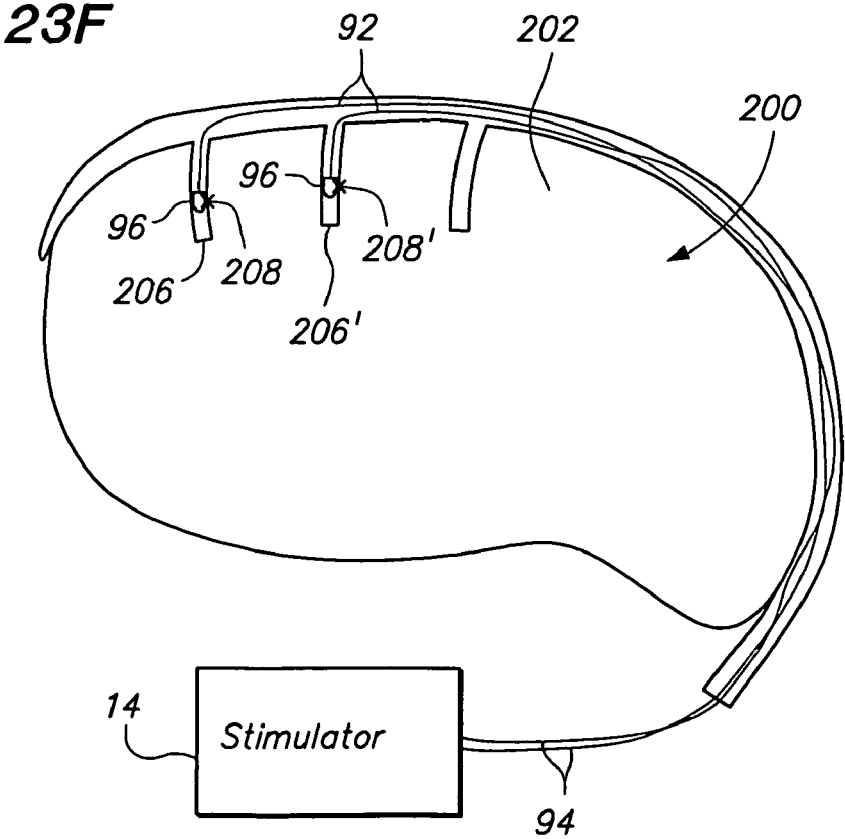

Assuming that additional stimulation leads 92 are to be placed within the brain 200, the guidewire 34 can be pulled back in the proximal direction, and then manipulated into another superior cerebral vein 206', such that the distal end of the guidewire 34 is located proximal to another selected stimulation site 208' (FIG. 23D). Another stimulation lead 92 with an associated pusher element 36 can be distally advanced up the guidewire 34 until the electrode 96 is adjacent the other selected stimulation site 208', and the pusher element 36 can then be detached from the electrode 96 and removed from the patient (FIG. 23E). The steps illustrated in FIGS. 23D and 23E can then be repeated if additional stimulation leads 92 are to be placed within the brain 200. The guidewire 34 is then removed from the patient's body, and the proximal ends of the signal wires 94, which extend from the patient's body (e.g., from the access point of the jugular vein or femoral vein), are then connected to the implanted stimulation source 14 (FIG. 23F).

Figure 24:
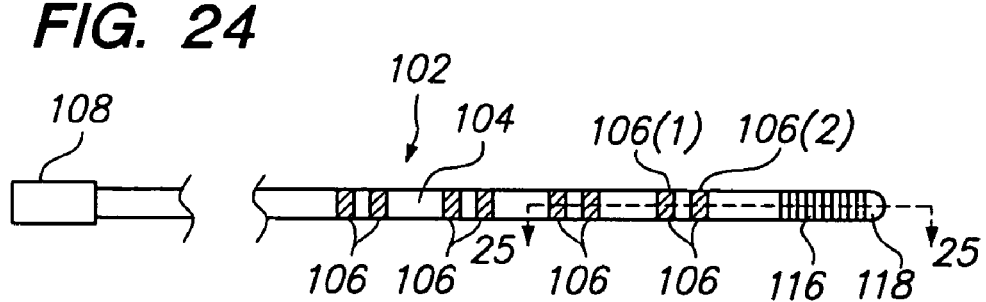
FIG. 24 is a plan view of another stimulation lead constructed in accordance with a preferred embodiment of the present invention.
Figure 25:
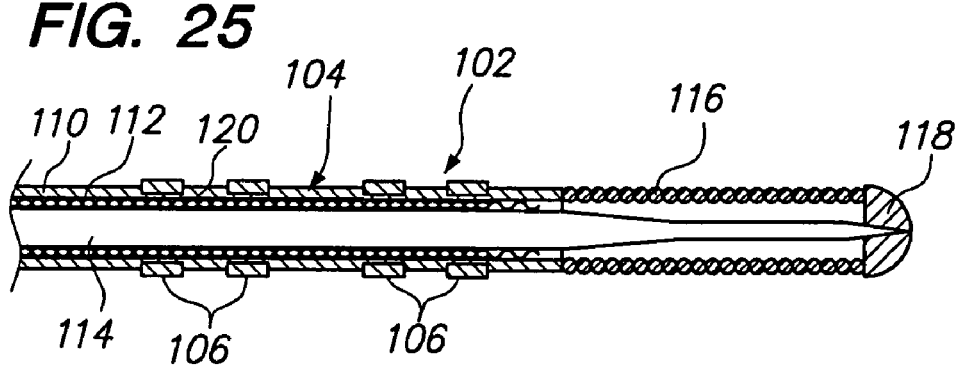
FIG. 25 is a cross-sectional view of the stimulation lead of FIG. 24, taken along the line 25-25.

Although all the previously described stimulation leads have been delivered to the selected stimulation sites using either a separate delivery catheter, a separate guidewire, or both, stimulation leads can take the form of a guidewire or catheter to minimize the need for additional delivery elements. For example, FIGS. 24 and 25 illustrate a stimulation lead 102 that takes the form of a guidewire. The guidewire 102 comprises an elongated flexible shaft 104, a plurality of bipolar electrode pairs 106 (comprising a proximal ring electrode 106(1) and a distal ring electrode 106(2)) mounted to the distal end of the shaft 104, and an electrical connector 108 mounted to the proximal end of the shaft 104.

The shaft 104 is formed of an outer tubular member 110, an inner braided tubular member 112, and a core member 114 that is disposed within the inner tubular member 112 and extends past the distal end thereof. The shaft 104 further comprises a coil 116 secured to the distal end of the core member 114 using suitable means, such as brazing, soldering, or bonding, and a rounded distal tip 118 secured to the distal extremity of the core member 114. The inner tubular member 112 comprises a plurality of electrical conductors 120 that are distally connected to the electrodes 106 and proximally connected to the connector 108. The dimensions of the guidewire 102 are preferably the same as the dimensions of the guidewire 34 described above. Details regarding the construction of guidewires with electrodes are disclosed in U.S. Pat. No. 5,509,411, which is expressly incorporated herein by reference.

Figure 26:
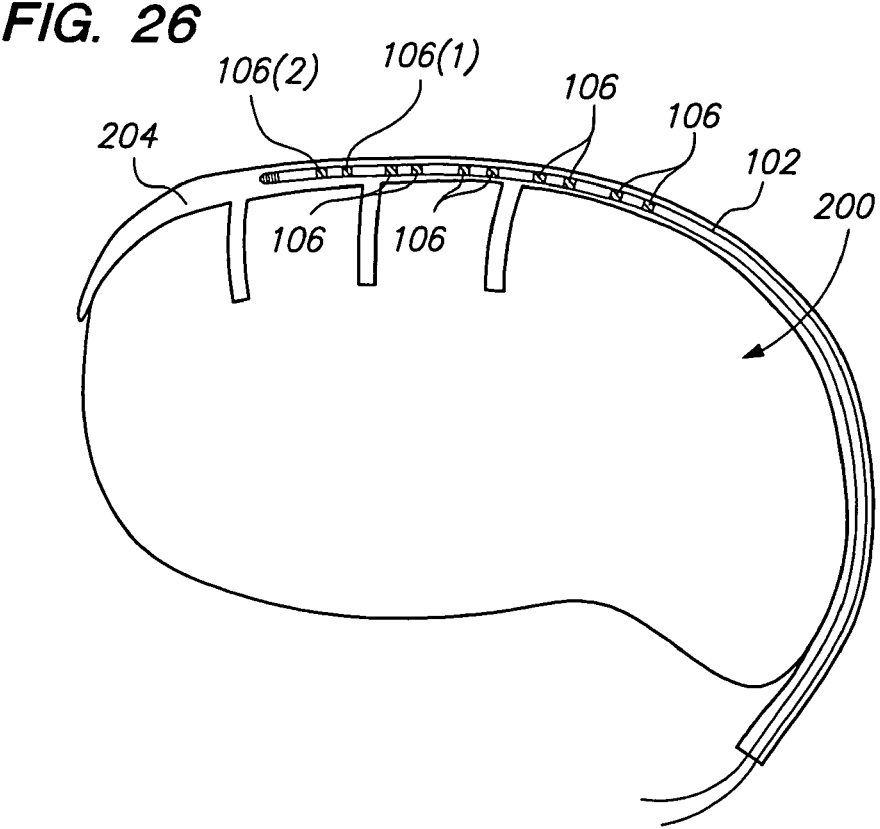
FIG. 26 is a side view of the stimulation lead of FIG. 24 shown stimulating brain tissue of a patient from a superior cerebral vein.
Figure 27:
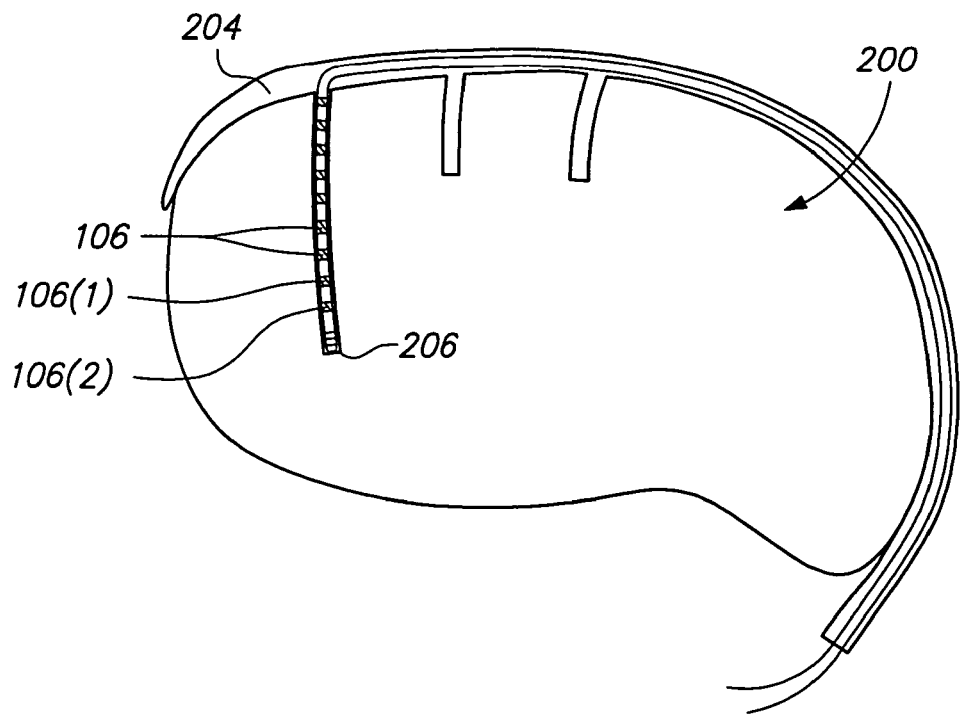
FIG. 27 is a side view of the stimulation lead of FIG. 24 shown stimulating brain tissue of a patient from the superior sagittal sinus.

It can be appreciated that because the stimulation lead 102 takes the form of a guidewire that can be manipulated through the patient's cerebral vasculature, no other delivery mechanisms are required. As with the previously described stimulation leads 12, the guidewire 102 can be deployed into various vessels within the patient's brain 200, and can be connected to an implanted stimulation source. For example, FIG. 26 illustrates the guidewire 102 placed along the superior sagittal sinus 204. In this case, the cortical brain tissue running along the superior sagittal sinus 204 can be therapeutically stimulated by the conveyance of stimulation energy between the distal and proximal electrodes 106(1) and 106(2) of the bipolar electrode pairs 106. FIG. 27 illustrates the guidewire 102 placed along a superior cerebral vein 206. In this case, the cortical brain tissue running along the superior cerebral vein 206 can be therapeutically stimulated by the conveyance of stimulation energy between the distal and proximal electrodes 106(1) and 106(2) of the bipolar electrode pairs 106.

In alternative embodiments, the electrodes 106 of the guidewire 102 may be configured in a monopolar arrangement. In this case, the stimulation energy may be conveyed through the cerebral tissue from the monopolar electrodes to the casing of the implanted stimulation source. Or, alternatively, a second guidewire 106 can be placed into another vessel, such as the inferior sagittal sinus. In this case, the stimulation energy may be conveyed through the cerebral tissue between the superior and inferior sagittal sinuses.

Figure 28:
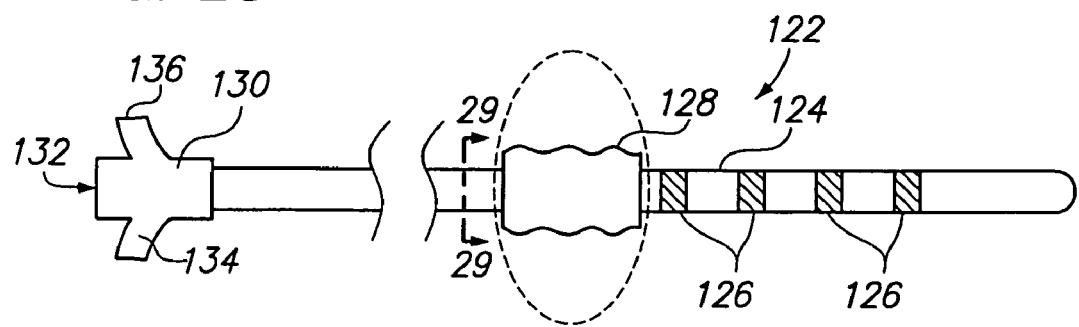
FIG. 28 is a plan view of still another stimulation lead constructed in accordance with a preferred embodiment of the present invention.

FIG. 28 illustrates a stimulation lead 122 that takes the form of a catheter. The catheter 122 comprises an elongate, flexible, catheter body 124, a plurality of ring electrodes 126, an inflatable balloon 128 mounted on the distal end of the catheter body 124 proximal to the electrodes 126, and a proximal adapter 130 mounted on the proximal end of the catheter body 124. The catheter body 124 can have the same dimensions and be composed of the same material as the previously described catheter body 44. The proximal adapter 130 comprises a guidewire port 132, an electrical connector 134, and an inflation port 136.

The balloon 128 can be transformed from a deflated state into an inflated state (shown in phantom) by conveying an inflation medium, such as saline, into the balloon. The balloon 128 is preferably about 0.5 to 3 cm in length, and is composed of a wall that can be inflated by fluid supplied through catheter body 124. The balloon wall is preferably composed of a polymeric material, and preferably an elastomeric, stretchable material such as silicone rubber, latex rubber, or polyvinyl chloride, or alternatively, a non-stretchable film material, such as polyethylene or polypropylene. Attachment of the balloon wall to the catheter body 124 can be accomplished using suitable means, such as gluing, heat sealing or the like.

Figure 29:
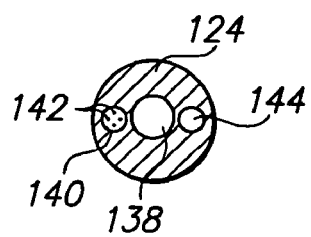
FIG. 29 is a cross-sectional view of the stimulation lead of FIG. 28, taken along the line 29-29.

Referring further to FIG. 29, the catheter 122 has a guidewire lumen 138, signal wire lumen 140, and inflation lumen 144 longitudinally extending through the catheter body 124. The guidewire lumen 138 is capable of receiving a guidewire (not shown). The signal wire lumen 140 houses signals wires 142, which distally terminate at the electrodes 126 and proximally terminate in the electrical connector 134 on the proximal adapter 130. Inflation medium may be conveyed into the inflation port 136, through the inflation lumen 144, and into the interior of the balloon 128 in order to place the balloon 128 in its expanded state.

The catheter 122 can be used to stimulate brain tissue, while chronically occluding the blood vessel in which it is disposed. In this manner, the risk of a thromembolic stroke (mainly on the arterial side) is minimized. Preferably, chronic occlusion will be accomplished in blood vessels where there is a superfluous blood supply, such as the meningeal arteries.

Figure 30A:
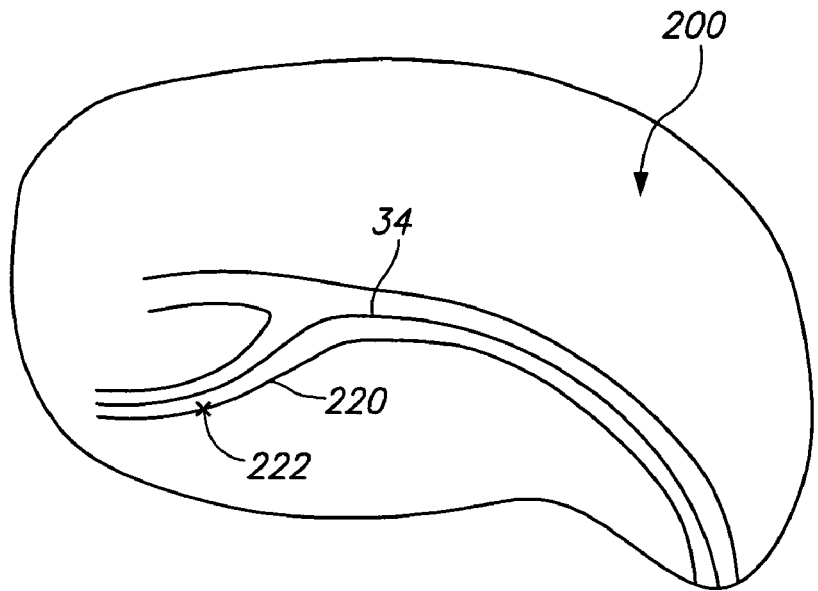
FIGS. 30A-30D are side views illustrating a method of intravascularly delivering the stimulation lead of FIG. 28 into, and occluding, a cerebral blood vessel of a patient.
Figure 30B:
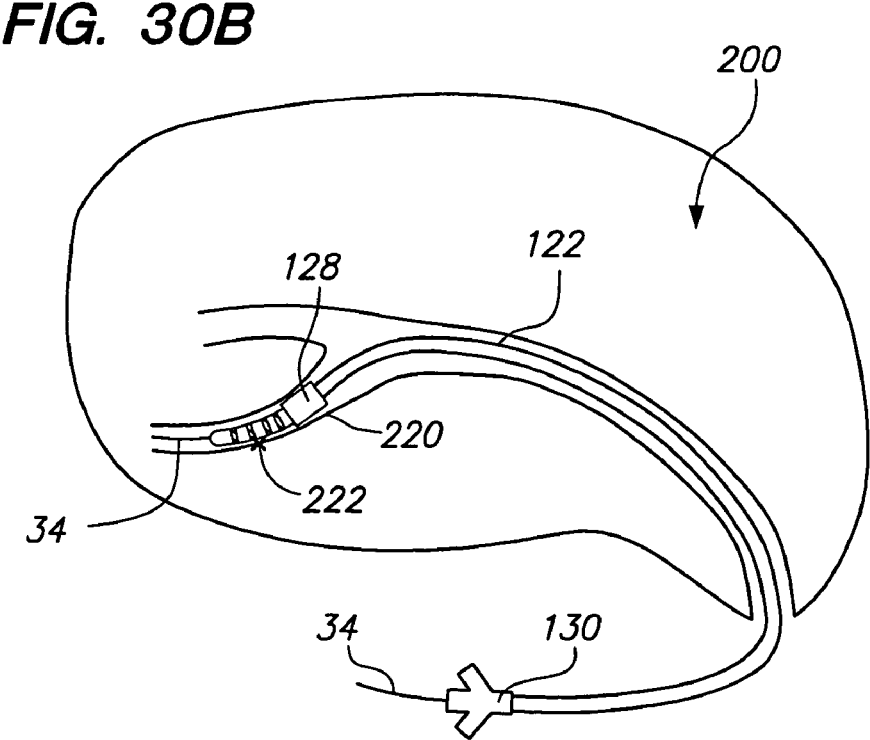
Figure 30C:
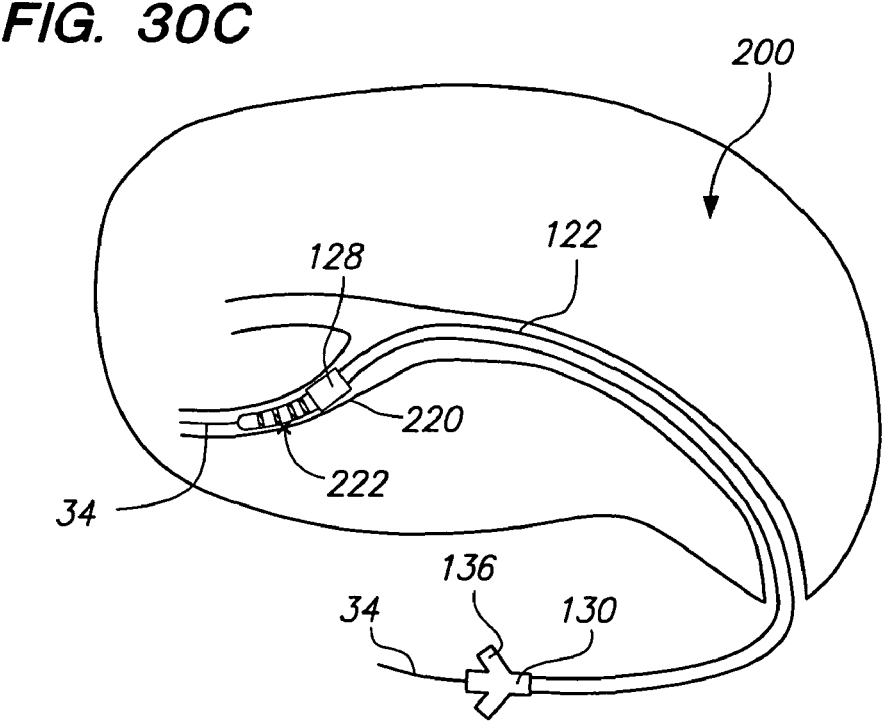
Figure 30D:
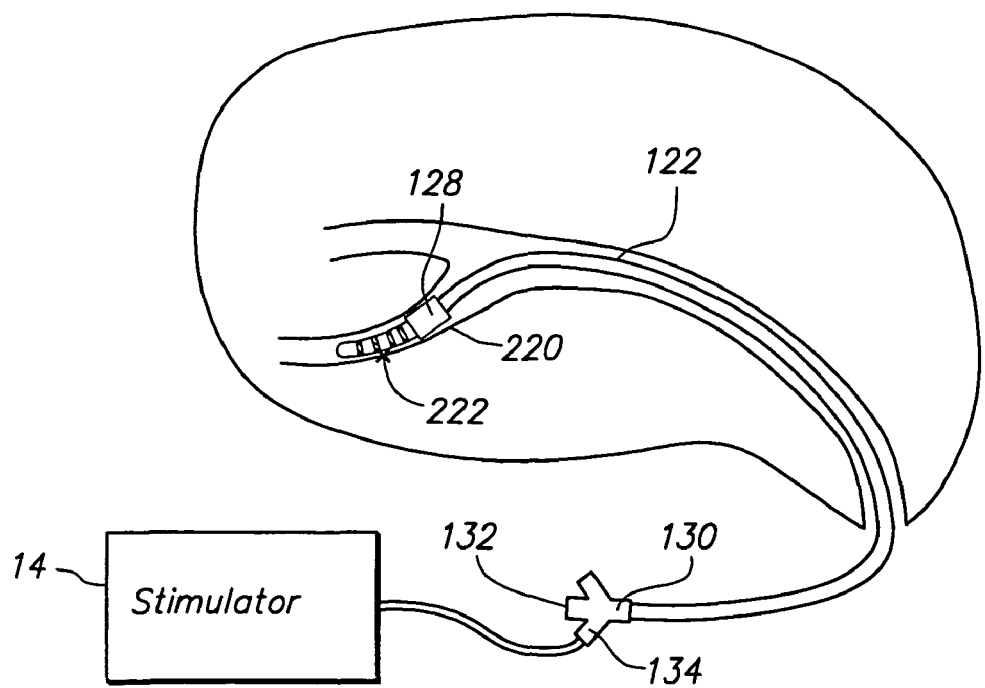

A method of delivering the catheter 122 into a selected cerebral blood vessel 212 within the brain 200, and chronically occluding the blood vessel, will now be described with respect to FIGS. 30A-30D. First, a guidewire 34 is routed into the blood vessel 220 distal to a selected stimulation site 222 (FIG. 30A). The jugular vein or artery or the femoral vein or artery, for examples, can be used as the access point into the patient's vasculature. Once proper placement of the guidewire 34 is achieved, the distal end of the catheter 122 is introduced over the guidewire 34, and the catheter 122, while the balloon 128 is in its deflated state, is distally advanced up the guidewire 34 until the distal end of the catheter 122 is adjacent the selected stimulation site 222 (FIG. 30B). Next, inflation medium is conveyed up the catheter 122 via the inflation port 136 on the proximal adapter 130, such that the balloon 128 is placed into its expanded state (FIG. 30C). In this manner, the balloon 128 seals the blood vessel 220, thereby occluding the blood flow through the blood vessel 220. The guidewire 34 is then removed from the catheter 122 via the guidewire port 132 on the proximal adapter 130, and thus, the patient's body, and the electrical connector 134 on the proximal adapter 130, which extends from the patient's body (e.g., from the access point of the jugular vein or femoral vein), is then connected to the implanted stimulation source 14 (FIG. 30D). The inflation port 136 on the proximal adapter 130 is preferably sealed, so that the balloon 128 is maintained in its expanded state. Alternatively, the blood flow through the blood vessel 220 is only temporarily occluded, in which case, the balloon 128 is placed back into its deflated state by conveying inflation medium out from the inflation port 136.

Figure 31:
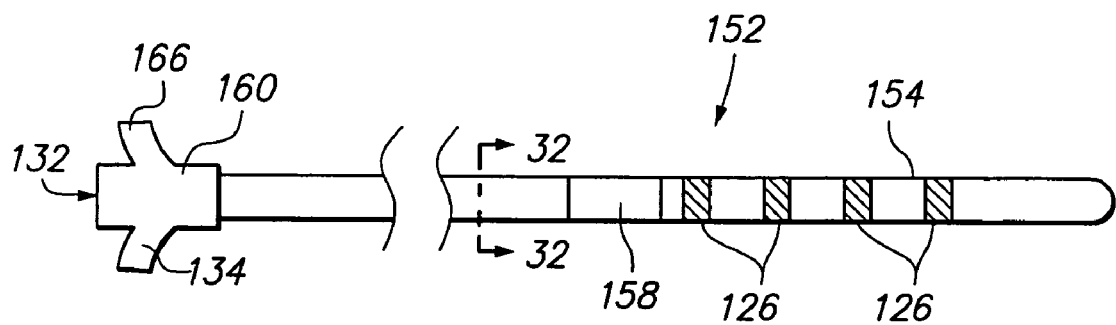
FIG. 31 is a plan view of yet another stimulation lead constructed in accordance with a preferred embodiment of the present invention.
Figure 32:
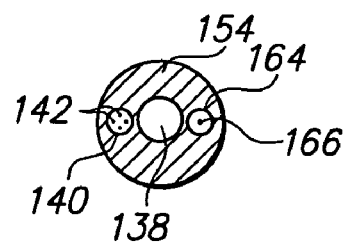
FIG. 32 is a cross-sectional view of the stimulation lead of FIG. 31, taken along the line 32-32.

FIG. 31 illustrates another stimulation lead 152 that takes the form of a catheter. The catheter 152 is similar to the previously described catheter 122, with the exception that it uses ablation energy, rather than a balloon to occlude a cerebral blood vessel. In particular, the catheter 152 comprises an elongate, flexible, catheter body 154, a plurality of the previously described ring electrodes 126, an ablation element 158, such as a radio frequency (RF) electrode, mounted on the distal end of the catheter body 154 proximal to the electrodes 126, and a proximal adapter 160 mounted on the proximal end of the catheter body 154. The catheter body 154 can have the same dimensions and be composed of the same material as the previously described catheter body 44. The proximal adapter 160 comprises the previously described guidewire port 132 and electrical connector 134, as well as ablation port 166.

In addition to the previously described guidewire lumen 138 and signal wire lumen 140 in which there are disposed a guidewire (not shown) and signal wires 142, respectively, the catheter 152 further comprises an ablation lumen 164 longitudinally extending through the catheter body 154. The ablation lumen 164 houses an ablation wire 166, which distally terminates at the ablation element 158 and proximally terminates in the ablation port 166 on the proximal adapter 360.

Figure 33A:
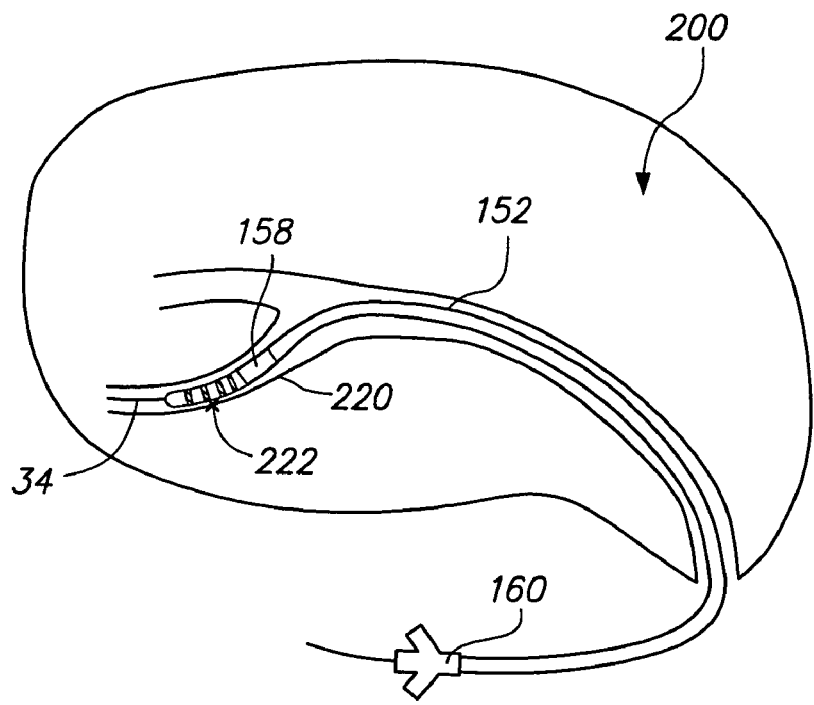
FIGS. 33A-33B are side views illustrating a method of intravascularly delivering the stimulation lead of FIG. 31 into, and occluding, a cerebral blood vessel of a patient.
Figure 33B:
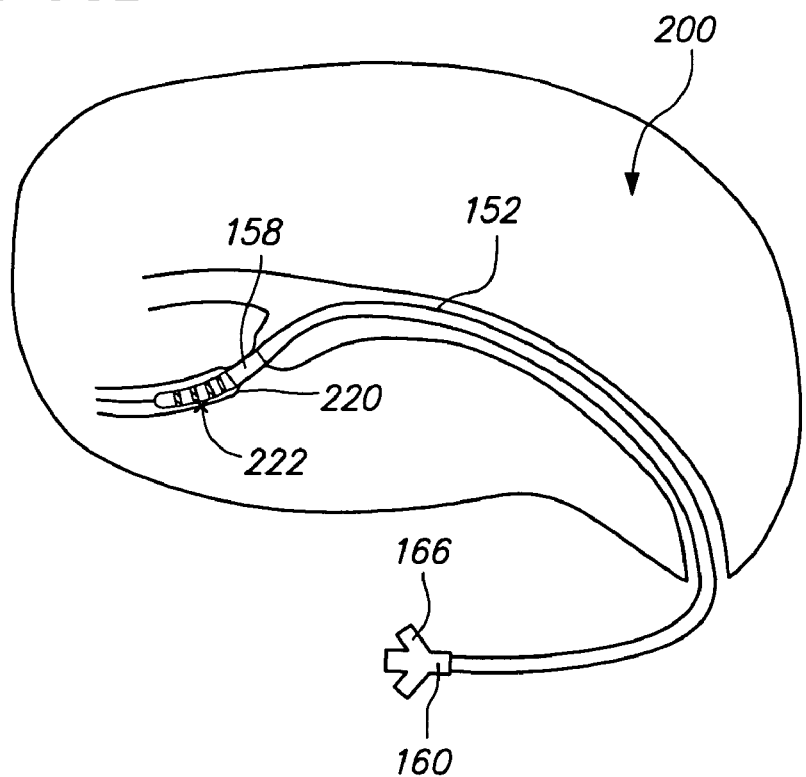

Like the previously described catheter 122, the catheter 152 can be used to stimulate brain tissue, while chronically occluding the blood vessel in which it is disposed. A method of delivering the catheter 152 into a selected cerebral blood vessel 220 within the brain 200, and chronically occluding the blood vessel, will now be described with respect to FIGS. 33A-33B. Once the guidewire 34 is properly located distal to the selected stimulation site 222 (as previously shown in FIG. 30A), the distal end of the catheter 152 is introduced over the guidewire 34, and the catheter 152 is distally advanced up the guidewire 34 until the distal end of the catheter 152 is adjacent the selected stimulation site 222 (FIG. 33A). Next, a source of ablation energy (not shown) is connected to the ablation port 166 on the proximal adapter 160, and ablation energy is conveyed through the ablation wire 16 to the ablation element 158. As a result, the surrounding vessel tissue is heated, causing the vessel wall to collapse around the distal end of the catheter 152 (FIG. 33B). In this manner, the blood vessel 220 is sealed around the catheter 152, thereby occluding the blood flow through the blood vessel 220. The guidewire 34 is then removed from the catheter 152 via the guidewire port 132 on the proximal adapter 160, and thus, the patient's body, and the electrical connector 134 on the proximal adapter 160, which extends from the patient's body (e.g., from the access point of the jugular vein or femoral vein), is then connected to the implanted stimulation source 14 in a manner similar to that shown in FIG. 30D.

Although the previously described stimulation leads have been located within the circulatory system of the cerebral vasculature, stimulation leads can also be placed within the ventricular system of the cerebral vasculature, and in particular within the ventricular cavity of the brain. One embodiment that lends itself to the stimulation of brain tissue via the ventricular cavity arranges stimulation electrode leads into an expandable-collapsible basket assembly.

Figure 34:
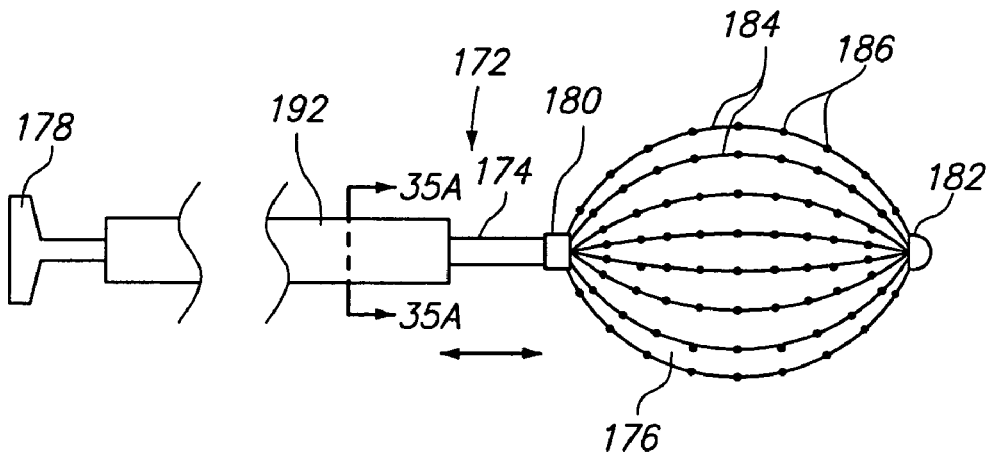
FIG. 34 is a plan view of a stimulation catheter, particularly showing an electrode basket electrode structure in an expanded three-dimensional state.
Figure 35A:
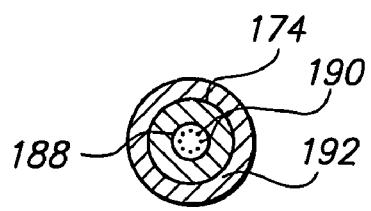
FIG. 35A is a cross-sectional view of the stimulation catheter of FIG. 34, taken along the line 35A-35A.
Figure 35:
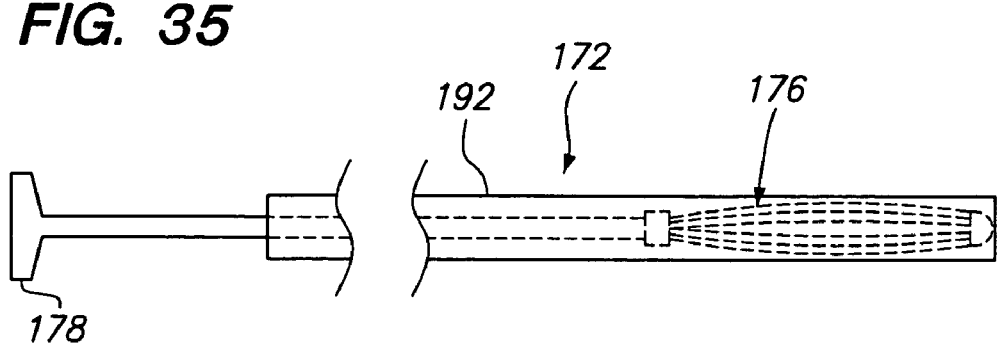
FIG. 35 is a plan view of the stimulation catheter of FIG. 34, particularly showing the basket electrode structure in a compact collapsed state.

FIGS. 34 and 35 illustrate such a catheter 172, which comprises an elongate flexible catheter body 174, a three-dimensional multiple basket electrode structure 176 mounted to the distal end of the catheter body 174, and an electrical connector 178 mounted to the proximal end of the catheter body 174. The catheter body 174 can have the same dimensions and be composed of the same material as the previously described catheter body 44.

The basket electrode structure 176 comprises a base member 180, an end cap 182, and plurality of flexible stimulation leads or splines 184 that extend in a circumferentially spaced relationship between the base member 180 and end cap 182. The splines 184 are preferably made of a resilient inert material, like Nitinol metal or stainless steel. The splines 184 are connected between the base member 180 and the end cap 182 in a resilient, pretensed condition, to bend and conform to the tissue surface that they contact. In the illustrated embodiment, eight splines 184 form the basket electrode structure 176. Additional or fewer splines 184, however, could be used to form the basket electrode structure 176.

The splines 184 carry an array of electrodes 186. In the illustrated embodiment, each spline 184 carries eight electrodes 186. Of course, additional or fewer electrodes 186 can be used. The electrodes 186 can be arranged in a monopolar or a bipolar arrangement. In the bipolar arrangement, stimulation energy may flow between electrodes 18 on the same spline or between electrodes on separate splines. The catheter 172 comprises a signal wire lumen 188 (shown in FIG. 35A) longitudinally extending through the catheter body 174. The signal wire lumen 188 houses signals wires 190, which distally terminate at the electrodes 186 and proximally terminate in the electrical connector 178.

A slideable guide sheath 192 is movable along the axis of the catheter body 174 (shown by arrows in FIG. 34). Moving the sheath 192 in the distal direction over the basket electrode structure 176, collapses it into a compact, collapsed low profile state, as illustrated in FIG. 35. Moving the sheath 192 in the proximal direction away from the basket electrode structure 176, allows it to spring open into a three-dimensional expanded state. Further details of the basket electrode structure are disclosed in pending U.S. Pat. No. 5,647,870, which is expressly incorporated herein by reference.

Figure 36A:
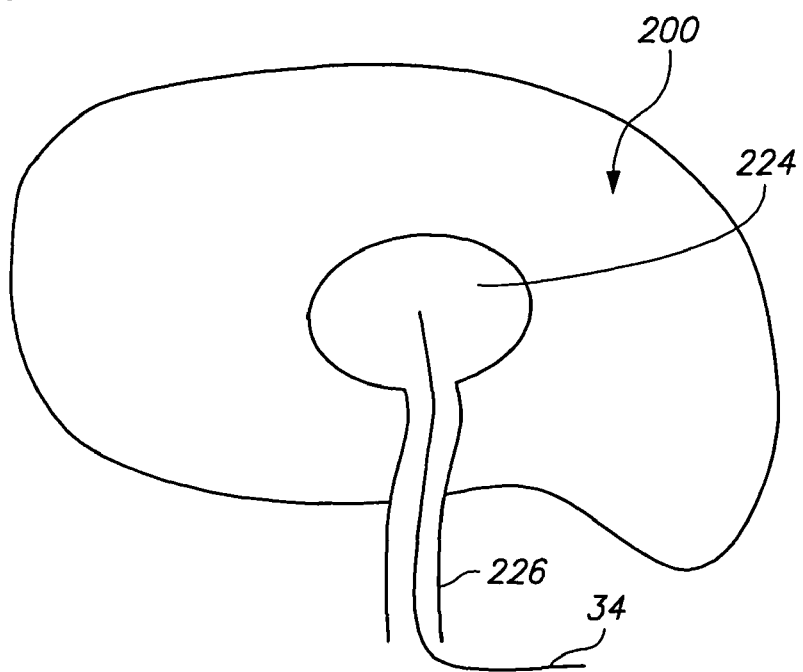
FIGS. 36A-36E are side views illustrating a method of intravascularly delivering and deploying the basket electrode structure of FIG. 34 within a ventricular cavity of a patient's brain.
Figure 36B:
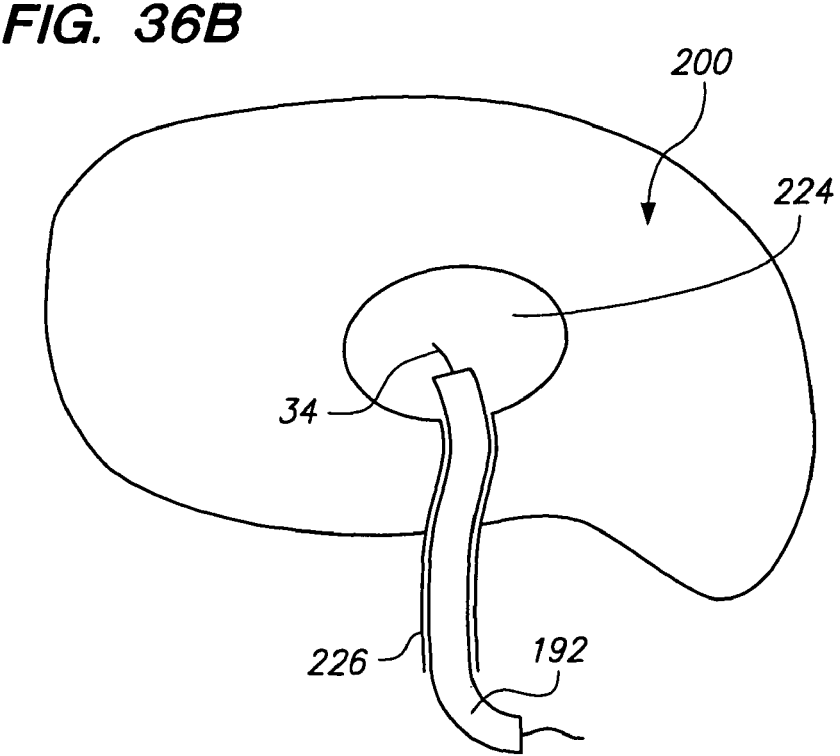
Figure 36C:
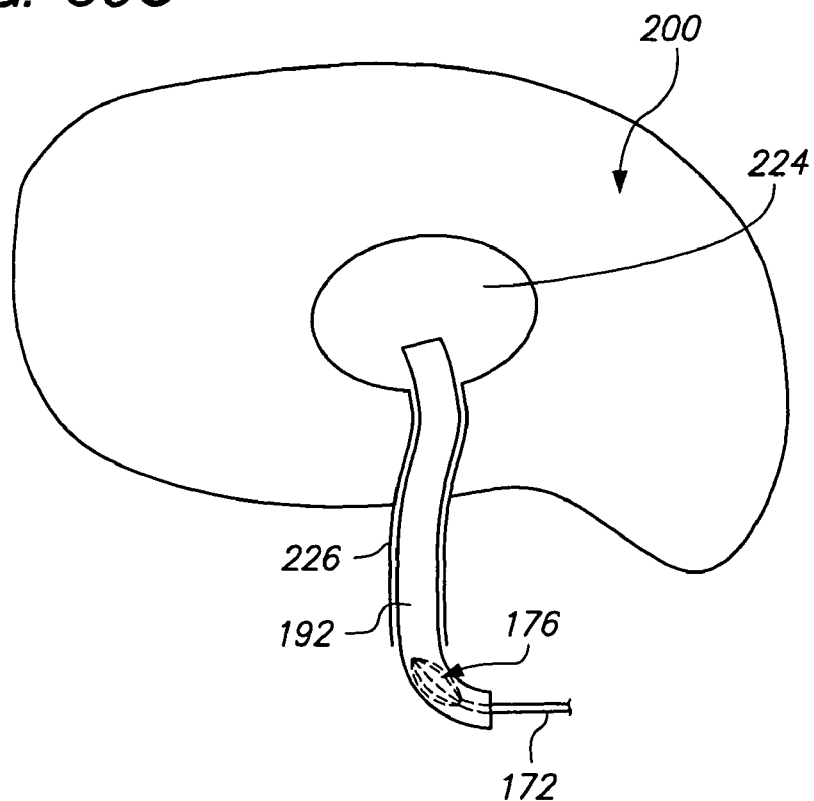
Figure 36D:
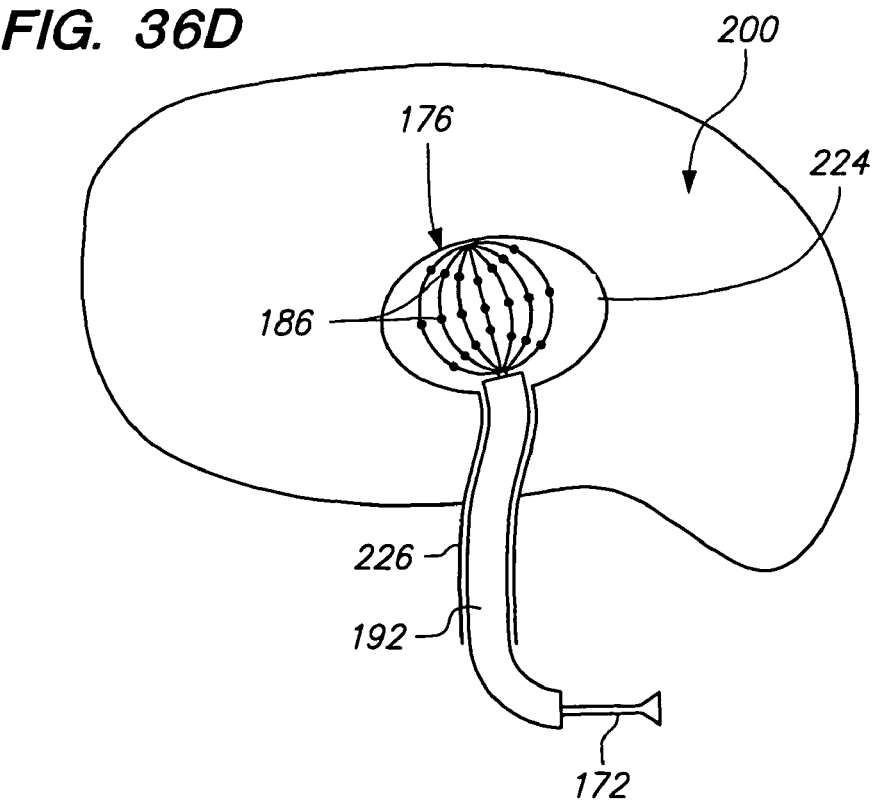
Figure 36E:
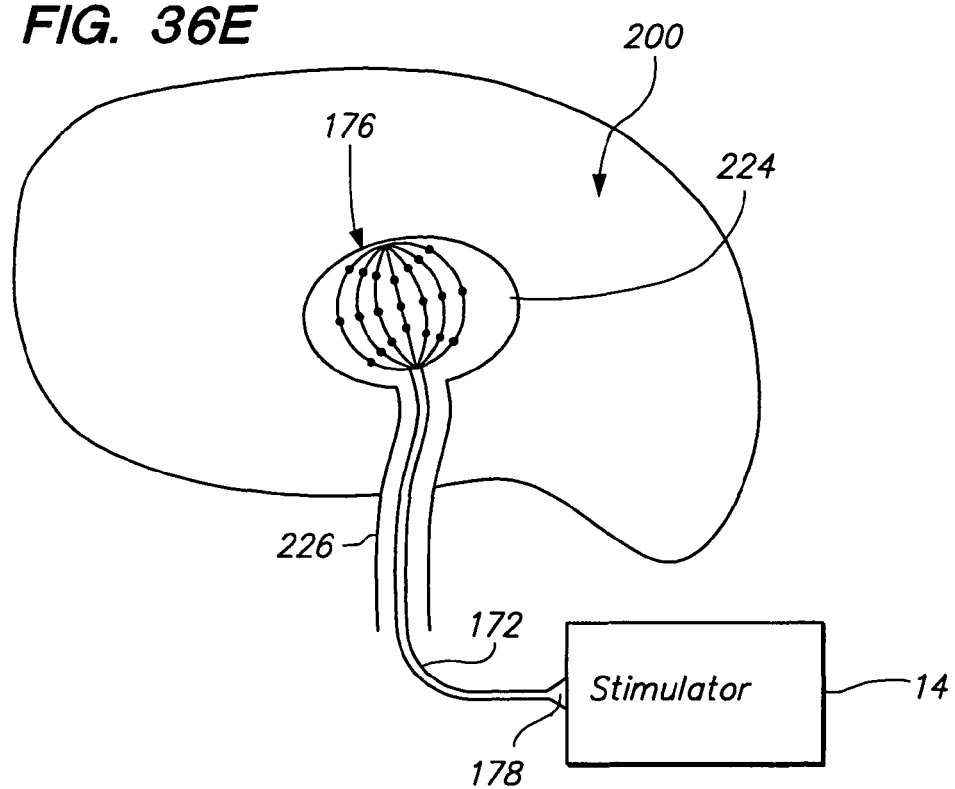

A method of delivering the catheter 172 into a ventricular cavity 224 within the brain 200 will now be described with respect to FIGS. 36A-36E. First, a guidewire 34 is routed up the spinal canal 226 of the patient until the distal end of the guidewire 34 is located within the ventricular cavity 224 (FIG. 36A). Then, the guide sheath 192 is distally advanced up the guidewire 34 until the distal end of the guide sheath 192 resides within the ventricular cavity 224 (FIG. 36B). Next, the guidewire 34 is removed from the guide sheath 192, and the basket electrode structure 176 (shown in phantom) of the catheter 172 is inserted into the proximal end of the guide sheath 192, such that the basket electrode structure 176 is placed into its collapsed state (FIG. 36C). The basket electrode structure 176 is then introduced through the guide sheath 192 until the basket electrode structure 176 is deployed from the distal end of the guide sheath 192 into the ventricular cavity 224 (FIG. 36D). As illustrated, the basket electrode structure 176 assumes its three-dimensional expanded state, such that the electrodes 186 are placed into stable contact with the ventricular cavity 224. The guide sheath 192 is then removed from the patient's body, and the electrical connector 178 of the catheter 172, which extends from the patient's body, and in particular from the back of the patient, is then connected to an implanted stimulation source 14 (FIG. 36E). Depending on the configuration of the electrodes 186 and the connection to the stimulation source 14, the brain tissue surrounding the ventricular cavity 224 can be electrically stimulated in a monopolar or bipolar mode.

Figure 37:
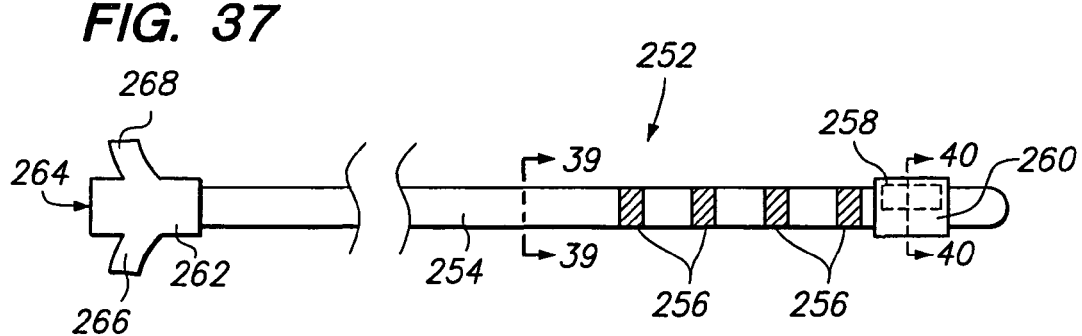
FIG. 37 is a plan view of yet another stimulation lead constructed in accordance with a preferred embodiment of the present invention.
Figure 38:
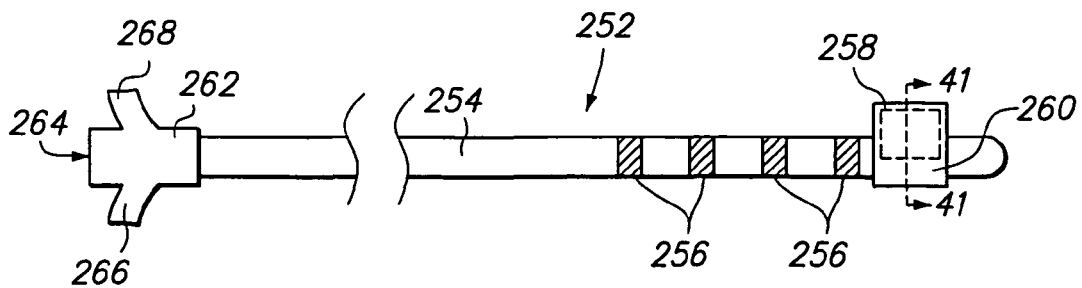
FIG. 38 is a plan view of the stimulation lead of FIG. 37, wherein a stent is particularly shown deployed.

Stimulation leads with vessel stabilization devices will now be described. Referring to FIGS. 37 and 38, a stimulation lead 252 that takes the form of stent catheter is illustrated. The catheter 252 comprises an elongate, flexible, catheter body 254, a plurality of ring electrodes 256, an inflatable balloon 258 (shown in phantom in FIGS. 37 and 38) mounted on the distal end of the catheter body 254, a stent 260 mounted to the distal end of the catheter body 254, and a proximal adapter 262 mounted on the proximal end of the catheter body 254. The catheter body 254 can have the same dimensions and be composed of the same material as the previously described catheter body 44.

The balloon 258 can be transformed from a deflated state (FIG. 37) into an inflated state (FIG. 38) by conveying an inflation medium, such as saline, into the balloon. Expansion of the balloon 258 will accordingly expand the stent 260. The balloon 258 is preferably composed of a suitable non-compliant or semi-compliant material, such as polyethyleneterephthalate (PET), high density polyethylene, polyamides, polycarbonates, NYLON, polyurethanes, polyvinyl chloride, ethylene-vinyl acetate copolymers, and mixtures and combinations thereof.

The stent 260 has a design similar to well-known expandable vascular stents that are employed to enlarge a restricted vein or artery. Such vascular stents have a generally tubular design that initially is collapsed to a relatively small diameter enabling them to pass freely through an artery or vein of a patient. The stent 260 is configured such that it eccentrically expands to a lateral side of the catheter body 254. In particular, the inner surface of the stent 260 is suitably affixed to one side of the catheter body 254, whereas the inner surface of the stent 260 adjacent the opposite side of the catheter body 254 is free. The balloon 258 is suitably bonded to the opposite side of the catheter body 254, such that its expansion will expand the free side of the stent 260.

Figure 39:
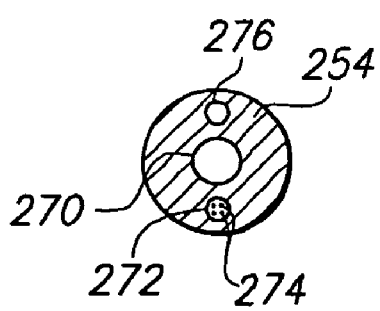
FIG. 39 is a cross-sectional view of the stimulation lead of FIG. 37, taken along the line 39-39.
Figure 40:
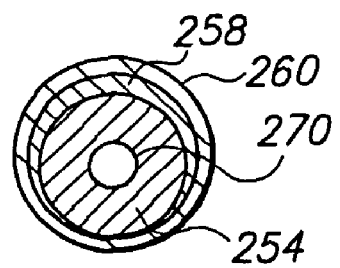
FIG. 40 is a cross-sectional view of the stimulation lead of FIG. 37, taken along the line 40-40.
Figure 41:
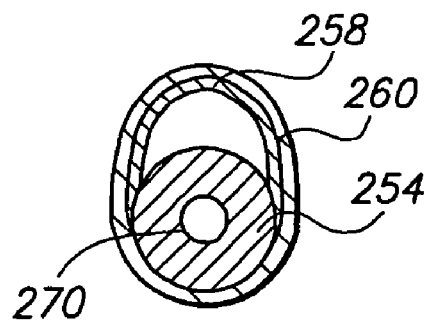
FIG. 41 is a cross-sectional view of the stimulation lead of FIG. 38, taken along the line 41-41.

The proximal adapter 262 comprises a guidewire port 264, an electrical connector 266, and an inflation port 268. As illustrated in FIG. 39, the catheter 252 has a guidewire lumen 270, signal wire lumen 272, and inflation lumen 276 longitudinally extending through the catheter body 254. The guidewire lumen 270 is capable of receiving a guidewire (not shown). The signal wire lumen 272 houses signals wires 274, which distally terminate at the electrodes 256 and proximally terminate in the electrical connector 266 on the proximal adapter 262. Inflation medium may be conveyed into the inflation port 268 on the proximal adapter 262, through the inflation lumen 276, and into the interior of the balloon 258 in order to place the balloon 258 into its expanded state.

In alternative embodiments, a self-expanding stent similar to any one of a variety of well-known self-expanding vascular stents, may be employed. In this case, a balloon is not required.

Figure 42A:
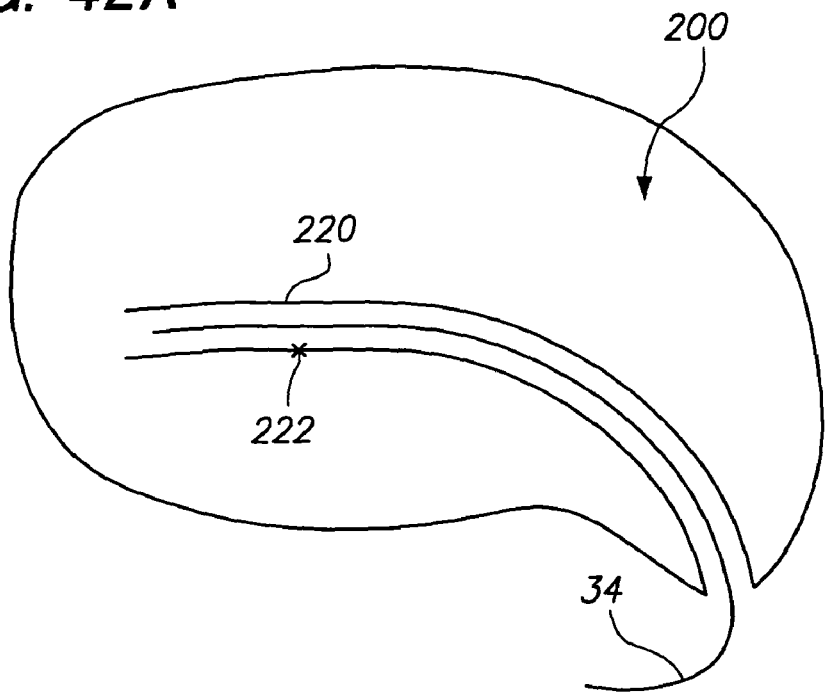
Figure 42B:
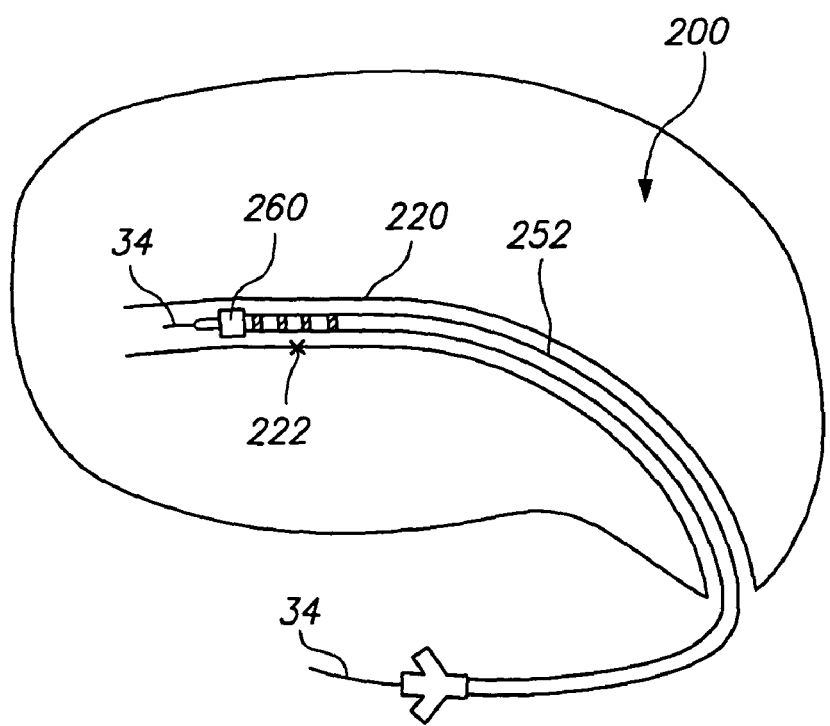

A method of delivering the catheter 252 into a selected cerebral blood vessel 220 of the brain 200 will now be described with respect to FIGS. 42A-42D. Like in the previous methods, a guidewire 34 is routed into a cerebral blood vessel 220 distal to a selected stimulation site 222 (FIG. 42A). The jugular vein or femoral vein, for examples, can be used as the access point into the patient's vasculature. Once proper placement of the guidewire 34 is achieved, the catheter 252 is threaded over the proximal end of the guidewire 34, and the catheter 252, while the balloon 258 is in its deflated state, is distally advanced up the guidewire 34 until the distal end of the catheter 252 is adjacent the selected stimulation site 222 (FIG. 42B). Next, inflation medium is conveyed through into inflation port 268 of the proximal adapter 262, such that the balloon 258 is placed into its expanded state (FIG. 42C). As shown, the free side of the stent 260 has expanded against one side of the vessel wall, thereby urging the distal end of the catheter 252, and more importantly, the electrodes 256, against the opposite side of the vessel wall. The guidewire 34 is then removed from the catheter 252, and thus, the patient's body, and the balloon 258 is deflated by removing the inflation medium from the interior of the balloon 258 out of the inflation port 268 of the proximal adapter 262 (FIG. 42D). As shown, the stent 260 remains expanded, such that the electrodes 256 are chronically urged against the vessel wall. Significantly, contraction of the balloon 258 allows the blood to flow through the stent 260. The electrical connector 266 on the proximal adapter 262, which extends from the patient's body (e.g., from the access point of the jugular vein or femoral vein), is then connected to the implanted stimulation source 14 (not shown).

Figure 43:
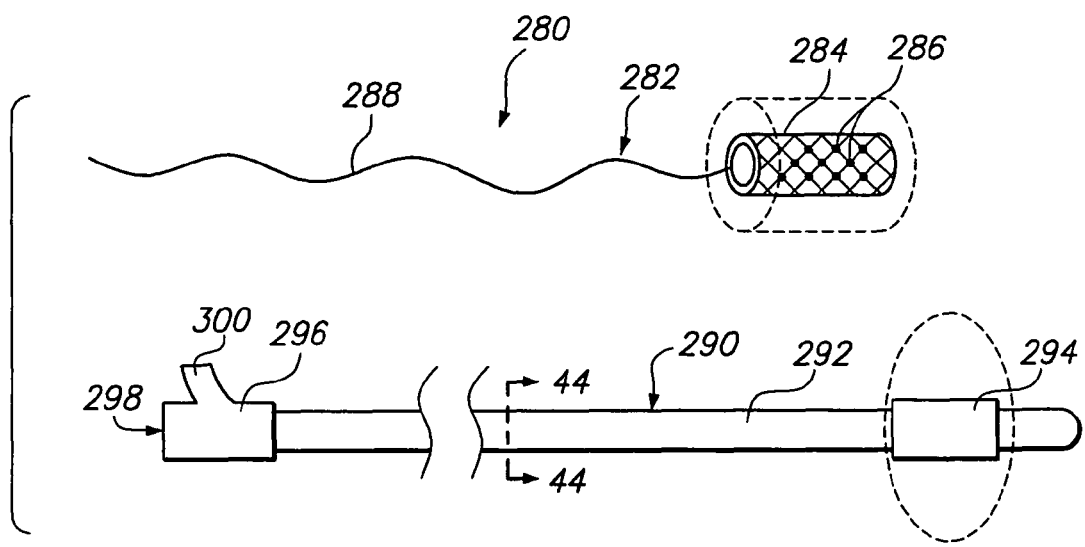
FIG. 43 is a perspective view of still another brain stimulation kit arranged in accordance with a preferred embodiment of the present invention.

Referring to FIG. 43, a delivery kit 280 that includes a stimulation lead 282 with an expandable electrode stent 284 will now be described. The body of the electrode stent 284 has a design similar to well-known expandable vascular stents that are employed to enlarge a restricted vein or artery. The electrode stent 284 comprises a plurality of electrodes 286 that are suitably mounted, e.g., by soldering or welding, to the body of the stent 284. The stimulation lead 282 comprises a signal wire 288 that is similar in construction to the signal wire 16 of the previously described stimulation lead 12. The signal wire 288 is electrically coupled to the electrodes 286 of the stent 284, such that the electrodes 286 can be operated in a monopolar mode. Alternatively, the multiple signal wires 288 can be coupled to the electrodes 286, such that the electrodes 286 can be operated in a bipolar mode.

The delivery kit 280 comprises a balloon catheter 290 that is configured to deliver the stimulation lead 282 to a selected stimulation site within a cerebral blood vessel using a balloon catheter 290. The catheter 290 comprises an elongate, flexible, catheter body 292, an inflatable balloon 294 mounted on the distal end of the catheter body 292, and a proximal adapter 296 mounted on the proximal end of the catheter body 292. The catheter body 292 can have the same dimensions and be composed of the same material as the previously described catheter body 44. The proximal adapter 296 comprises a guidewire port 298 and an inflation port 300. The balloon 294 is of similar construction as the previously described balloon 258, and is circumferentially mounted to the distal end of the catheter 290, such that the balloon 294 will expand radially outward in all directions (shown in phantom in FIG. 43) when an inflation medium is introduced into the balloon 294. The stent 284 can be placed around the deflated balloon 294, such that expansion of the balloon 294 will radially expand the stent 284 (shown in phantom in FIG. 43).

Figure 44:
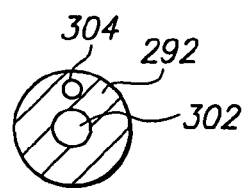
FIG. 44 is a cross-sectional view of a delivery catheter used in the stimulation kit of FIG. 43, taken along the line 44-44.

Referring to FIG. 44, the catheter 290 has a guidewire lumen 302 and inflation lumen 304 longitudinally extending through the catheter body 292. The guidewire lumen 302 is capable of receiving a guidewire (not shown). Inflation medium may be conveyed into the inflation port 300, through the inflation lumen 304, and into the interior of the balloon 294 in order to place the balloon 294 in its expanded state.

In alternative embodiments, a self-expanding stent similar to any one of a variety of well-known self-expanding vascular stents, may be employed. In this case, a balloon is not required.

Figure 45A:
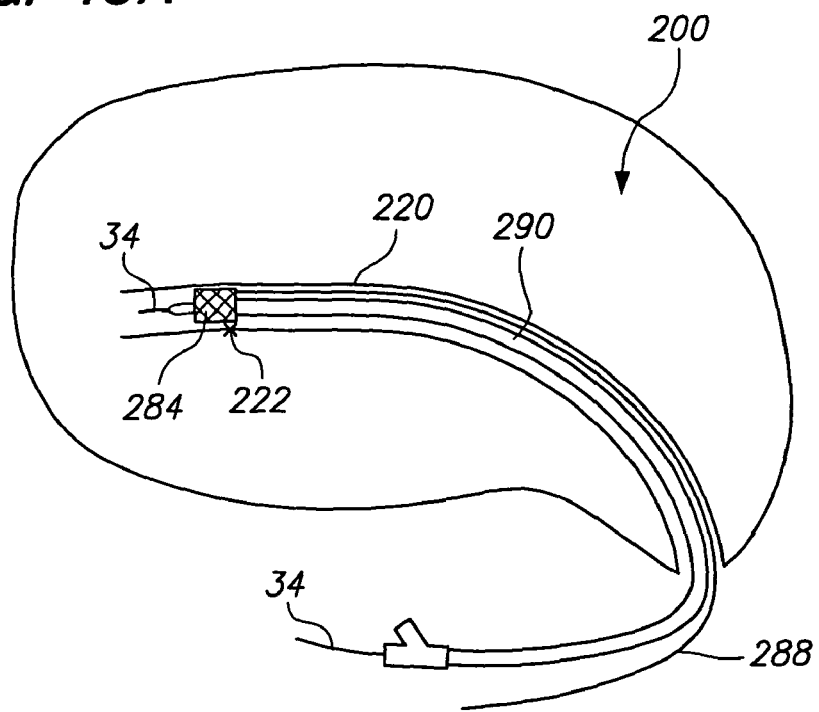
FIGS. 45A-45C are side views illustrating a method of intravascularly delivering a stimulation lead into a cerebral blood vessel within the brain of a patient using the kit of FIG. 43.
Figure 45B:
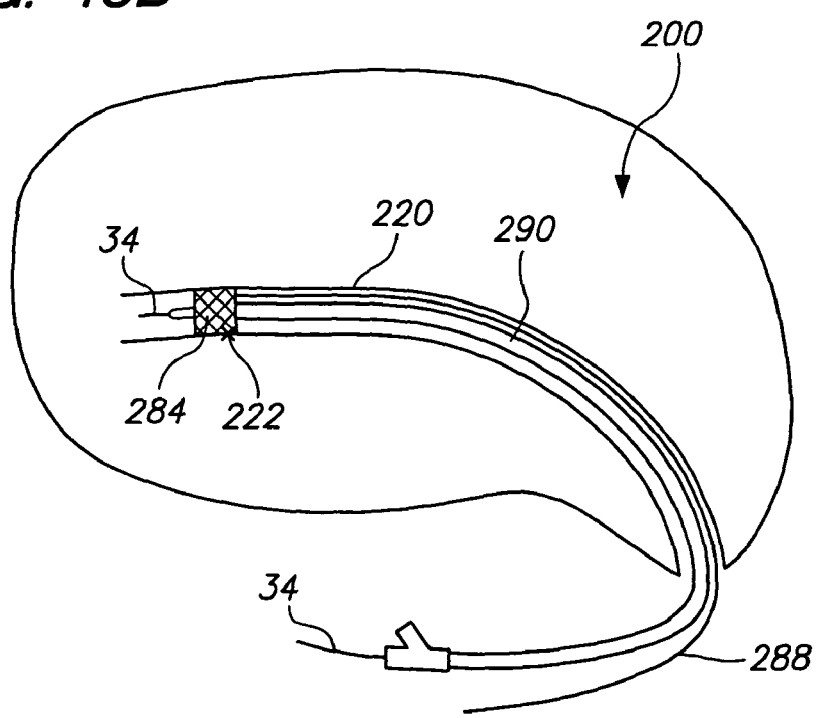
Figure 45C:
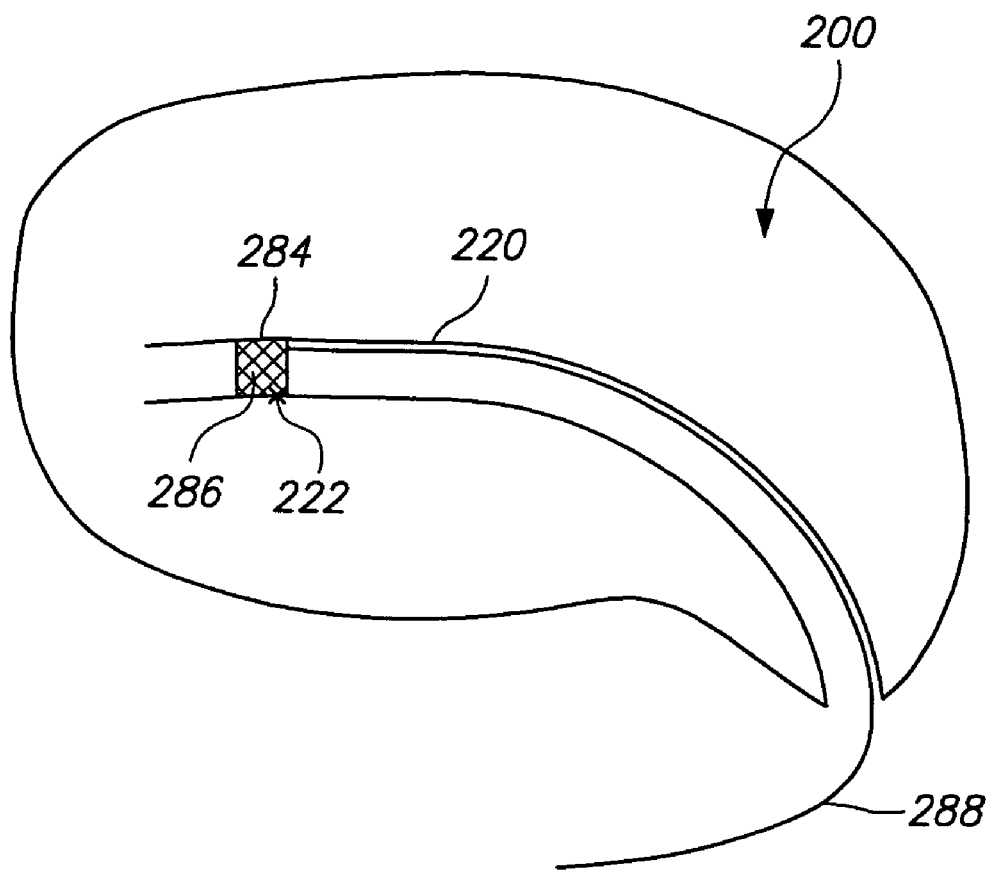

A method of delivering the stimulation lead 12 into a selected cerebral blood vessel 220 will now be described with respect to FIGS. 45A-45C. Once proper placement of the guidewire 34 is achieved (as shown in FIG. 43A), the delivery catheter 290 is threaded over the proximal end of the guidewire 34, and the catheter 290, while the stent 284 is placed over the deflated balloon 294, is distally advanced up the guidewire 34 until the distal end of the catheter 290 is adjacent the selected stimulation site 222 (FIG. 45A). Next, inflation medium is conveyed into the inflation port 300 on the proximal adapter 296, such that the balloon 294 (not shown) is placed into its expanded state (FIG. 45B). As shown, the stent 284 has radially expanded against the vessel wall, thereby urging the electrodes 286 against the vessel wall. The balloon 294 is deflated by removing the inflation medium from inflation port 300 on the proximal adapter 296, and the catheter 290, with the guidewire 34, is removed from the patient's body (FIG. 45C). As shown, the stent 284 remains expanded, such that the electrodes 286 are chronically urged against the vessel wall. If additional stimulation leads 12 are to be placed in other selected stimulated sites, the steps performed in FIGS. 45A-45C can be repeated. The proximal end of the stimulation lead (or leads), which extends from the patient's body (e.g., from the access point of the jugular vein or femoral vein), is then connected to the implanted stimulation source 14 (not shown).

Figure 46:
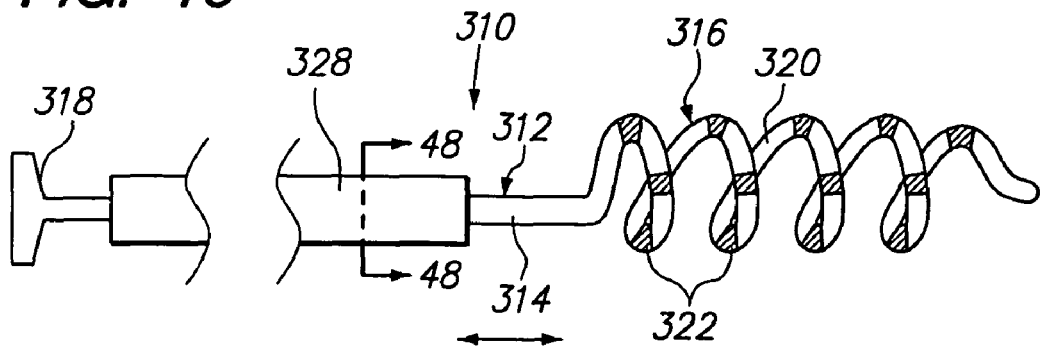
FIG. 46 is a plan view of a stimulation catheter, particularly showing a helical electrode structure in an expanded three-dimensional state.
Figure 47:
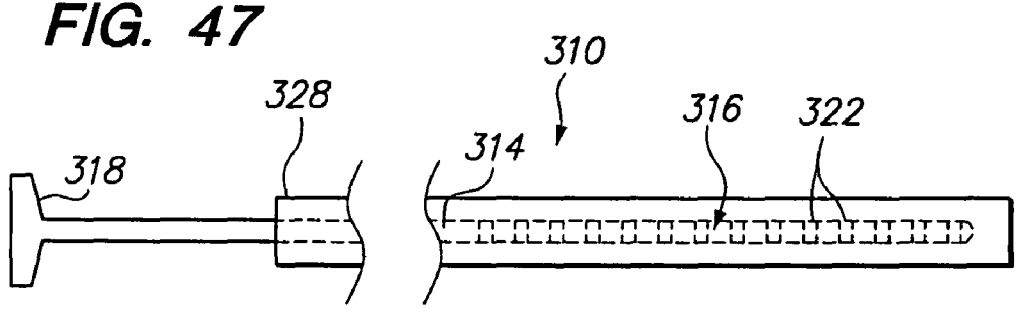
FIG. 47 is a plan view of the stimulation catheter of FIG. 46, particularly showing the helical electrode structure in a compact collapsed state.

Referring to FIGS. 46 and 47, a delivery kit 310 that includes a stimulation lead 312 with a helical electrode structure 316 will now be described. The stimulation lead 312 takes the form of a catheter, which comprises an elongate flexible catheter body 314, the helical electrode structure 316 formed at the distal end of the catheter body 314, and an electrical connector 318 mounted to the proximal end of the catheter body 314. The catheter body 314 can have the same dimensions and be composed of the same material as the previously described delivery catheter 290.

Figure 48:
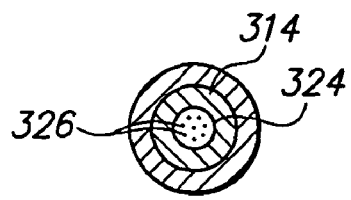
FIG. 48 is a cross-sectional view of the stimulation catheter of FIG. 46, taken along the line 48-48.

The helical electrode structure 316 comprises a resilient helically-shaped member 320 disposed through the distal end of the catheter body 314. The resilient member 320 can be composed of any suitable material that can be pre-shaped into a helical member, such as nitinol. The helically-shaped member 320 carries an array of electrodes 322 that can be applied to the surface of the helically-shaped member 320, e.g., by coating the helical electrode structure with an electrically conductive material. As illustrated in FIG. 48, the catheter 312 comprises a signal wire lumen 324 longitudinally extending through the catheter body 314. The signal wire lumen 324 houses signals wires 326, which distally terminate at the electrodes 322 and proximally terminate in the electrical connector 318.

The delivery kit 310 comprises a slideable guide sheath 328 that is movable along the axis of the catheter body 314 (shown by arrows in FIG. 46). Moving the sheath 328 in the distal direction over the helical electrode structure 316, collapses it into a compact, low profile linear form for introducing into a blood vessel (shown in phantom in FIG. 47). Moving the sheath 328 in the proximal direction away from the helical electrode structure 316, allows it to spring open into stable contact within the blood vessel (FIG. 46).

Figure 49A:
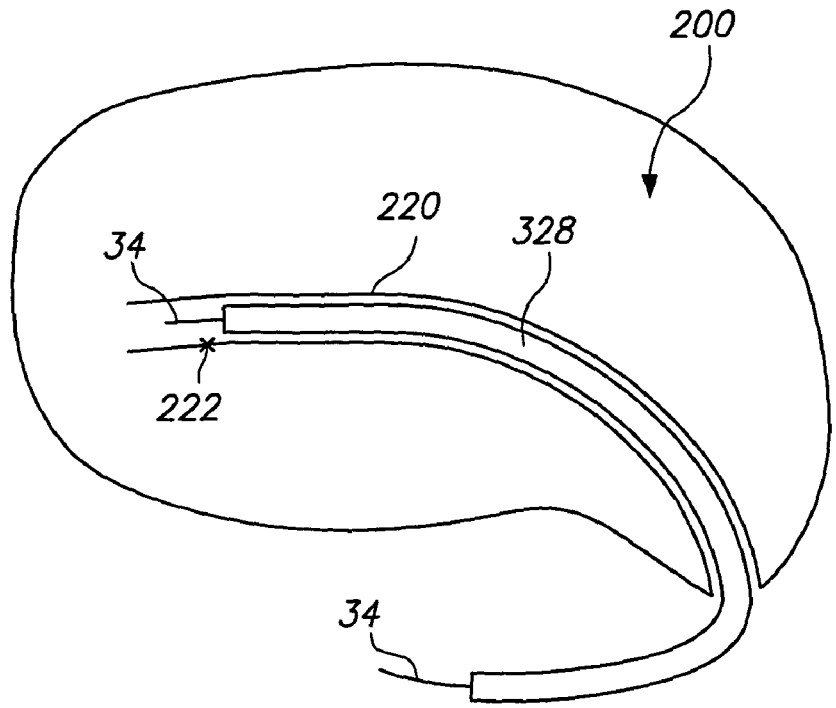
FIGS. 49A-49C are side views illustrating a method of intravascularly delivering the catheter of FIG. 47 into a cerebral blood vessel within the brain of a patient.
Figure 49B:
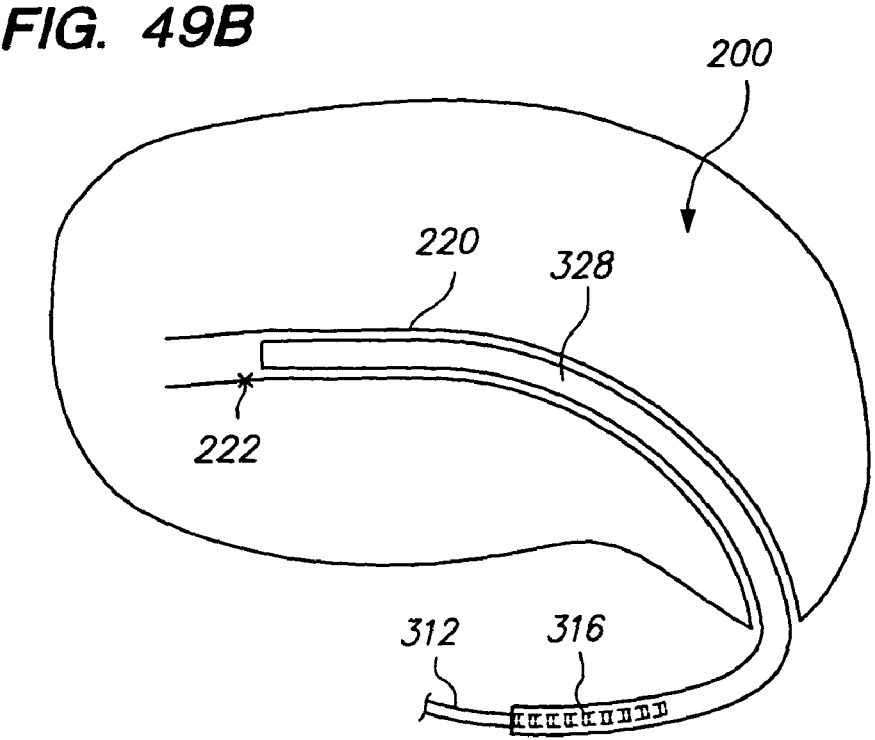
Figure 49C:
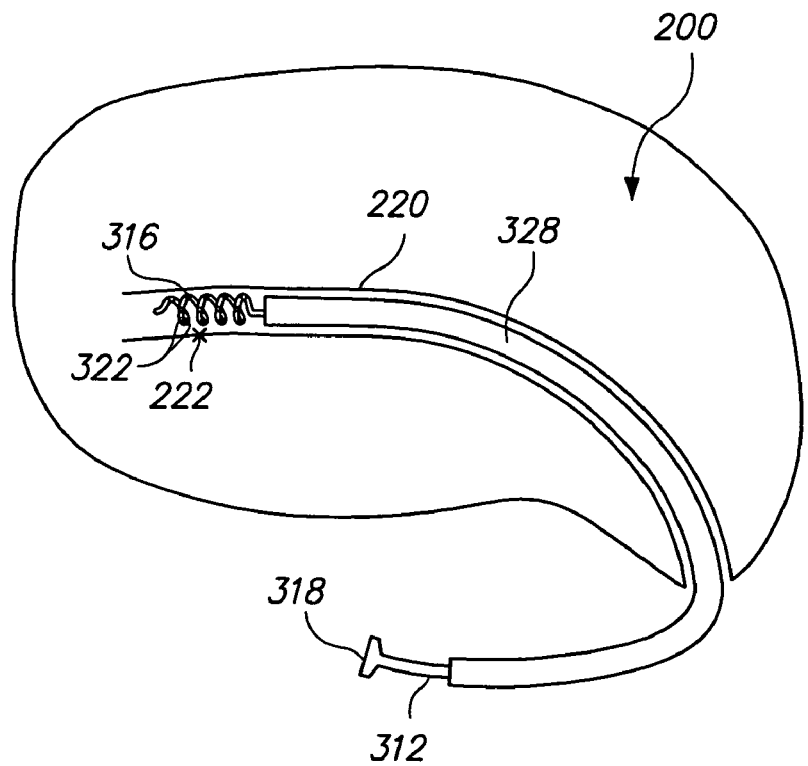

A method of delivering the catheter 312 into a selected cerebral blood vessel 220 will now be described with respect to FIGS. 49A-49D. Once proper placement of the guidewire 34 is achieved (as shown in FIG. 43A), the guide sheath 328 is distally advanced up the guidewire 34 until the distal end of the guide sheath 328 is located proximal to the selected stimulation site 222 (FIG. 49A). Next, the guidewire 34 is removed from the guide sheath 328, and the helical electrode structure 316 of the catheter 312 is inserted into the proximal end of the guide sheath 328, such that the helical electrode structure 316 is placed into its collapsed linear state (shown in phantom in FIG. 49B). The catheter 312 is then introduced through the guide sheath 328 until the helical electrode structure 316 is deployed from the distal end of the guide sheath 328 into the blood vessel 320 adjacent the stimulation site 222 (FIG. 49C). As illustrated, the helical electrode structure 316 assumes its three-dimensional expanded state, such that the electrodes 322 are placed into stable contact with the blood vessel 320. The guide sheath 328 is then removed from the patient's body, and the electrical connector 318 of the catheter 312, which extends from the patient's body (e.g., from the access point of the jugular vein or femoral vein), is then connected to the implanted stimulation source 14 (not shown). Depending on the configuration of the electrodes 322 and the connection to the stimulation source 14, the brain tissue surrounding the stimulation site 222 of the blood vessel 220 can be electrically stimulated in a monopolar or bipolar mode.

The previously described embodiments and methods provided electrical stimulation of the brain tissue through a vessel wall (i.e., the electrode(s) were in indirect contact with the brain tissue, and thus stimulated the brain tissue through blood and vascular tissue). The brain tissue can be directly stimulated, however, by introducing the electrodes through a puncture site within the blood vessel, and then placing the electrodes into direct contact with the brain tissue.

Figure 50:
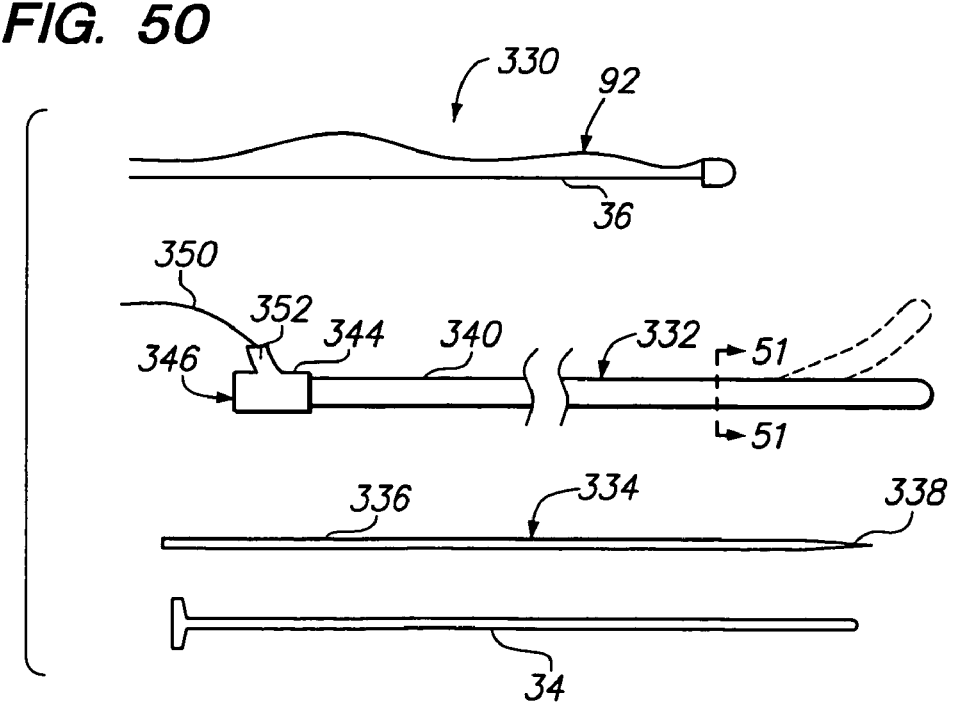
FIG. 50 is a plan view of yet another brain stimulation kit arranged in accordance with a preferred embodiment of the present invention.

For example, referring to FIG. 50, a brain stimulation delivery kit 330 arranged in accordance with another preferred embodiment of the present invention will now be described. The kit 330 comprises the previously described stimulation lead 92 and associated pusher element 36, the previously described guidewire 34, a delivery catheter 332, and a stylet 334. As previously described, the stimulation lead 92 comprises an electrode 96 with a lumen 98 that allows the electrode 96 to longitudinally slide along a shaft, and in this case, the stylet 334.

Figure 51:
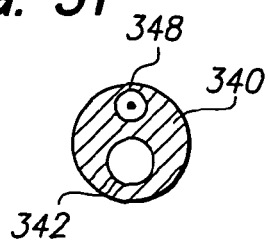
FIG. 51 is a cross-sectional view of the delivery catheter used in the stimulation kit of FIG. 50, taken along the line 51-51.

The stylet 334 comprises a laterally flexible, yet axially rigid, shaft 336 and a sharpened distal tip 338 that is capable of penetrating tissue, and in particular, vascular tissue. Alternatively, other tissue penetrating devices, such as lasers, can be used to penetrate through vascular tissue. The delivery catheter 332 comprises an elongate, flexible, catheter body 340 and a guidewire lumen 342 (shown in FIG. 51) longitudinally extending through the catheter body 340. The guidewire lumen 342 is configured to singly receive the guidewire 34, stylet 334, and stimulation lead 92. The delivery catheter 332 further comprises a proximal adapter 344 suitably mounted on the proximal end of the catheter body 340. The proximal adapter 344 comprises a guidewire port 346 out which the guidewire 34 may extend when the delivery catheter 332 is introduced over the guidewire 34. The guidewire port 346 also serves as a port through which the stimulation lead 92 can be introduced through the delivery catheter 332.

The catheter body 340 may be composed of the same material and have the same dimensions as the previously described catheter body 44. Unlike the catheter body 44, however, the distal end of the catheter body 340 is configured to be deflected at an obtuse or perpendicular angle relative to the general axis of the catheter body 340. In the illustrated embodiment, the distal end of the catheter body 340 is deflected using pull wire technology. In particular, the catheter 332 comprises a pullwire lumen 348 that longitudinally extends through the catheter body 340 (shown in FIG. 51), and the proximal adapter 340 further comprises a pullwire port 352. The pullwire lumen 348 houses a pullwire 350, which is suitably attached to the distal end of the catheter body 340, and proximally extends out from the pullwire port 352 on the proximal adapter 340. Thus, it can be appreciated that pulling the pullwire 350 in the proximal direction will, in turn, laterally deflect the distal end of the catheter body 350, as shown in phantom in FIG. 50.

The distal end of the catheter body 340 can be deflected using other technologies. For example, the distal end of the catheter body 340 can be composed of a super-elastic alloy, such as Nitinol, that deforms when exposed to body temperature. In this case, the catheter 332 is preferably delivered to the vessel using a guide sheath (not shown), such that the distal end of the catheter body 340 is not exposed to body temperature, and thus, maintains its straight geometry during introduction through the patient's vasculature.

Referring now to FIGS. 52A-52H, the kit 330 can be used to deliver the stimulation lead 92 into the sub-arachnoid space 228 of the patient's head, thereby allowing the electrode 96 of the stimulation lead 92 to be more freely placed anywhere along the cortex 202 of the brain 200.

Figure 52A:
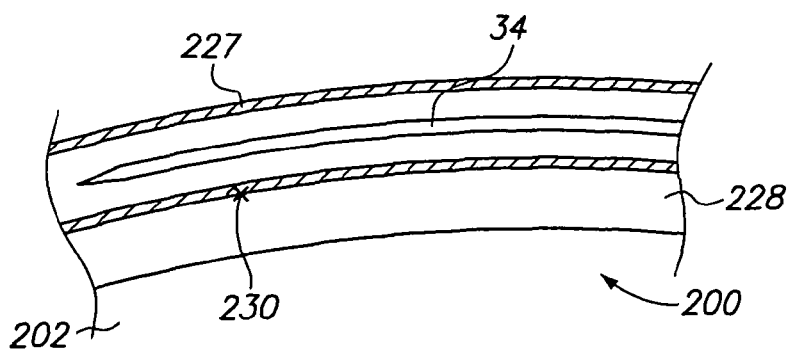
FIGS. 52A-52H are side views illustrating a method of intravascularly delivering a stimulation lead within the subarachnoid space of a patient using the kit of FIG. 50.
Figure 52B:
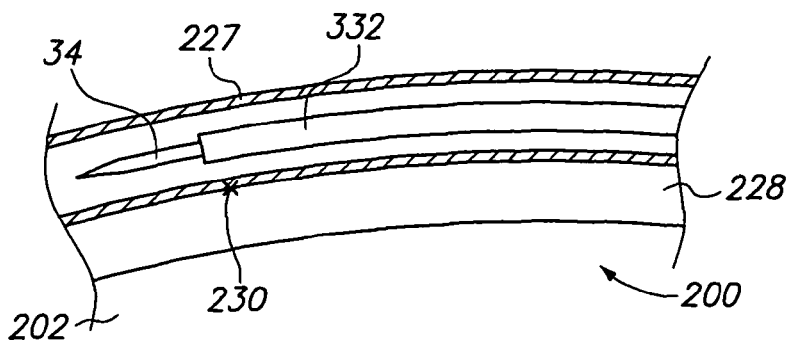
Figure 52C:
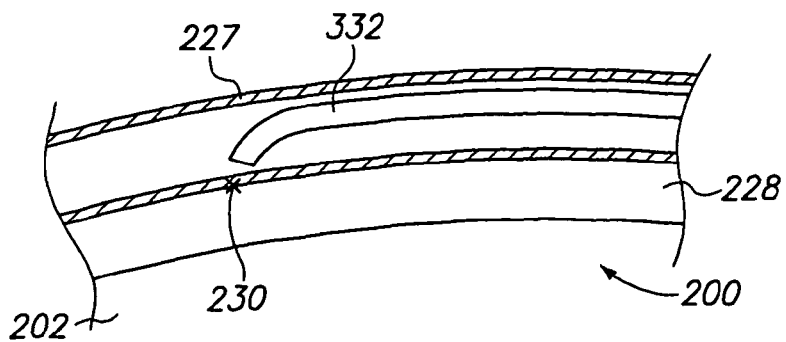

First, the guidewire 34 is routed into a superficial blood vessel 227 adjacent the sub-arachnoid space 228 (e.g., a superior cerebral vein branching off of the superior sagittal sinus) until the distal end of the guidewire 34 is distal to a selected puncture site 230 (FIG. 52A). The jugular vein or femoral vein, for examples, can be used as the access point into the patient's vasculature. Once proper placement of the guidewire 34 is achieved, the delivery catheter 332 is threaded over the proximal end of the guidewire 34, and distally advanced up the guidewire 34 until the distal end of the catheter 332 is adjacent the selected puncture site 230 (FIG. 52B). Next, the guidewire 34 is removed from the catheter 332 via the guidewire port 346 on the proximal adapter 340 (not shown), and the pull wire 350 extending from the pullwire port 352 on the proximal adapter 340 (not shown) is pulled in the proximal direction in order to deflect the distal end of the catheter body 340 towards the selected puncture site 230 (FIG. 52C). Alternatively, if the distal end of the catheter body 340 is composed of a super-elastic alloy, the distal end of the catheter body 340 will automatically deflect upon exiting a guide sheath (not shown).

Figure 52D:
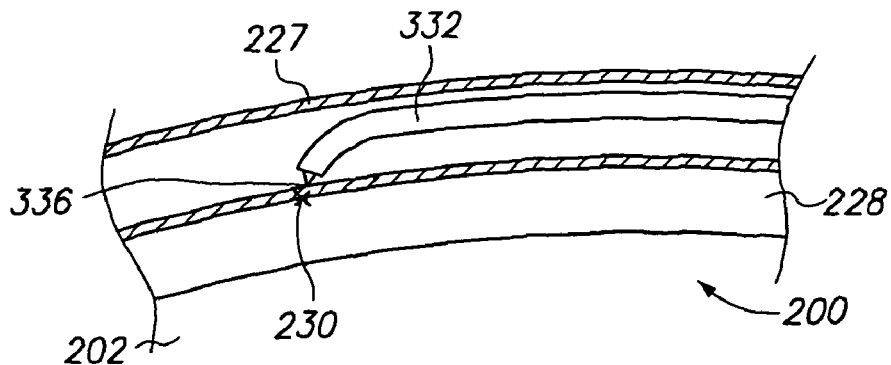
Figure 52E:
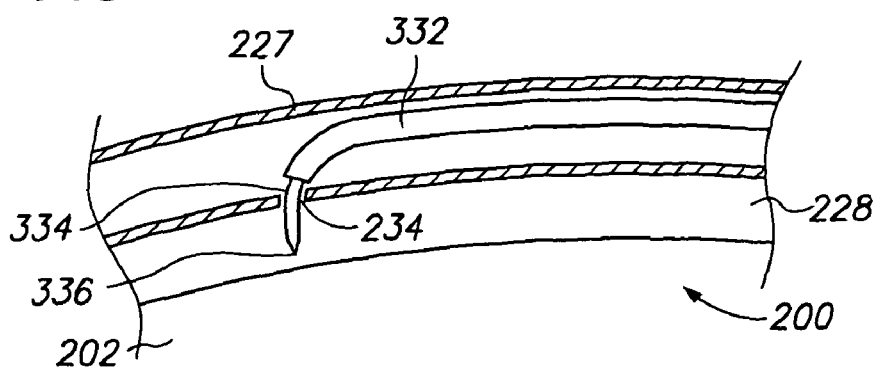
Figure 52F:
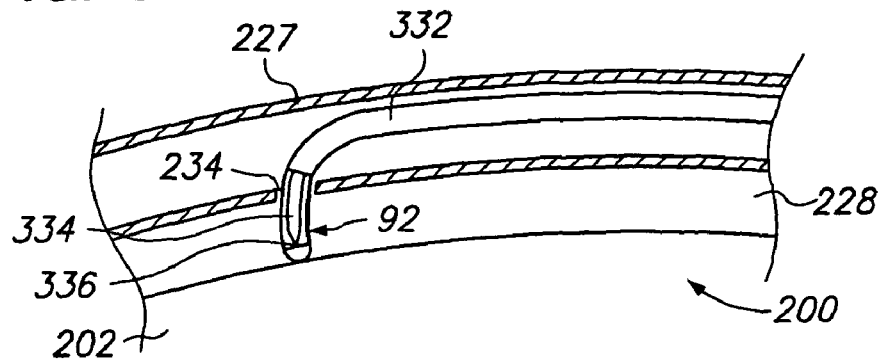
Figure 52G:
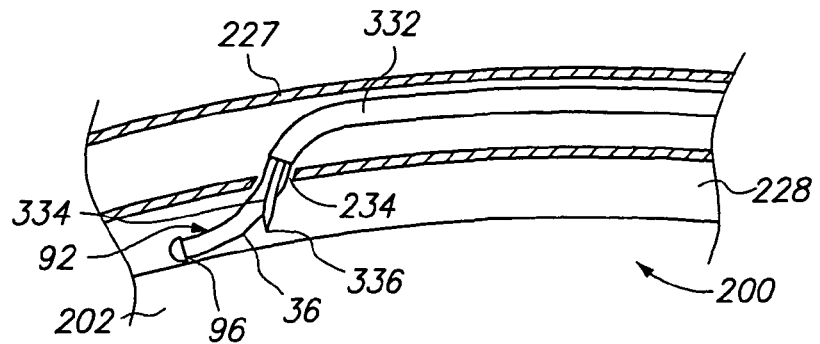

Next, the stylet 334 is introduced into the guidewire port 346 on the proximal adapter 340 (not shown) and through the catheter body 340 until the distal end of the stylet 334 deploys out from the distal end of the catheter body 340 (FIG. 52D). As shown, the deflection of the distal end of the catheter body 340 has angled the sharpened distal tip 336 of the stylet 334 towards the wall of the vessel 230. Further advancement of the stylet 334 will then cause the distal tip 336 to puncture the vessel wall, thereby forming an exit point 234 into the surrounding brain tissue. (FIG. 52E). The electrode 96 of the stimulation lead 92 is then threaded over the stylet 334, and, by pushing the pusher element 36, distally advanced up the stylet 334, through the exit point 234 in the vessel wall, and into contact with the surrounding brain tissue (FIG. 52F). In this case, the stimulation lead 92 will be placed into the sub-arachnoid space 228 in contact with the exterior of the cortex 202. Manipulation of the pusher element 36 allows the electrode 96 to be navigated within the sub-arachnoid space 228, so that it can be placed in direct contact with a selected stimulation site 232 on the cortex 202 (FIG. 52G). In some cases, it may be desirable to introduce a stimulation lead through a lumen (not shown) within the stylet 334, rather than over the stylet 334. In this manner, any seal created between the stylet 334 and the exit point 234 in the vessel wall can be more easily maintained. Whichever way the stimulation lead is delivered, the stylet 334 can be provided with steering functionality (e.g., by having a torqueable or bendable distal tip), in which case, manipulation of the stylet 334 will aid in proper placement of the electrode 96. Once the electrode 96 is properly placed, the pusher element 36 can then be electrolytically detached from the electrode 96 and removed from the delivery catheter 332 (FIG. 52H).

Figure 52H:
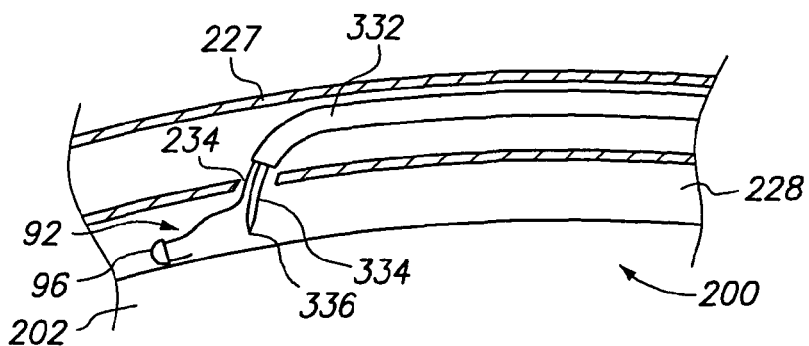

If additional stimulation leads 12 are to be placed in other selected stimulated sites, the steps performed in FIGS. 52F-52H can be repeated. The delivery catheter 332, along with the stylet 334, is then removed from the patient, and the proximal end of the stimulation lead (or leads), which extends from the patient's body (e.g., from the access point of the jugular vein or femoral vein), is then connected to the implanted stimulation source 14 (not shown).

It is believed that exiting the venous system, which has relatively low blood pressures, rather than the arterial system, which has relatively high blood pressures, may limit bleeding through the fenestrated vessel. If navigation through the arterial system is desired, however, the meningeal arteries may be used to provide an exit point, since intra-mennegies bleeds are considered much less risky than those that would otherwise be caused by creating exit points in other intra-cranial arteries, such as those branching off of the vertebral artery or internal carotid artery. In whichever vessel the exit point is created, the distal end of the stimulation lead 92, which will ultimately be left within the patient's body, may be coated with a thrombogenic material in order to minimize the loss of blood through the exit point. Optionally, the blood flow through the fenestrated vessel can be minimized by totally or partially occluding the flow of blood through the vessel using a balloon apparatus. Of course, the extent to which the fenestrated vessel is occluded and time of the occlusion should be carefully monitored to minimize the risk of stroke. Notably, if a meningeal artery, which has a superfluous blood flow, is used, the risk of stroke will be further minimized.

Figure 53:
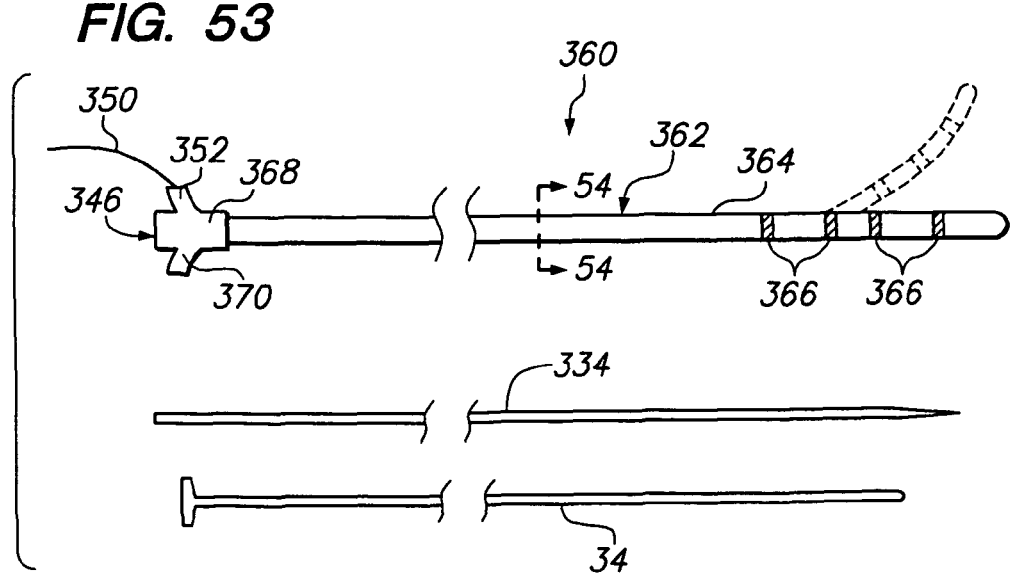
FIG. 53 is a plan view of yet another brain stimulation kit arranged in accordance with a preferred embodiment of the present invention.

Other types of the stimulation leads can be delivered into direct contact with brain tissue via fenestrated blood vessels. For example, FIG. 53 illustrates a brain stimulation delivery kit 360 arranged in accordance with another preferred embodiment of the present invention. The kit 360 comprises a stimulation lead 362, which takes the form of a catheter, and the previously described guidewire 34 and stylet 334. The catheter 362 is similar to the previously described delivery catheter 332, with the exception that the catheter 362 additionally comprises electrical stimulation capability.

In particular, the catheter 362 comprises an elongate, flexible, catheter body 364, a plurality of ring electrodes 366, and a proximal adapter 368 mounted on the proximal end of the catheter body 364. The catheter body 364 can have the same dimensions and be composed of the same material as the previously described catheter body 44. The proximal adapter 368 comprises the previously described guidewire port 346 and pullwire port 352, as well as an electrical connector 370.

Figure 54:
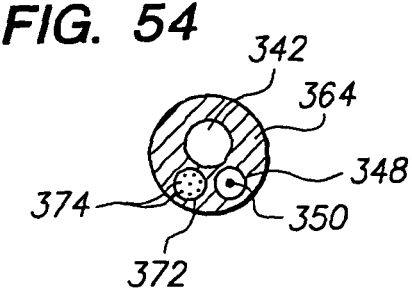
FIG. 54 is a cross-sectional view of the delivery catheter used in the stimulation kit of FIG. 53, taken along the line 54-54.

In addition to the previously described guidewire lumen 342 and pullwire lumen 348 in which there are disposed a guidewire (not shown) and a pullwire 350, respectively, the catheter 362 further comprises a signal wire lumen 372 longitudinally extending through the catheter body 364, as illustrated in FIG. 54. The signal wire lumen 372 houses a plurality of signal wires 374 that distally terminate at the respective electrodes 366 and proximally terminate in the electrical connector 370 on the proximal adapter 368.

Figure 55A:
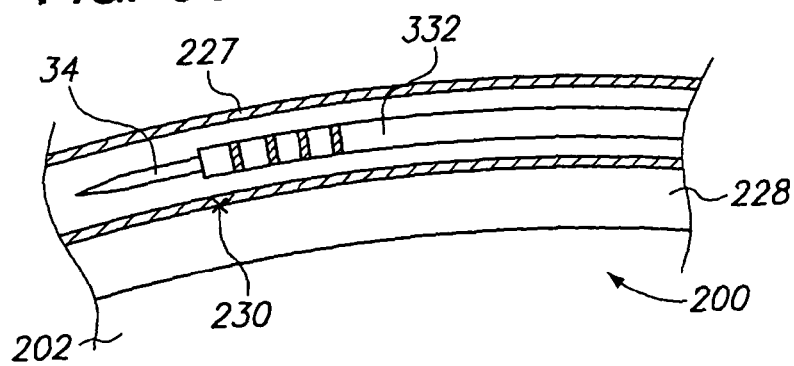
FIGS. 55A-55D are side views illustrating a method of intravascularly delivering a stimulation lead within the subarachnoid space of a patient using the kit of FIG. 53.
Figure 55B:
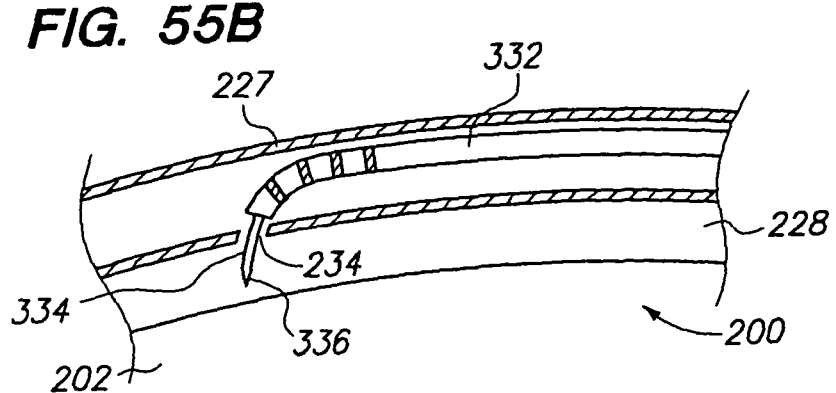
Figure 55C:
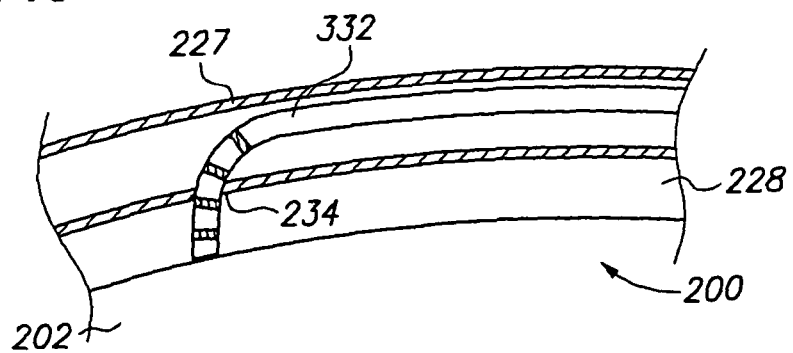
Figure 55D:
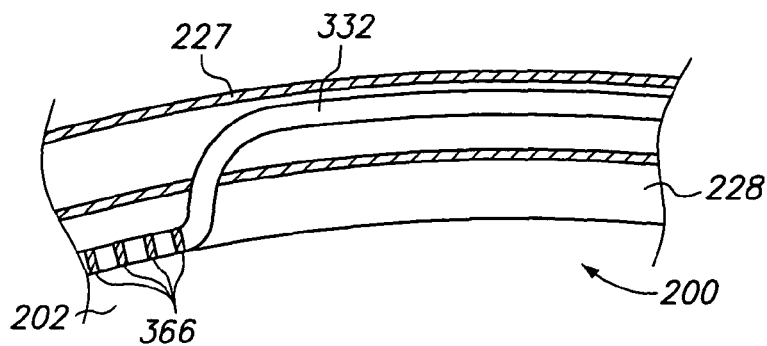

Referring now to FIGS. 55A-55D, the kit 360 can be used to deliver the catheter 362 into the sub-arachnoid space 228 of the patient's head, thereby allowing the electrodes 366 of the catheter 362 to be more freely placed anywhere along the cortex 202 of the brain 200. Once proper placement of the guidewire 34 is achieved (as shown in FIG. 53A), the catheter 332 is threaded over the proximal end of the guidewire 34, and distally advanced up the guidewire 34 until the distal end of the catheter 332 is adjacent the selected puncture site 230 (FIG. 55A). Next, in the same manner described above in FIGS. 52C-52E, the distal tip 336 of the stylet 334 is deployed from the catheter 332 and into the sub-arachnoid space 228, creating an exit point 234 through the vessel wall (FIG. 55B). The distal end of the catheter 332 is then advanced over the stylet 334, through the exit point 234 in the vessel wall, and into the sub-arachnoid space 228 in contact with the exterior of the cortex 202 (FIG. 55C). The distal end of the catheter 332 can then be navigated within the sub-arachnoid space 228, so that the electrodes 366 can be placed in direct contact with a selected stimulation site 232 on the cortex 202 (FIG. 55D). Alternatively, the catheter 332 or stylet 334 can be provided with steering functionality, in which case, steering of the catheter 332 or stylet 334 will aid in proper placement of the electrodes 366. Once the electrodes 366 have been properly placed, the stylet 334 is then removed from the patient's body. If steering functionality is not provided to the catheter 332, the distal end of the catheter 332 is preferably composed of a malleable material, such that the catheter 332 retains its shape, and thus, the electrodes 366 remain at their desired locations, when the stylet 334 is removed. If additional catheters 362 are to be placed in other selected stimulated sites, the steps performed in FIGS. 55A-55D can be repeated. The proximal end of the catheter (or catheters), which extends from the patient's body (e.g., from the access point of the jugular vein or femoral vein), is then connected to the implanted stimulation source 14 (not shown).

As with the distal end of the previously described stimulation lead 92, the distal end of the catheter body 364 is preferably coated with a thrombogenic material in order to minimize the loss of blood through the exit point. Alternatively, the distal end of the catheter body 364 may be provided with a radially expanding mechanism, such as a balloon and/or stent, or a radially expanding substance, such as hydrogel, such that the exit point will be sealed with the distal end of the catheter body 364 upon expansion of the mechanism or substance. Or, alternatively, the catheter body 364 can be provided within an ablative element, such as an ablation electrode, the operation of which will cauterize the exit point. As previously described, the blood flow through the fenestrated vessel can be minimized by totally or partially occluding the flow of blood through the vessel using a balloon apparatus.

Figure 56:
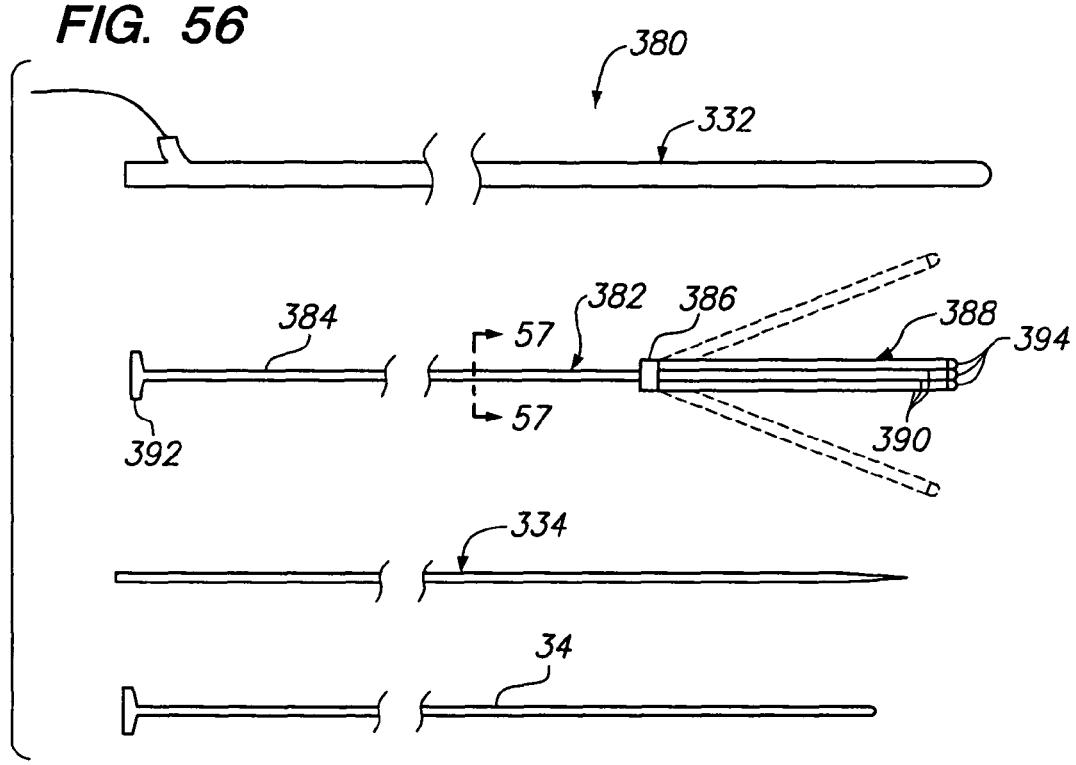
FIG. 56 is a plan view of yet another brain stimulation kit arranged in accordance with a preferred embodiment of the present invention.

Referring to FIG. 56, a brain stimulation delivery kit 380 arranged in accordance with still another preferred embodiment of the present invention will now be described. The kit 380 comprises an arrayed stimulation lead 382, and the previously described guidewire 34, delivery catheter 332, and stylet 334.

The arrayed stimulation lead 382 comprises a laterally flexible, yet axially rigid, shaft 384, a base member 386, an array structure 388 formed of a plurality of flexible stimulation leads or splines 390 connected to the base member 386, and an electrical connector 392 mounted to the proximal end of the shaft 384. The splines 388 are preferably made of a resilient inert material, like Nitinol metal or stainless steel. Thus, the array structure 388 can be alternately placed into a compact, collapsed low-profile state in the presence of a compressive force, and a two-dimensional fanned state (shown in phantom) in the absence of a compressive force. In the illustrated embodiment, three splines 390 form the array structure 388. Additional or fewer splines 390, however, could be used to form the array structure 388. Each spline 390 carries an electrode 394 at its distal end. Of course, additional electrodes 392 can be used. The electrodes 394 can be arranged in a monopolar or a bipolar arrangement.

Figure 57:
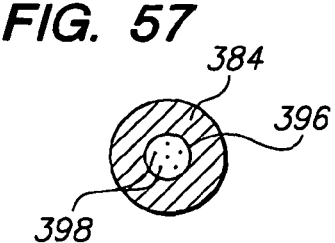
FIG. 57 is a cross-sectional view of the delivery catheter used in the stimulation kit of FIG. 56, taken along the line 57-57.

As illustrated in FIG. 57, the arrayed stimulation lead 382 further comprises a signal wire lumen 396 longitudinally extending through the shaft 384. The signal wire lumen 396 splits off into three separate lumens (not shown) that respectively extend through the splines 390. The signal wire lumen 396 houses signal wires 398, which are distally connected to the electrodes 394 (after passing through the respective lumens within the splines 390) and proximally connected to the electrical connector 392.

The guidewire lumen 342 of the catheter 332 (shown in FIG. 51) is configured to singly receive the guidewire 34, stylet 334, and arrayed stimulation lead 382. Because the arrayed stimulation lead 382 has a larger profile than the previously described stimulation lead 92, the diameter of the guidewire lumen 342 should be larger than that required to receive the stimulation lead 92. In this case, the stimulation lead 382 is preferably deployed from a larger blood vessel, such as the superior or inferior sagittal sinuses.

Referring now to FIGS. 58A-58D, the kit 380 can be used to deliver the stimulation lead 382 into the sub-arachnoid space 228 of the patient's head, thereby allowing the electrodes 392 of the stimulation lead 382 to be more freely placed anywhere along the cortex 202 of the brain 200.

Figure 58A:
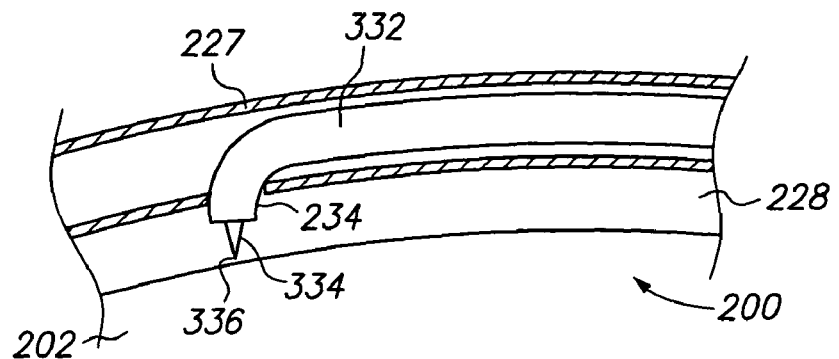
FIGS. 58A-58C are side views illustrating a method of intravascularly delivering a stimulation lead within the subarachnoid space of a patient using the kit of FIG. 56.
Figure 58B:
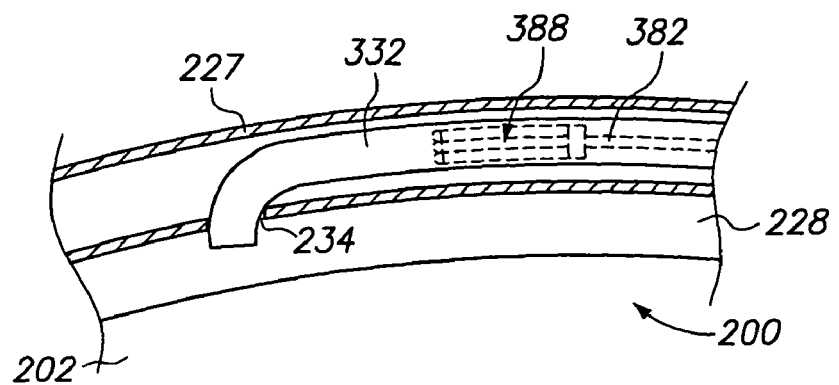
Figure 58C:
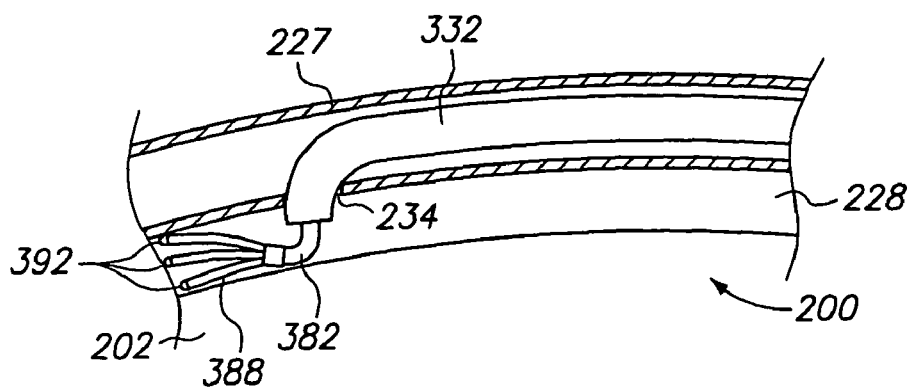

First, the blood vessel 227 is fenestrated in the same manner illustrated in FIGS. 52A-52E to create an exit point 238 at a selected puncture site 236. The distal end of the catheter 332 is then advanced over the stylet 334, through the exit point 234 in the vessel wall, and into the sub-arachnoid space 228 in contact with the exterior of the cortex 202 (FIG. 58A). The stylet 334 is then removed from the catheter 332, and the arrayed stimulation lead 382 is inserted into the guidewire port 346 (not shown), such that the array structure 388 (shown in phantom) of the catheter 332 is placed into its collapsed state (FIG. 58B). The array structure 388 is then introduced through the catheter 332 until the array structure 388 deploys out from the distal end of the catheter body 340 into the sub-arachnoid space 228 (FIG. 58C). As illustrated, the array structure 388 assumes its two-dimensional fanned state, thereby spreading the electrodes 392 across the surface of the cortex 202. The delivery catheter 332 is then removed from the patient, and the proximal end of the stimulation lead, which extends from the patient's body (e.g., from the access point of the jugular vein or femoral vein), is then connected to the implanted stimulation source 14 (not shown).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

The invention claimed is:

1. A method of treating a disorder in a patient, comprising:
   delivering a stimulation lead within a cerebral blood vessel;
   occluding the flow of blood through the blood vessel by selectively actuating an occlusive device;
   intralumenally puncturing a wall of the blood vessel to create an exit point downstream from the actuated occlusive device, wherein blood is prevented from flowing through the exit point; and
   introducing the stimulation lead through the exit point into contact with brain tissue the stimulation of which treats the neurological disorder.

2. The method of claim 1, further comprising stimulating the brain tissue with the stimulation lead to treat the disorder.

3. The method of claim 1, wherein the disorder is a neurological disorder.

4. The method of claim 1, wherein the brain tissue is one of cortical brain tissue and deep brain tissue.

5. The method of claim 1, further comprising advancing the stimulation lead from the exit point along a sub-arachnoid space of the patient's head.

6. The method of claim 1, wherein the vessel wall is intralumenally punctured by introducing a guide element through the vessel wall, and the stimulation lead is introduced through the exit point by introducing the stimulation lead along the guide element.

7. The method of claim 6, further comprising:
   introducing a catheter having a distal end into the blood vessel; and
   deflecting the distal end of the catheter towards the vessel wall at an obtuse or perpendicular angle;
   wherein the guide element is introduced from the deflected distal end of the catheter through the vessel wall.

8. The method of claim 7, wherein the catheter comprises the stimulation lead.

9. The method of claim 1, further comprising sealing the exit point after the stimulation lead has been introduced through the exit point.

10. The method of claim 1, wherein the stimulation lead is an arrayed stimulation lead.

11. The method of claim 1, wherein the flow of blood through the blood vessel is totally occluded.

12. The method of claim 1, wherein the flow of blood through the blood vessel is partially occluded.

13. The method of claim 1, wherein the occlusive device is a balloon, and the blood flow is occluded by inflating the balloon.

14. The method of claim 1, wherein the occlusive device is an ablative element, and the blood flow is occluded by ablating the blood vessel.

15. The method of claim 1, wherein the occlusive device is mounted to the stimulation lead.

16. A method of treating a disorder in a patient, comprising:
   delivering a stimulation lead within a cerebral blood vessel;
   intralumenally puncturing a wall of the blood vessel to create an exit point;
   introducing the stimulation lead through the exit point;
   advancing the stimulation lead from the exit point in a plane of a sub-arachnoid space of the patient's head, the plane extending along a surface of the cortex of the patient's brain; and
   placing the stimulation lead into contact with brain tissue the stimulation of which treats the disorder.

17. The method of claim 16, wherein the disorder is a neurological disorder.

18. The method of claim 16, further comprising stimulating the tissue with the stimulation lead to treat the disorder.

19. The method of claim 16, wherein the vessel wall is intralumenally punctured by introducing a guide element through the vessel wall, and the stimulation lead is introduced through the exit point by introducing the stimulation lead along the guide element.

20. The method of claim 19, further comprising:
   introducing a catheter having a distal end into the blood vessel; and
   deflecting the distal end of the catheter towards the vessel wall at an obtuse or perpendicular angle;
   wherein the guide element is introduced from the deflected distal end of the catheter through the vessel wall.

21. The method of claim 20, wherein the catheter comprises the stimulation lead.

22. The method of claim 16, further comprising occluding the flow of blood through the blood vessel upstream from the exit point.

23. The method of claim 16, further comprising sealing the exit point after the stimulation lead has been introduced through the exit point.

24. The method of claim 16, wherein the stimulation lead is an arrayed stimulation lead.

25. The method of claim 24, wherein the arrayed stimulation lead comprises an array structure formed of a plurality of flexible stimulation splines.

26. The method of claim 25, wherein each of the flexible stimulation splines carries an electrode.

27. The method of claim 25, wherein the plurality of flexible stimulation splines comprises at least three flexible stimulation splines.

28. The method of claim 25, further comprising:
   placing the array structure in a collapsed state while delivering the stimulation lead within the cerebral blood vessel; and placing the array structure in a two-dimensional fanned state after advancing the stimulation lead from the exit point, thereby spreading the flexible splines across the surface of the cortical tissue.

29. The method of claim 16, wherein the brain tissue is cortical tissue.

30. A method of treating a disorder in a patient, comprising:
delivering a stimulation lead within a cerebral blood vessel;
intralumenally puncturing a wall of the blood vessel to create an exit point;
sealing the exit point after the stimulation lead has been introduced through the exit point by activating a sealing mechanism associated within the stimulation lead; and
introducing the stimulation lead through the exit point into contact with brain tissue the stimulation of which treats the neurological disorder.

31. The method of claim 30, further comprising stimulating the brain tissue with the stimulation lead to treat the disorder.

32. The method of claim 30, wherein the disorder is a neurological disorder.

33. The method of claim 30, wherein the brain tissue is one of cortical brain tissue and deep brain tissue.

34. The method of claim 30, wherein the vessel wall is intralumenally punctured by introducing a guide element through the vessel wall, and the stimulation lead is introduced through the exit point by introducing the stimulation lead along the guide element.

35. The method of claim 30, further comprising:
introducing a catheter having a distal end into the blood vessel; and
deflecting the distal end of the catheter towards the vessel wall at an obtuse or perpendicular angle;
wherein the guide element is introduced from the deflected distal end of the catheter through the vessel wall.

36. The method of claim 35, wherein the catheter comprises the stimulation lead.

37. The method of claim 30, further comprising occluding the flow of blood through the blood vessel upstream from the exit point.

38. The method of claim 30, wherein the stimulation lead is an arrayed stimulation lead.

39. The method of claim 30, further comprising advancing the stimulation lead from the exit point along a sub-arachnoid space of the patient's head.

40. The method of claim 30, wherein the sealing mechanism is a thrombogenic material.

41. The method of claim 30, wherein the sealing mechanism is a radially expanding mechanism.

42. The method of claim 30, wherein the sealing mechanism is a radially expanding substance.

43. The method of claim 30, wherein the sealing mechanism is an ablative element.

* * * * *